US008357491B2

(12) United States Patent
Clarke et al.

(10) Patent No.: US 8,357,491 B2
(45) Date of Patent: Jan. 22, 2013

(54) ISOLATION AND USE OF SOLID TUMOR STEM CELLS

(75) Inventors: Michael F. Clarke, Palo Alto, CA (US); Sean J. Morrison, Ann Arbor, MI (US); Max S. Wicha, Ann Arbor, MI (US); Muhammad Al-Hajj, Eagleville, PA (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 12/979,991

(22) Filed: Dec. 28, 2010

(65) Prior Publication Data

US 2011/0092378 A1   Apr. 21, 2011

Related U.S. Application Data

(63) Continuation of application No. 11/788,489, filed on Apr. 20, 2007, now abandoned, which is a continuation of application No. 11/529,869, filed on Sep. 29, 2006, now Pat. No. 7,850,961, which is a continuation of application No. 10/343,692, filed as application No. PCT/US01/24243 on Aug. 2, 2001, now Pat. No. 7,115,360, which is a continuation of application No. 09/920,517, filed on Aug. 1, 2001, now Pat. No. 6,984,522.

(60) Provisional application No. 60/240,317, filed on Oct. 13, 2000, provisional application No. 60/222,794, filed on Aug. 3, 2000.

(51) Int. Cl.
*C12Q 1/68* (2006.01)
*C12P 19/34* (2006.01)
(52) U.S. Cl. ...................... 435/6.12; 435/91.2
(58) Field of Classification Search .................. None
See application file for complete search history.

(56) References Cited

U.S. PATENT DOCUMENTS

| 4,411,990 | A |  | 10/1983 | Salmon et al. |
| 6,117,985 | A | * | 9/2000 | Thomas et al. ............... 530/413 |
| 2002/0061289 | A1 | * | 5/2002 | Boman ........................ 424/85.1 |
| 2004/0018546 | A1 | * | 1/2004 | Hung ................................ 435/6 |

FOREIGN PATENT DOCUMENTS

WO      00/20576      4/2000

OTHER PUBLICATIONS

Schutze et al. Identification of expressed genes by laser-mediated manipulation of single cells. Nature Biotech. (1998) vol. 16, pp. 737-742.*
Shimizu, K. et al. "Manic fringe and lunatic fringe modify different sites of the Notch2 extracellular region, resulting in different signaling modulation" J Biol.Chem. 276, 25753-25758 (2001).
Hicks, et al. "Fringe differentially modulates Jagged1 and Delta1 signalling through Notch1 and Notch2" N-at Cell Biol. (8) pp. 515-520 (2000).
May, W., et al. "EWS/FLI1-induced manic fringe renders NIH 3T3 cells tumorigenic" Nat Genet. 17(4) pp. 495-497 (1997).
Hanahan, D. & Weinberg, R. A. "The hallmarks of cancer" Cell 100, 57-70 (2000).
Edwards et al., "A Newly Defined Property of Somatotropin: Priming of Macrophages for Production of Superoxide Anion," Science, 239: 769 (1988).
Fuh, et al., "Rational design of potent antagonists to the human growth hormone receptor," Science, 1992; 256: 1677-1680.
Herman-Bonert et al., Growth hormone receptor antagonist therapy in acromegalic patients resistant to somatostatin anaologs, J. Clin. Endocrinol Metab. 2000; 85:2958-2961.
Hughes and Friesen, "The Nature and Regulation of the Receptors for the Pituitary Growth Horman," Annu. Rev. Physiol. 47: 469 (1985).
Isaksson et al., "Mode of Action of Pituitary Growth Hormone on Target Cells," Annu. Rev. Physiol. 47: 483 (1985).
Berry. et al. -Germ-line tumor formation caused by activation of glp-1, a *Caenorhabditis elegans* member of the Notch family of receptors-, Development, vol. 124. pp. 925-936 (1997).
Rocha Lima et al. Seminars in Oncology, 2001 Suppl. 10 vol. 28, pp. 34-43.
Riechmann et al. Nature, vol. 332: 323-327 1988.
Berg et al., PNAS, vol. 88, 1991, pp. 4723-4727.
Chamow et al. J Immunol vol. 153, 1994, p. 4268.
Sambrook et al, "Molecular Cloning: A laboratory Manual," 1989, Cold Spring Harbor Press pp. 9.31-9.58.
Sumerdon et al. J Clin One vol. 9, 1991, pp. 631-640.
Griffin et al., J Clin One vol. 9, 1991, pp. 631-640.
Lauffer Magnetic Resonance in Medicine vol. 22, 1991, pp. 339-342.
Khaw et al., Science vol. 209, 1980, p. 295.
Scheinberg et al., Science, vol. 1980, p. 295.
Hnatowich et al., Int. J Appl. Radiat. lot. vol. 33, 1982, p. 327.
Koehle, Milestein Nature vol. 256, 1975, p. 495.
Zuckennann et al., J Med Chem vol. 37, 1994, p. 2678-85.
Lam Anticancer Grug Des vol. 12, 1997, p. 145.
Dewitt et al. Proc natl Acad Sci., vol. 90, pp. 6909, 1993.
Erb et al., Proc Nad Acad Sci vol. 91 1994, p. 11422.
Cho et al., Science, vol. 261, 1993, p. 1303.

(Continued)

*Primary Examiner* — Kenneth R. Horlick
*Assistant Examiner* — David Thomas
(74) *Attorney, Agent, or Firm* — Casimir Jones, S.C.

(57) ABSTRACT

A small percentage of cells within an established solid tumor have the properties of stem cells. These solid tumor stem cells give rise to both more tumor stem cells and to the majority of cells in the tumor that have lost the capacity for extensive proliferation and the ability to give rise to new tumors. Thus, solid tumor heterogeneity reflects the presence of tumor cell progeny arising from a solid tumor stem cell.
We have developed a xenograft model in which we have been able to establish tumors from primary tumors via injection of tumors in the mammary gland of severely immunodeficient mice. These xenograft assay have allowed us to do biological and molecular assays to characterize clonogenic solid tumor stem cells.
We have also developed evidence that strongly implicates the Notch pathway, especially Notch 4, as playing a central pathway in carcinogenesis.

21 Claims, 26 Drawing Sheets

OTHER PUBLICATIONS

Carrell et al., Angew Chem Int Ed Engl. vol. 33, 1994, p. 2059.
Carrell et al., Angew Chem Int Ed Engl vol. 33, 1994, p. 2061.
Gallop et al., J Med Chem vol. 37, 1994, p. 1233.
Houghten Biotechniques col. 13, 1992, pp. 412-421.
Lam Nature vol. 354, 1991, pp., 82-84.
Fodor Nature col. 364, 1993, pp. 555-556.
Cull et al., Proc Nad Acad Sci USA vol. 89, 1992, p. 1865-1869.
Scott; Smith Science vol. 249, 1990, pp. 386-390.
Devlin Science vol. 249, 1990, pp. 404-406.
Cwirla et al. Proc. Nati. Acad. Sci. vol. 87, 1990, pp. 6378-6382.
Felici J. Mol. Biol. vol. 222, 1991, p. 301.
McConnell et al. Science vol. 257, 1992, pp. 1906-1912.
Sjolander; Urbaniczky Anal. Chem. vol. 63, 1991, pp. 2338-2345.
Szabo et al. Curr. Opin. Struct. Biol. vol. 5, 1995, pp. 699-705.
Rivas; Minton Trends Biochem Sci vol. 18, 1993, pp. 284-287.
'Current Protocols in Molecular Biology', 1999, J. Wiley.
Heegaard J. Mol. Recognit vol. 11, 1998, pp. 141-148.
Hage and Tweed J. Chromatogr. Biomed. Sci. Appl vol. 699, 1997, pp. 499-525.
Zervos et al. Cell vol. 72, 1993, pp. 223-232.
Madura et al. J. Biol. Chem. vol. 268, 1993, pp. 12046-12054.
Bartel et al. Biotechniques vol. 14, 1993, pp. 920-924.
Iwabuchi et al. Oncogene vol. 8, 1993, pp. 1693-1696.
Jang et al., "Notch Signaling as a Target in Multimodality Cancer Therapy," Curr Opin Mol Ther, 2000, 2:55-65.
Weng et al., "Multiple niches for Notch in cancer: context is everything," Current Opinion in Genetics and Development, 2004, 14:48-54.
Culp and Kogerman, "Plasticity of CD44S Expression During Progression and Metastasis of Fibrosarcoma in an Animal Model System," Frontiers in Bioscience, 1998, 3:d672-683.

\* cited by examiner

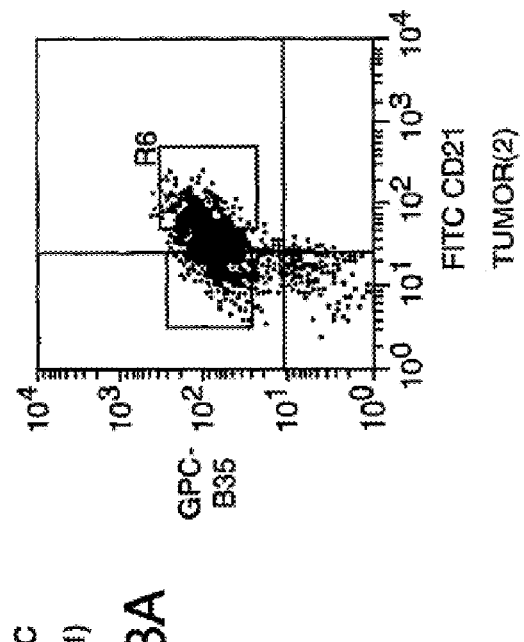
FIG. 3A  FIG. 3B  FIG. 3C

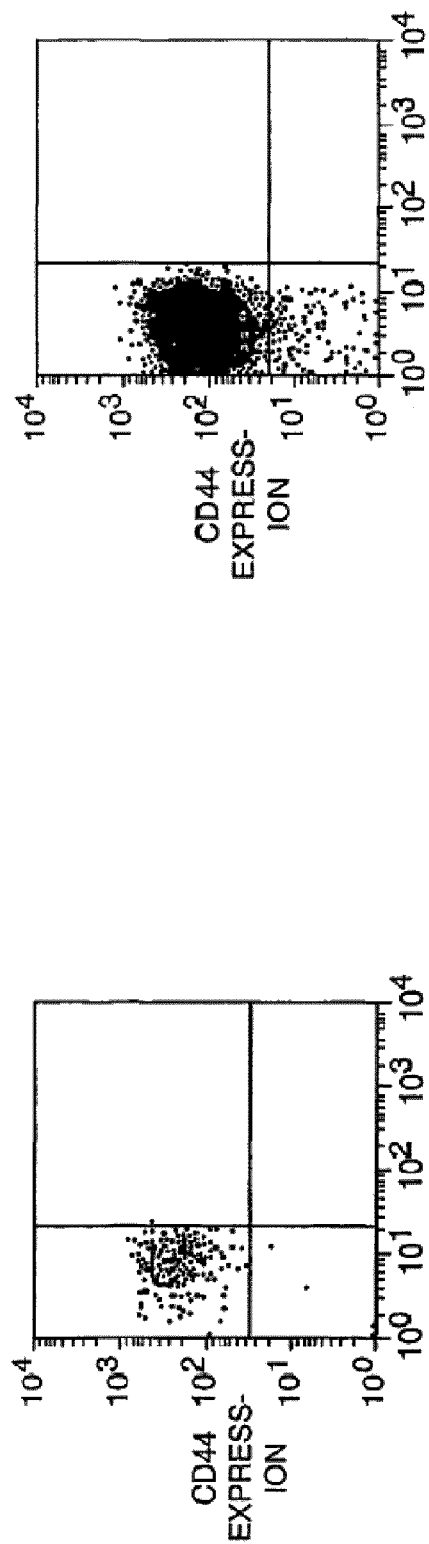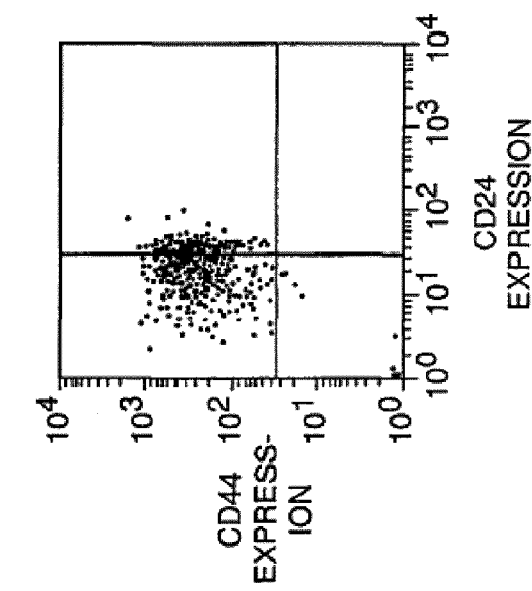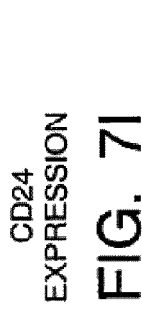

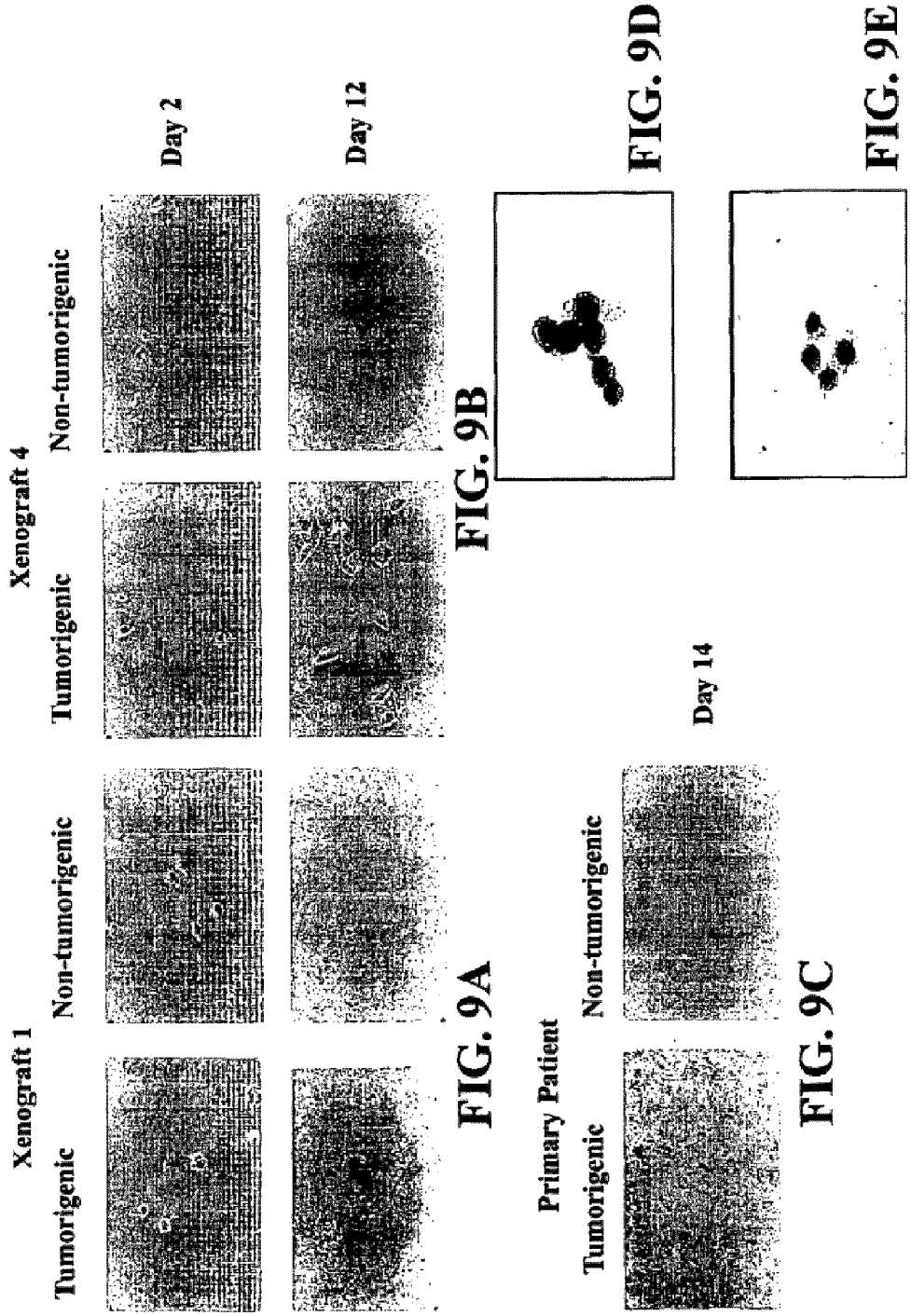

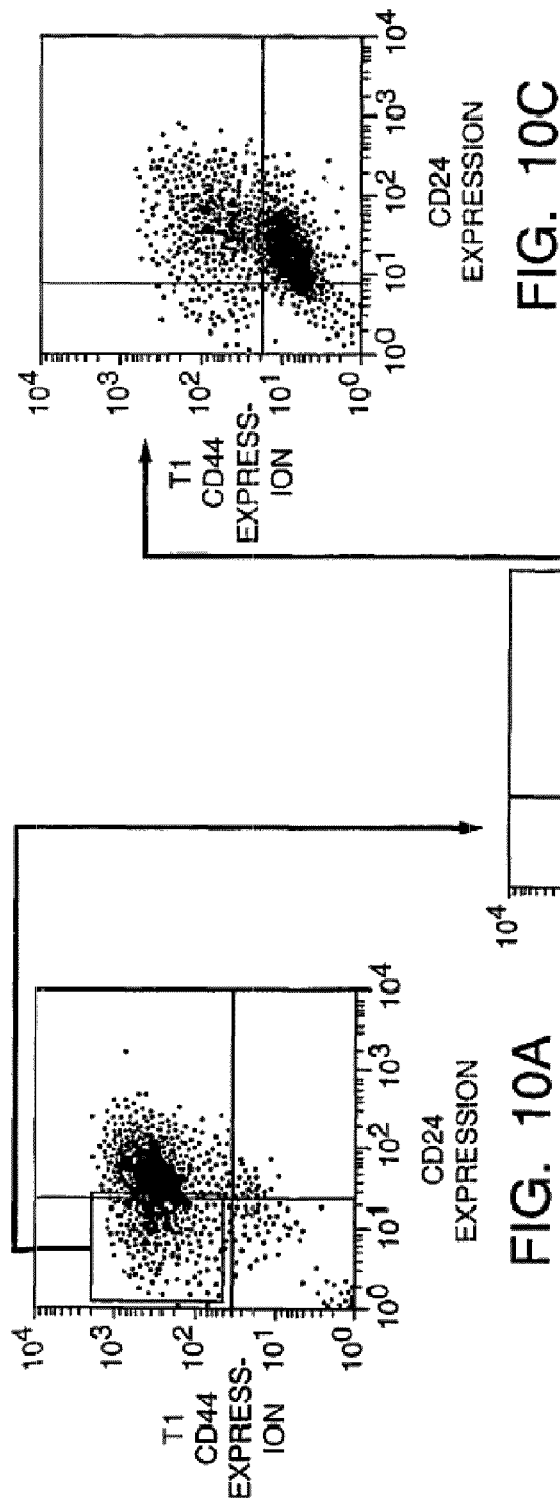

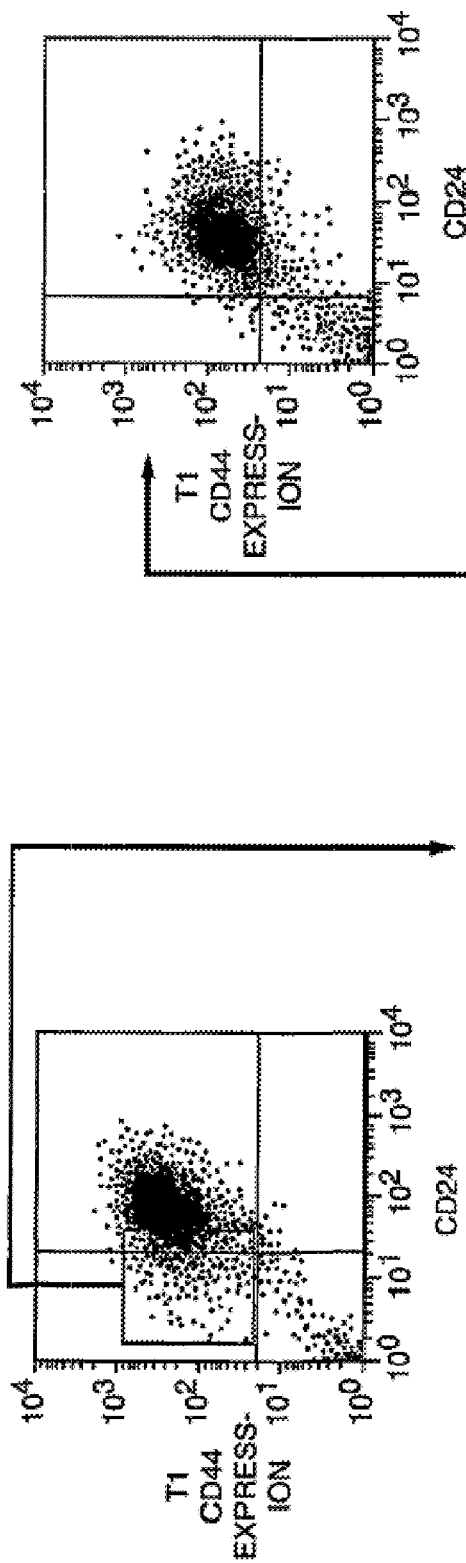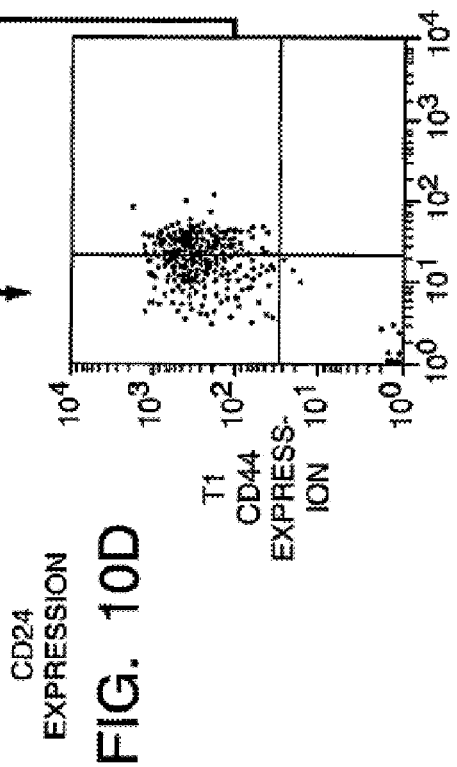

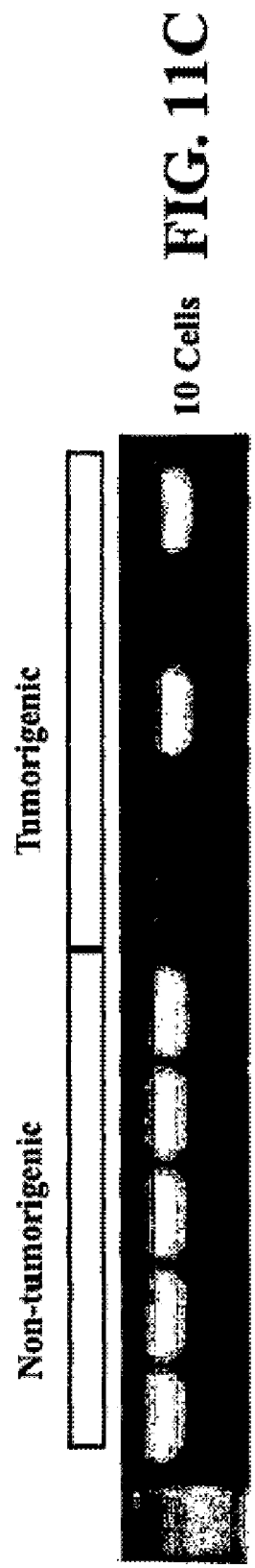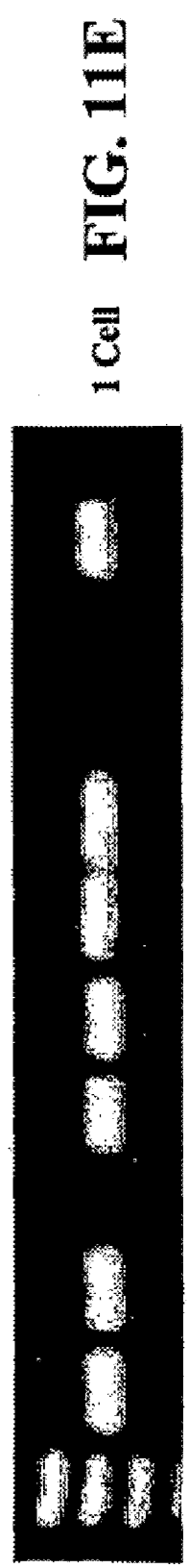

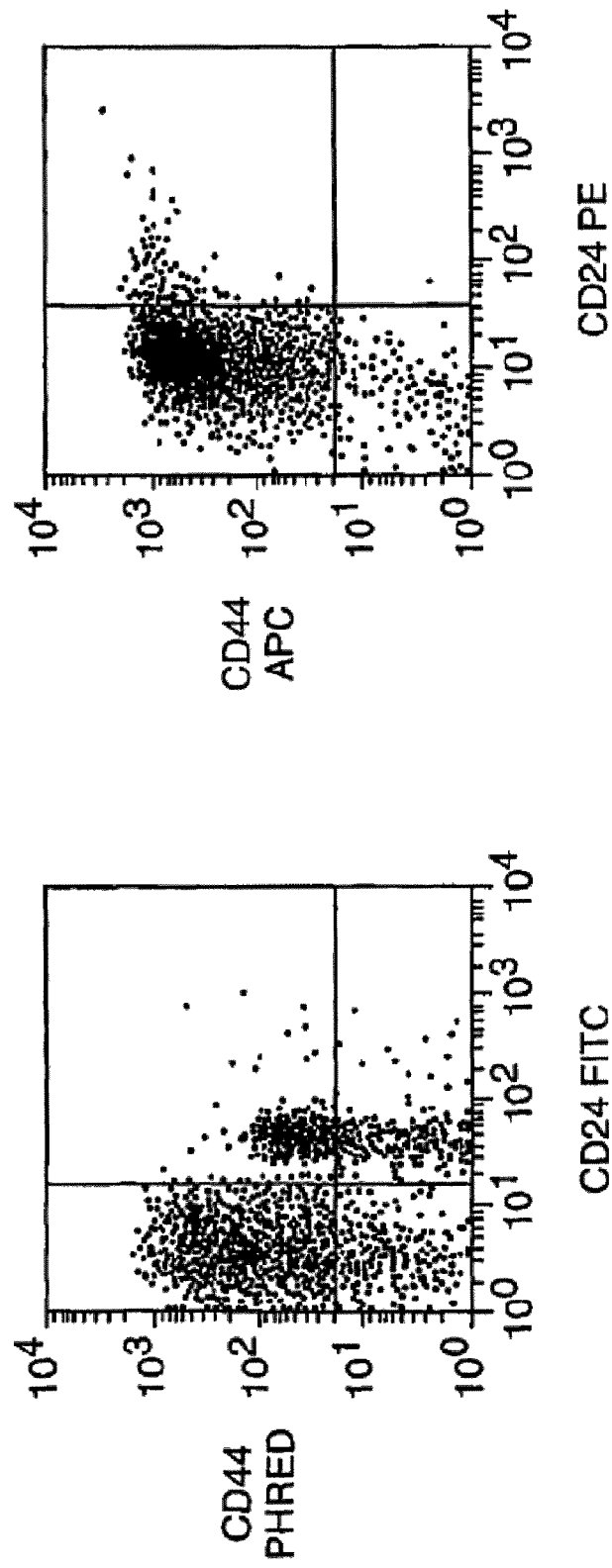

SEQUENCE LISTING

<160> NUMBER OF SEQ ID NOS: 1

<210> SEQ ID NO 1
<211> LENGTH: 19
<212> TYPE: PRT
<213> ORGANISM: Homo sapiens

<400> SEQUENCE: 1

```
Leu Leu Cys Val Ser Val Val Arg Pro Arg Gly Leu Leu Cys Gly Ser
1               5                   10                  15

Phe Pro Glu
```

ISOLATION AND USE OF SOLID TUMOR STEM CELLS

CROSS REFERENCE TO RELATED APPLICATIONS

The present application is a Continuation of U.S. application Ser. No. 11/788,489, filed Apr. 20, 2007, now abandoned which is a Continuation of U.S. application Ser. No. 11/529,869, filed Sep. 29, 2006, which is now U.S. Pat. No. 7,850,961, which is a Continuation of U.S. application Ser. No. 10/343,692, filed Aug. 25, 2003, now U.S. Pat. No. 7,115,360, which is a U.S. National Entry of International Application PCT/US01/24243 filed Aug. 2, 2001, which is a continuation of U.S. application Ser. No. 09/920,517 filed Aug. 1, 2001, now U.S. Pat. No. 6,984,522, which claims priority to U.S. Provisional Application 60/240,317 filed Oct. 13, 2000 and U.S. Provisional Application 60/222,794, filed Aug. 3, 2000, all of which are herein incorporated by reference.

STATEMENT REGARDING FEDERALLY SPONSORED RESEARCH OR DEVELOPMENT

This invention was made with government support under CA075136 awarded by the National Institute of Health. The government has certain rights in the invention.

TECHNICAL FIELD

This invention relates to the diagnosis and treatment of cancer.

BACKGROUND ART

Cancer remains the number two cause of mortality in this country, resulting in over 500,000 deaths per year. Despite advances in detection and treatment, cancer mortality remains high. Despite the remarkable progress in understanding the molecular basis of cancer, this knowledge has not yet been translated into effective therapeutic strategies.

In particular, breast cancer is the most common cancer in American women, with approximately one in nine women developing breast cancer in their lifetime. Unfortunately, metastatic breast cancer is still an incurable disease. Most women with metastatic breast cancer succumb to the disease.

Traditional modes of therapy (radiation therapy, chemotherapy, and hormonal therapy), while useful, have been limited by the emergence of treatment-resistant cancer cells. Clearly, new approaches are needed to identify targets for treating metastatic breast cancer and cancer generally.

DISCLOSURE OF THE INVENTION

The invention is based upon the discovery that a small percentage of cells within an established solid tumor have the properties of "stem cells". These solid tumor "stem" cells give rise both to more solid tumor stem cells and to the majority of cells in the tumor, cancer cells that have lost the capacity for extensive proliferation and the ability to give rise to new tumors. Thus, solid tumor cell heterogeneity reflects the presence of a variety of tumor cell types that arise from a solid tumor stem cell.

The previous failure of cancer therapies to significantly improve patient outcome has been due in part to the failure of these therapies to target the solid tumor stem cells within a solid tumor that have the capacity for extensive proliferation and the ability to give rise to all other solid tumor cell types. This invention provides a way that anti-cancer therapies can be directed, both generally and now specifically directed, against the solid tumor stem cells. The directed anti-cancer therapies of the invention thus result in much more effective and durable therapeutic responses.

By the methods of the invention, one can characterize the phenotypically heterogeneous populations of cells within a solid tumor. Populations of cells obtained from the solid tumor are isolated and structurally characterized using Fluorescence Activated Cell Sorting (FACS). In particular, one can identify, isolate, and characterize a phenotypically distinct cell population within a tumor having the stem cell properties of extensive proliferation and the ability to give rise to all other tumor cell types. Solid tumor stem cells are the truly tumorigenic cells that are capable of re-establishing a tumor following treatment.

The invention provides in vivo and in vitro assays of solid tumor stem cell function and cell function by the various populations of cells isolated from a solid tumor. The invention provides methods for using the various populations of cells isolated from a solid tumor (such as a population of cells enriched for solid tumor stem cells) to identify factors influencing solid tumor stem cell proliferation, to analyze populations of cells isolated from solid tumors for gene expression patterns or protein expression patterns, to identify new anti-cancer drug targets, to predict the sensitivity of tumors from individual patients to existing anti-cancer treatment regimens, to model anti-cancer treatment, to test new therapeutic compounds, to identify and test new diagnostic markers, to treat tumors, to produce genetically modified solid tumor stem cells, and to prepare cDNA libraries and microarrays of polynucleotides and polypeptides from solid tumor stem cells.

The invention provides a method for consistently growing solid tumor cells in vivo. The invention also provides a method to grow solid tumor cells that are in single cell suspension or in small aggregates. Moreover, the invention provides a chimeric animal (a xenograft model) in which tumors can be established from solid tumor primary cells and in which the tumors derived from these solid tumor cells can be tested. Furthermore, the invention provides tumor banks large enough to perform substantial numbers of bioassays derived from single solid tumor stem cells.

In its several aspects, the invention usefully provides methods for screening for anti-cancer agents; for the testing of anti-cancer therapies; for the development of drugs targeting novel pathways; for the identification of new anti-cancer therapeutic targets; the identification and diagnosis of malignant cells in pathology specimens; for the testing and assaying of solid tumor stem cell drug sensitivity; for the measurement of specific factors that predict drug sensitivity; and for the screening of patients (e.g., as an adjunct for mammography). The invention can be used as a model to test patients' tumor sensitivity to known therapies; as a model for identification of new therapeutic targets for cancer treatment; as a system to establish a tumor bank for testing new therapeutic agents for treatment of cancer; and as a system to identify the tumorigenic cancer cells. Also, the invention provides synergy between the methods of the invention and breast cancer genomic databases, for an improved anti-cancer drug discovery.

BRIEF DESCRIPTION OF DRAWINGS

FIG. 2 is a set of FACS plots of breast cancer tumor cells. Mice were implanted with primary breast cancer tumor cells removed from two human patients. Resultant tumors were removed from the mouse and single cell suspensions were made. Cells were stained with anti-CD44-PE, anti-520C9-APC, anti-mouse H2K-FITC (which stains infiltrating mouse cells) and Propidium Iodide (PI, which stains dead cells).

FIG. 3 is a set of FACS plots showing the expression of CD24 by malignant breast cells. Cells were isolated and stained as described in FIG. 2. Mouse cells and dead cells were gated out of the analysis. The FIGS. 3A, 3B and 3C show FACS plots of cells from three breast cancer tumors are shown obtained from mice implanted with Tumor(1), Tumor (2) and Tumor(3), respectively. Note that cells from all three tumors have a similar phenotype.

In FIG. 8B, the $ESA^+$ $B38.1^+CD24^{-/lo}LINEAGE^-$ cells (left panel) and the remaining $LINEAGE^-H2K^-$ cells (right panel) were collected using .flow cytometry.

FIG. 9 is the results of an in vitro clonogenic assay. Flow cytometry was used to isolate tumorigenic cell or the rest of the non-tumorigenic neoplastic (non-tumorigenic cells) as described. The cells were placed in tissue culture medium containing soluble Delta for the indicated number of days. The tumorigenic and non-tumorigenic xenograft Tumor 1 (T1) (FIG. 9A), Tumor 4 (T4) (FIG. 9B) or primary patient (FIG. 9C) cells are shown at the indicated time after being placed in tissue culture. T4 cells were stained with Papanicolaou stain and examined under light microscopy (100× objective). Note that both the non-tumorigenic (FIG. 9D) and tumorigenic (FIG. 9E) populations consist of neoplastic cells with large nuclei and prominent nucleoli. Note that the number of cells that attached to the tissue culture plate is similar in both populations, but that the tumorigenic population always gave rise to colonies. Non-tumorigenic populations do not give rise to established colonies (or only for brief periods, about 2-6 days).

FIG. 10 is a set of dot plots showing the phenotypic diversity in tumors arising from $B38.1^+CD44^+CD24^{-/lo}LINEAGE^-$ cells. The dot plots depict the CD24 and CD44 staining patterns of live human LINEAGE cells from Tumor T1 (FIG. 10A-FIG. 10C) or Tumor T2 (FIG. 10-FIG. 10F). FIG. 10A and FIG. 10D show unfractionated T1 or T2 cells obtained from tumors that had been passaged once in NOD/SCID mice. B38.1$^+$CD44$^+$CD24$^{-/lo}$LINEAGE$^-$ cells from T1 (FIG. 10B) or T2 (FIG. 10E) were isolated as described in FIG. 2, above. The B38.1$^+$CD44$^+$CD24$^{-/lo}$LINEAGE$^-$ populations reanalyzed in FIG. 10B and FIG. 10E were injected into the mammary fat pads of NOD/SCID mice. FIG. 10C and FIG. 10F depict analyses of the tumors that arose from these B38.1$^+$CD44$^+$CD24$^{-/lo}$LINEAGE$^-$ cells. Note that in both cases, the B38.1$^+$CD44$^+$CD24$^{-/lo}$LINEAGE$^-$ cells formed tumors that contained a phenotypically diverse population of cells similar to that observed in the original tumor.

FIG. 21 is an analysis of as cites fluid for ovarian cancer stem cells. Cells were stained with anti-B38.1-APC, anti-CD44-PE, anti-CD24-FITC, anti-Lineage-Cytochrome and 7AAD. Dead cells (7AAD$^+$), and LINEAGE$^+$ cells were eliminated from the analyses. Note that there is a distinct CD44$^+$CD24$^{-/lo}$ LINEAGE$^-$ population of cells that resembles the breast cancer stem cells.

FIG. 22 is an analysis of sarcoma cells for solid tumor stem cells. P1 sarcoma cells growing in the xenograft model were stained with anti-B38.1-APC, anti-CD44-PE, anti-CD24 ¬FITC, anti-LINEAGE-Cytochrome, anti-H2K-Cytochrome and 7AAD. Dead cells (7AAD$^+$), LINEAGE$^+$ cells and mouse cells were eliminated from the analyses. Note that the lineage cocktail in this analysis did not include CD10, CD31 or CD140b. Also note that there is a distinct CD44$^+$CD24$^{-/lo}$ LINEAGE$^-$ population of cells.

MODES FOR CARRYING OUT THE INVENTION

Figure 1A:
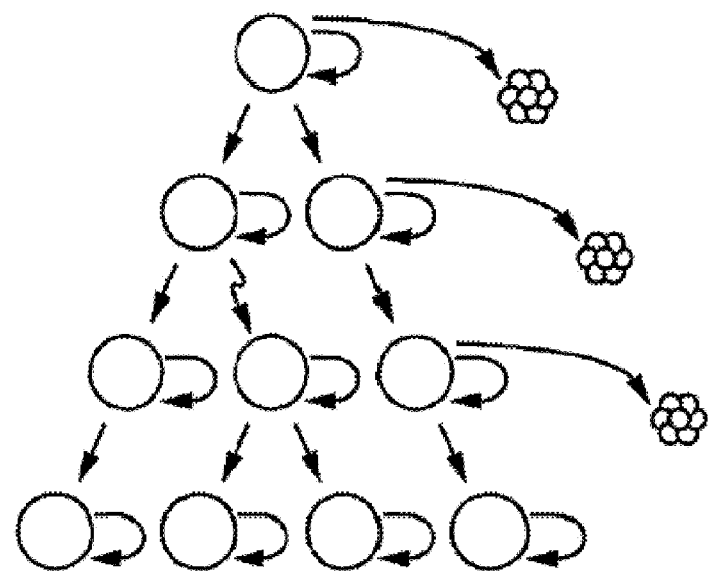
FIG. 1 shows two models of solid tumor heterogeneity. In the classic model (FIG. 1A), mutations or environmental differences cause tumor cells to adopt a variety of different phenotypes. Environmentally determined differences in phenotype, represented by white, green, and red cells, may be reversible while mutationally determined changes in phenotype, represented by purple cells, may not be reversible. Many cells with a variety of different phenotypes are thought to have the potential to proliferate extensively and form new tumors. The tumor stem cell model (FIG. 1B) is distinguished by having only a minor population of tumor cells that are tumorigenic (yellow cells). These tumor stem cells are characterized by indefinite proliferative potential, the ability to form new tumors, and the ability to give rise to heterogeneous non-tumorigenic cancer cells that typically form the bulk of a tumor.

Stem cells and solid tumor heterogeneity models. Solid tumors are composed of heterogeneous cell populations. For example, breast cancers are a mixture of cancer cells and normal cells, including mesenchymal (stromal) cells, inflammatory cells, and endothelial cells. Classic models hold that phenotypically distinct cancer cell populations all have the capacity to proliferate and give rise to a new tumor (FIG. 1A). In the classical model, tumor cell heterogeneity results from environmental factors as well as ongoing mutation within cancer cells resulting in diverse populations of tumorigenic cells and all populations of cells would have similar tumorigenic potential. (Pandis et al, Genes, Chromosomes &Cancer 12: 122-129 (1998); Kuukasjarvi et al., Cancer Res. 57: 1597-1604 (1997); Bonsing et al., Cancer 71: 382-391 (1993); Bonsing et al., Genes Chromosomes & Cancer 82: 173-183 (2000); Beennan H et al., Cytometry 12(2): 147-54 (1991); Aubele M & Werner M, Analyt. Cell. Path. 19: 53 (1999); Shen L et al., Cancer Res. 60: 3884 (2000).).

Figure 1B:
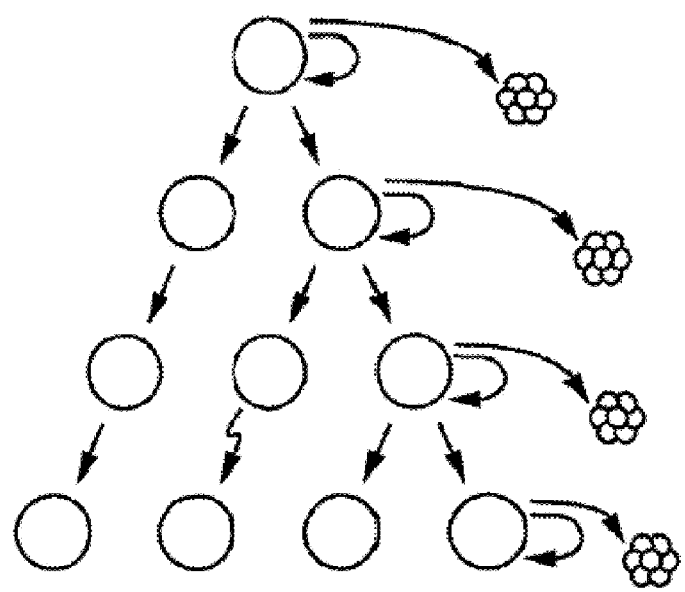

This invention is based upon an alternative model of solid tumor cell heterogeneity, in which a solid tumor results from a "solid tumor stem cell" (or "cancer stem cell" from a solid tumor) and the subsequent chaotic development of the solid tumor stem cell. In this stem cell model (FIG. 1B), solid tumors contain a distinct, limited (or possibly rare) subset of cells that share the properties of normal "stem cells", in that they proliferate extensively or indefinitely and that they efficiently give rise to additional solid tumor stem cells. Within an established solid tumor, most cells have lost the ability to proliferate extensively and form new tumors, but solid tumor stem cells proliferate extensively and give rise to additional solid tumor stem cells as well as to other tumor cells that lack tumorigenic potential. It is this solid tumor stem cell population that proliferates and ultimately proves fatal.

To distinguish between these models, the deficiencies of the previous clonogenic assays (see, below) must be overcome. To prove the existence of a consistent stem cell population rather that a constant low probability of tumorigenicity in any cell type, one must be able to purify the stem cells and show that they are highly enriched for tumorigenicity, while the remainder of the neoplastic cells are depleted of such activity. The invention provides this ability.

The ability to isolate and analyze cell populations within a solid tumor, based upon structural features of the solid tumor stem cells, described herein, allows one skilled in the art of oncology or stem cell biology to distinguish between the two models shown in FIG. 1. By this invention, solid tumor stem cells and cell populations from solid tumors have been isolated and analyzed. Moreover, these solid tumor stem cells have very high or unlimited proliferative potential, and thus represent the truly tumorigenic population. According to the solid tumor stem cell model and the results provided below (see, EXAMPLES), these tumorigenic cells are the clonogenic cells of solid tumors.

During normal animal development, cells of most or all tissues are derived from normal precursors, called stem cells (Morrison et al., Cell 88(3): 287-98 (1997); Morrison et al., Curr. Opin. Immunol. 9(2): 216-21 (1997); Morrison et al., Annu Rev. Cell. Dev. Bioi. 11: 35-71 (1995)). The term "stem cell" is known in the art to mean (1) that the cell is a cell capable of generating one or more kinds of progeny with reduced proliferative or developmental potential; (2) that the cell has extensive proliferative capacity; and (3) that the cell is capable of self-renewal or self-maintenance (see, Potten et al., Development 110: 1001 (1990); U.S. Pat. Nos. 5,750,376, 5,851,832, 5,753,506, 5,589,376, 5,824,489, 5,654,183, 5,693,482, 5,672,499, and 5,849,553, all incorporated by reference). In adult animals, some cells (including cells of the blood, gut, breast ductal system, and skin) are constantly replenished from a small population of stem cells in each tissue. Thus, the maintenance of tissues (whether during normal life or in response to injury and disease) depends upon the replenishing of the tissues from precursor cells in response to specific developmental signals.

The best-known example of adult cell renewal by the differentiation of stem cells is the hematopoietic system (see, U.S. Pat. Nos. 5,061,620, 5,087,570, 5,643,741, 5,821,108, 5,914,108, each incorporated by reference). Developmentally immature precursors (hematopoietic stem and progenitor cells) respond to molecular signals to gradually form the varied blood and lymphoid cell types. Stem cells are also found in other tissues, including epithelial tissues (see, Slack, Science 287: 1431 (2000)) and mesenchymal tissues. (see, U.S. Pat. No. 5,942,225; incorporated by reference). In normal breast development, a normal stem cell gives rise to differentiated progeny to form a normal ductal system. Kordon & Smith, Development 125: 1921-1930 (1998); see also, U.S. Pat. Nos. 5,814,511 and 5,650,317.

By this invention, the principles of normal stem cell biology have been applied to isolate and characterize solid tumor stem cells. Examples of solid tumors from which solid tumor stem cells can be isolated or enriched for according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. The invention is applicable to sarcomas (see, FIG. 22) and epithelial cancers, such as ovarian cancers (see, FIG. 21) and breast cancers (see, EXAMPLES).

Solid tumor stem cells are defined structurally and functionally as described herein; using the methods and assays similar to those described below. Because tumor cells are known to evolve phenotypically and functionally over time as additional genetic mutations occur, the solid tumor stem cells may change phenotypically and functionally over time in an individual patient. Nevertheless, one can use the method of the invention, employing the markers disclosed herein, which are consistently useful in the isolation or identification of solid tumor stem cells in a majority of patients.

Also, solid tumor stem cells undergo "self-renewal" and "differentiation" in a chaotic development to form a tumor, give rise to abnormal cell types, and may change over time as additional mutations occur. The functional features of a solid tumor stem cell are that they are tumorigenic, they give rise to additional tumorigenic cells ("self-renew"), and they can give rise to non-tumorigenic tumor cells ("differentiation").

The developmental origin of solid tumor stem cells can vary between different types of solid tumor cancers. Solid tumor stem cells may arise either as a result of genetic damage that deregulates the proliferation and differentiation of normal stem cells (Lapidot et al., Nature 367(6464): 645-8 (1994)) or by the dysregulated proliferation of a normal restricted progenitor or a normal differentiated cell type.

Typically, solid tumors are visualized and initially identified according to their locations, not by their developmental origin.

By contrast, a non-tumorigenic cell from a solid tumor is a cell from a population that fails to form a palpable tumor upon transplantation into an immunocompromised mouse, wherein if the same number of unfractionated, dissociated tumor cells were transplanted under the same circumstances, the solid tumor stem cells would form a palpable tumor in the same period of time. Thus non-tumorigenic cells are depleted for tumor forming activity in an animal model.

A "palpable tumor" is known to those in the medical arts as a tumor that is capable of being handled, touched, or felt.

Because the tumorigenic changes are intrinsic to solid tumor stem cells, even after they have been removed from their normal environment within the tumor, the invention provides several novel uses:

(1) by identifying the genes and proteins expressed by solid tumor stem cells it is possible to identify proteins whose function is necessary for tumorigenesis and which represent novel drug targets;

(2) by purifying solid tumor stem cells based on phenotypic markers it is possible to study their gene expression patterns and functions much more directly and efficiently;

(3) by developing in vitro and in vivo assays of solid tumor stem cell function it is possible 'to more effectively test the effects of potential therapeutic compounds;

(4) by identifying markers of solid tumor stem cells it is possible to more effectively diagnose the presence of malignant cells (even those that do not depend on rare environmental characteristics for their ability to make tumors); and (5) by isolating solid tumor stem cells from individual patients and transplanting them into in vitro and in vivo functional assays it is possible to test the effectiveness of different drug regimens against them. Thus, it is possible to predict drug sensitivity and drug resistance.

The solid tumor stem cells of the model of the invention differs from the "cancer stem line" provided by U.S. Pat. No. 6,004,528. In that patent, the "cancer stem line" is defined as a slow growing progenitor cell type that itself has few mutations but which undergoes symmetric rather than asymmetric cell divisions as a result of tumorigenic changes that occur in the cell's environment. This "cancer stem line" hypothesis thus proposes that highly mutated, rapidly proliferating tumor cells arise largely as a result of an abnormal environment, which causes relatively normal stem cells to accumulate and then undergo mutations that cause them to become tumor cells. U.S. Pat. No. 6,004,528 proposes that such a model can be used to enhance the diagnosis of cancer. The solid tumor stem cell model is fundamentally different than the "cancer stem line" model and as a result exhibits utilities not offered by the "cancer stem line" model. First, solid tumor stem cells are not "mutationally spared". The "mutationally spared cancer stem line" described by U.S. Pat. No. 6,004,528 may be considered a pre-cancerous lesion, while the solid tumor stem cells described of this invention are cancer cells that themselves contain the mutations that are responsible for tumorigenesis. That is, the solid tumor stem cells ("cancer stem cells") of the invention would be included among the highly mutated cells that are distinguished from the "cancer stem line" in U.S. Pat. No. 6,004,528. Second, the genetic mutations that lead to cancer are largely intrinsic within the solid tumor stem cells rather than being environmental. The solid tumor stem cell model predicts that isolated solid tumor stem cells can give rise to additional tumors upon transplantation (thus explaining metastasis) while the "cancer stem line" model would predict that transplanted "cancer stem line" cells would not be able to give rise to a new tumor, since it was their abnormal environment that was tumorigenic. Indeed, the ability to transplant dissociated, and phenotypically isolated human solid tumor stem cells to mice (into an environment that is very different from the normal tumor environment), where they still form new tumors, distinguishes the present invention from the "cancer stem line" model. Third, solid tumor stem cells likely divide both symmetrically and asymmetrically, such that symmetric cell division is not an obligate property. Fourth, solid tumor stem cells may divide rapidly or slowly, depending on many variables, such that a slow proliferation rate is not a defining characteristic.

As described above, solid tumor stem cells can be operationally characterized by cell surface markers. These cell surface markers can be recognized by reagents that specifically bind to the cell surface markers. For example, proteins, carbohydrates, or lipids on the surfaces of solid tumor stem cells can be immunologically recognized by antibodies specific for the particular protein or carbohydrate (for construction and use of antibodies to markers, see, Harlow, Using Antibodies: A Laboratory Manual (Cold Spring Harbor Press, Cold Spring Harbor, N.Y., 1999); see also, EXAMPLES). The set of markers present on the cell surfaces of solid tumor stem cells (the "cancer stem cells" of the invention) and absent from the cell surfaces of these cells is characteristic for solid tumor stem cells. Therefore, solid tumor stem cells can be selected by positive and negative selection of cell surface markers. A reagent that binds to a solid tumor stem cell is a "positive marker" (i.e., a marker present on the cell surfaces of solid tumor stem cells) that can be used for the positive selection of solid tumor stem cells. A reagent that binds to a solid tumor stem cell "negative marker" (i.e., a marker not present on the cell surfaces of solid tumor stem cells but present on the surfaces of other cells obtained from solid tumors) can be used for the elimination of those solid tumor cells in the population that are not solid tumor stem cells (i.e., for the elimination of cells that are not solid tumor stem cells).

In one embodiment, the discrimination between cells based upon the detected expression of cell surface markers is by comparing the detected expression of the cell surface marker as compared with the mean expression by a control population of cells. For example, the expression of a marker on a solid tumor stem cell can be compared to the mean expression of the marker by the other cells derived from the same tumor as the solid tumor stem cell. Other methods of discriminating among cells by marker expression include methods of gating cells by flow cytometry based upon marker expression (see, Givan A, Flow Cytometry: First Principles, (Wiley-Liss, New York, 1992); Owens M A & Loken M R., Flow Cytometry: Principles for Clinical Laboratory Practice, (Wiley-Liss, New York, 1995)).

Solid tumor stem cell positive markers may also be present on cells other than solid tumor stem cells. Solid tumor stem cell negative markers may also be absent from cells other than solid tumor stem cells. While it is rare to identify a single marker that identifies a stem cell, it has often been possible to identify combinations of positive and negative markers that uniquely identify stem cells and allow their substantial enrichment in other contexts. Morrison et al., Cell 96(5): 737-49 (1999); Morrison et al., Proc. Natl. Acad. Sci. USA 92(22): 10302-6 (1995); Morrison & Weissman, Immunity 1(8): 661-73 (1994).

A "combination of reagents" is at least two reagents that bind to cell surface markers either present (positive marker) or not present (negative marker) on the surfaces of solid tumor stem cells, or to a combination of positive and negative markers (see, EXAMPLES 7 and 8, TABLE 6). The use of a combination of antibodies specific for solid tumor stem cell surface markers results in the method of the invention being useful for the isolation or enrichment of solid tumor stem cells from a variety of solid tumors, including sarcomas, ovarian cancers, and breast tumors. Guidance to the use of a combination of reagents can be found in PCT patent application WO 011052143 (Morrison & Anderson), incorporated by reference.

By selecting for phenotypic characteristics among the cells obtained from a solid tumor, solid tumor stem cells can be isolated from any animal solid tumor, particularly any mammalian solid tumor. It will be appreciated that, taking into consideration factors such as a binding affinities, that antibodies that recognize species-specific varieties of markers are used to enrich for and select solid tumor stem cells. Antibodies that recognize the species-specific varieties of CD44, B38.1, CD24 and other markers will be used to enrich for or isolate solid tumor stem cells from that species (for example, antibody to a mouse CD44 for mouse solid tumor stem cells, antibody to a monkey B38.1 for monkey solid tumor stem cells, etc.).

An efficient xenograft model of human breast cancer. The invention provides a xenograft model in which to establish tumors by the injection of solid tumor cells into a host animal. The host animal can be a model organism such as nematode, fruit fly, zebrafish; preferably a laboratory mammal such as a mouse (nude mouse, SCID mouse, NOD/SCID mouse, Beige/SC1D Mouse), rat, rabbit, or primate. The severely immunodeficient NOD-SCID mice were chosen as recipients to maximize the participation of injected cells. Immunodeficient mice do not reject human tissues, and SCID and NOD-SCID mice have been used as hosts for in vivo studies of human hematopoiesis and tissue engraftment. McCune et al., Science 241: 1632-9 (1988); Kamel-Reid & Dick, Science 242: 1706-9 (1988); Larochelle et al., Nat. Med. 2: 1329-37 (1996). In addition, Beige/SC1D mice also have been used.

Xenograft tumors have been established from mastectomy specimens of all the patients that have been tested to date (see, EXAMPLE 7). Tumors in mice have also been established from malignant pleural effusions. In addition, tumors have been established by the subcutaneous injection of cells that have been obtained from two sarcomas. Furthermore, for all the tumors that we have attempted, we have been able to make single-cell suspensions (or suspensions with a few aggregates of cell, such as less than 100; preferably less than 10) and then transfer the tumors. This xenograft assay is useful for biological and molecular assays to characterize the tumorigenic, clonigenic solid tumor stem cells.

The NOD/SCID or Beige/SC1D mice can be further immunosuppressed, using VP-16 (see, EXAMPLES 1 and 3), radiation therapy, chemotherapy, or other immunosuppressive biological agents.

This in vivo assay is particularly advantageous for the better understanding of breast cancer and development of new treatments for this disease. Until now, it has been impossible to do biological and molecular studies involving primary breast cancer. Such studies have been limited to cell lines. Unfortunately, it is well known that the many of the fundamental properties of breast cancer cells change in tissue culture. Fenhall et al., British J Cancer 81: 1142-1149 (1999). This latter problem only worsens with continued culturing of the cells.

By contrast, using the method of the invention, breast cancer cells (preferably enriched for breast cancer stem cells) are injected into immunocompromised mice, to grow the tumor. In one embodiment, the cells are injected either into the mammary fat pads of mice or subcutaneously into the mice. Furthermore, tumors can be established from single-cell suspensions (or suspensions with a few aggregates of cell, such as less than 100; preferably less than 10) and then the tumors transferred to other mice.

The enrichment of solid tumor stem cells and the isolation of solid tumor stem cells distinguishes the present invention from the "primary bioassay of human tumor stem cells" referred to in U.S. Pat. No. 4,411,990 (see also, Hamburger et al., Blood 47: 995 (1976); Salmon et al., AACR Abstracts 19: 231, Abstract No. 922 (1978)). In previous tissue culture assays, only a small proportion of the tumor cells were able to form colonies in an in vitro clonogenic assay, and large numbers of cells (such as myeloma and hematopoietic cells) were typically needed to be transplanted to form tumors in vivo. Ogawa M et al., Cancer Research. 31(12): 2116-2119 (1971); Ogawa M et al., Cancer Research 33(12): 3172-3175, 1973. Salmon S E & Hamburger A W, Science 197: 461-463 (1977). Schlag P & Flentje D, Cancer Treatment Reviews 11 Suppl A:131-7 (1984). This led to the hypothesis that only a small number of tumor cells are actually tumorigenic. However, because of technical limitations, this tumorigenic fraction of cells could not be isolated from non-tumorigenic cells and therefore it could not be proven that there were intrinsically different subsets of tumor cells, some with substantial proliferative potential and others with limited potential. That is, unless the tumorigenic cells can be purified and distinguished from the non-tumorigenic cells it remains possible that all tumor cells have a similar low probability of exhibiting clonogenic activity in any assay. Moreover, without the ability to identify and isolate the tumorigenic fraction of cells (the tumor stem cells) U.S. Pat. No. 4,411,990 lacks the utilities described in this invention. For example, without markers to isolate the tumorigenic cells it is not possible to study their gene expression patterns, or their expression of diagnostic markers, or their response to therapeutic agents. Several technical problems prevented prior inventions from isolating tumorigenic cells or tumor stem cells. First, in vitro assays resulted in some initial colony formation, but usually the cells stopped proliferating and could not be grown continuously in culture. Salmon, S. B. & Hamburger A W, Science 197: 461-463 (1977); Schlag P et al., Cancer Treatment Reviews. 11 Suppl A:131-7, (1984); Salmon S E, Recent Results in Cancer Research 94: 8 (1984). Also, cells from many tumors failed to form colonies in vitro at all. Carney D N et al., Stem Cells 1: 149-164 (1981). Similarly, dissociated cells isolated from most solid tumors rarely formed tumors in immunodeficient mouse models. Sakakibara T et al., Cancer J. Si. Am 2: 291-300 (1996); Mueller B & Reisfeld R A, Cancer Metastasis Rev. 10: 193-200, (1991). The observation that only particular clones of immortalized tissue culture cancer cell lines were capable of forming tumors in the in vivo models further illustrates this problem (Hamilton T C et al., Cancer Research 44(11): 5286-90 (1984)). Thus, the limitations in the assays made it impossible to determine whether the colonies arose from stem cells that had lost their capacity to proliferate in vitro, from non-tumorigenic cells that had limited proliferative potential, or whether the small number of cells able to form colonies in vitro was due to a "stem cell" population within the tumor or due to a rare cell that could proliferate in vitro. Furthermore, it was not possible to distinguish phenotypically different populations of cells: prior to this invention, very limited use was made of techniques like flow-cytometry to separate and analyze phenotypically distinct populations of solid tumor cells by flow-cytometry. Indeed, the clonogenic assays used in the prior art did not predict the behavior of an individual patient's tumor and fell out of favor. Von Hoff D D et al., Cancer. 67(1): 20-7 (1991); Federico M et al., Gynecologic Oncology. 55(3 Pt 2): 8156-63 (1994). Thus, the limitations in the cell separation techniques, and the assays used in the prior art made it impossible for them to purify tumorigenic cells. Therefore, it was impossible to prove the existence of hypothetical tumor stem cells.

Role of Notch in breast cancer. The Notch family of receptors has been implicated in stem cell development and differentiation (see, Morrison et al., Cell 101(5): 499-510 (2000); Artavanis-Tsakonas et al., Science 284: 770 (1999); and Artavanis-Tsakonas et al., Science 268: 225-232 (1995); U.S. Pat. No. 6,090,922, incorporated by reference). Notch was originally identified in *Drosophila* through loss-of-function mutations that produced too many neurons at the expense of other cell types. Poulson, Proc. Natl. Acad. Sci. USA 23: 133 (1937). In all animal models tested, mutations in the Notch receptor result in developmental abnormalities. In *C. elegans*, Notch is required for germ line stem cell self-renewal. Berry et al., Development 124(4): 925-36 (1997). In rats, Notch regulates neural crest stem cell differentiation. Morrison et al., Cell 101(5): 499-510 (2000). Transient Notch activation initiates an irreversible switch from neurogenesis to gliogenesis by neural crest stem cells.

Because neighboring cells can express Notch receptors and ligands, one cell can affect the fate of a neighboring cell by activating Notch signaling in the neighboring cell.

Proteins with knife-edge names such as Jagged (Shimizu et al., Journal of Biological Chemistry 274(46):32961-9 (1999); Jarriault et al., Molecular and Cellular Biology 18:7423-7431 (1998)), Serrate, and Delta (and variants of each, such as Delta1, Delta2, Delta3, Delta4, and Jagged2, LAG-2 and APX-1 in *C. elegans*), bind to the Notch receptor and activate a downstream signaling pathway that prevents neighboring cells from becoming neural progenitors. A recently identified ligand is Dll4, a Notch ligand of the Delta family expressed in arterial endothelium. Shutter et al., Genes Dev 14(11): 1313-8 (2000).

Notch ligands may bind and activate Notch family receptors promiscuously. The expression of other genes, like Fringe family members (Panin et al., Nature 387(6636): 908-912 (1997)), may modify the interactions of Notch receptors with Notch ligands. Numb family members may also modify Notch signaling intracellularly.

Ligand binding to Notch results in activation of a presenilin-1-dependent gamma-secretase-like protein that cleaves Notch. De Strooper et al., Naltlre 398: 518-522 (1999), Mumm et al., Molecular Cell. 5: 197-206 (2000). Cleavage in the extracellular region may involve a furin-like convertase. Logeat et al., PNAS USA 95: 8108-8112 (1998). The intracellular domain is released and transactivates genes by associating with the DNA binding protein RBP-J. Kato et al., Development 124: 4133-4141 (1997). Notch 1, Notch 2 and Notch 4 are thought to transactivate genes such as members of the Enhancer of Split (HES) family, while Notch 3 signaling may be inhibitory. Beatus et al., Development 126: 3925-3935 (1999). Finally, secreted proteins in the Fringe family bind to the Notch receptors and modify their function. Zhang & Gridley, Nature 394 (1998).

In mammals, there are four known Notch family members. Notch 4 is the human ortholog of the mouse int-3 oncogene that plays a role in breast cancer in mice. Gallahan et al., Cancer Res. 56(8): 1775-85 (1996); Uyttendaele et al., Development 2122: 251 (1996); Imatani & Callahan, Oncogene 19(2): 223-31 (2000).

The invention is based upon the discovery that Notch 4 plays a role both in normal human breast development and in tumorigenesis. Within an individual tumor, only a small subpopulation of tumorigenic cells expresses high levels of Notch 4. An antibody that recognizes Notch 4 blocks the growth of breast cancer tumor cells in vitro and in vivo (see, EXAMPLES 2, 5, 12 and 0.15). In one embodiment, the antibody binds to the extracellular domain of Notch 4. In a particular embodiment, the antibody binds to the polypeptide region LLCVSVVRPRGLLCGSFPE (LeuLeuCysValSerValValArgProArgGlyLeuLeuCysGlySerPheProGlu) (SEQ ill NO: 1). However, any anti-Notch 4 antibody that inhibits Notch activation can be used to impair tumor survival.

Inhibitors of Notch signaling (such as Numb and Numblike; or antibodies or small molecules that block Notch activation) can be used in the methods of the invention to inhibit solid tumor stem cells. In this manner, the Notch pathway is modified to kill or inhibit the proliferation of solid tumor stem cells.

By contrast, it had previously been found that stimulation of Notch using soluble Delta (Han et al., Blood 95(5): 161625 (2000)), a Notch ligand, promoted growth and survival of tumor cells in vitro. Thus, it had previously been found that stimulation of the Notch pathway promotes growth and survival of the cancer cells.

The invention differs from the manipulation of non-terminally differentiated cells using the Notch pathway provided in U.S. Pat. No. 5,780,300. U.S. Pat. No. 5,780,300 addresses the modification of normal cells, not cancer cells. That patent is directed to methods for the expansion of non-terminally differentiated cells (normal precursor cells) using agonists of Notch function, by inhibiting the differentiation of the cells without inhibiting proliferation (mitotic activity) such that an expanded population of non-terminally differentiated cells is obtained.

These expanded cells can be used in cell replacement therapy, a use that is incompatible with the goal of killing or inhibiting the proliferation of solid tumor stem cells by modifying Notch signaling in this invention.

Therapeutic aspects of the invention. A corollary to the solid tumor stem cell model of the invention is that, to effectively treat cancer and achieve higher cure rates, anti-cancer therapies must be directed against solid tumor stem cells. Since current therapies are directed against the bulk population, they may be ineffective at eradicating solid tumor stem cells. The limitations of current cancer therapies derive from their inability to effectively kill solid tumor stem cells. The identification of solid tumor stem cells permits the specific targeting of therapeutic agents to this cell population, resulting in more effective cancer treatments. This concept would fundamentally change our approach to cancer treatment.

Advances in modem biotechnology have facilitated the identification of new therapeutic targets for cancer treatment. Advances in genomics have made it possible to sequence and identify the 10,000 to 30,000 genes that are expressed in individual cell types. The human genome has been sequenced. This has resulted in the identification of new proteins involved in a myriad of biological processes such as proliferation, cell death and immortalization, providing targets for drug intervention. Although genomics provides a powerful means for identifying drug targets in cancer cells, these targets are only valid if the targets are present within the tumorigenic cell population. To be effective, genomics must be focused on individual populations within the heterogeneous cells that compose a tumor that are responsible for tumorigenic growth. In solid tumors, these are the solid tumor stem cells. Additionally, genomics has not yet been used to identify genes expressed in purified cell populations derived from cancerous tissues.

One of the major problems in identifying new cancer therapeutic agents is determining which of the myriad of genes identified in large scale sequencing projects are the most clinically important drug targets. This is made especially difficult since solid tumors consist of a mixture of a many types of normal cells and a heterogeneous population of tumor cells. One way to reduce the complexity is to make cDNA after microdissection of solid tumors to enrich for tumor cells (see, below). This technique is based on the assumption that the pathologist dissecting out the tumor cells can predict which cells are tumorigenic based upon appearance. However, cells can be morphologically similar and yet remain functionally heterogeneous. Moreover, cells obtained by microdissection are not viable and therefore the functional properties of such cells cannot be tested or verified.

Instead, by the methods of the invention, one can use flow cytometry (such as FACS) and the xenograft animal model of the invention to enrich for specific cell populations. This technique has the advantage of being able to simultaneously isolate phenotypically pure populations of viable normal and tumor cells for molecular analysis. Thus, flow cytometry allows us to test the functions of the cell populations and use them in biological assays in addition to studying their gene expression profiles. Furthermore, such cells can also be characterized in biological assays. For example, mesenchymal (stromal) cells can be analyzed for production of growth factors, matrix proteins and proteases, endothelial cells can be analyzed for production of specific factors involved in solid tumor growth support (such as neo-vascularization), and different subsets of tumor cells from a solid tumor can be isolated and analyzed for tumorigenicity, drug resistance and metastatic potential.

"Enriched", as in an enriched population of cells, can be defined based upon the increased number of cells having a particular marker in a fractionated set of cells as compared with the number of cells having the marker in the unfractionated set of cells. However, the term "enriched" can be preferably defined by tumorigenic function as the minimum number of cells that form tumors at limit dilution frequency in test mice. Thus, if 500 tumor stem cells form tumors in 63% of test animals, but 5000 unfractionated tumor cells are required to form tumors in 63% of test animals, then the solid tumor stem cell population is 10-fold enriched for tumorigenic activity (see, EXAMPLES). The solid tumor stem cell model (FIG. 1A) provides the linkage between these two definitions of (phenotypic and functional) enrichment.

FACS methods using CD44 alone can enrich solid tumor stem cells at least 2-fold (see, EXAMPLE 1 and 3). FACS methods using B38.1 and CD24 can enrich for solid tumor stem cells 5-6 fold (see, EXAMPLE 3). Enrichment using additional markers can enrich 10-fold or more and can be used to isolate solid tumor stem cells.

"Isolated" refers to a cell that is removed from its natural environment (such as in a solid tumor) and that is isolated or separated, and is at least about 75% free, and most preferably about 90% free, from other cells with which it is naturally present, but which lack the marker based on which the cells were isolated.

Purification (enrichment or isolation) of subsets of cancer cells from a solid tumor allows one of skill in the art of oncology to distinguish between classic models of cancers and the solid tumor stem cell model (FIG. 1). If indeed a minority of solid tumor cells has stem cell properties, then to efficiently identify the genes necessary for tumor proliferation and drug resistance, the genomics must be focused on the stem cell population. If however, the genomics is targeted to the bulk population rather than the solid tumor stem cells, then the most promising drug targets are obscured or lost in a sea of other genes expressed by the other cells within a tumor that do not have the capacity for extensive proliferation.

In some of the EXAMPLES, we focused on the tumorigenic cells from breast cancer. Focusing on the individual populations of cells within a solid tumor provides a clearer understanding of how to focus new cancer treatments and identify novel targets for drug discovery. In addition, purifying solid tumor stem (such as breast cancer tumorigenic) cells provides a material for screening for drug sensitivity and identifying markers that predict tumorigenicity or metastatic potential.

In vivo proliferation of solid tumor stem cells. The in vivo proliferation of solid tumor stem cells can be accomplished by injection of solid tumor stem cells into animals, preferably mammals, more preferably in rodents such as mice (due to the predictable methods that have been developed in the art for injection into laboratory rodents), and most preferably into immunocompromised mice, such as SCID mice, Beige/SCID mice or NOD/SCID mice (see, EXAMPLES). NOD/SCID mice are injected with the varying number of cells and observed for tumor formation. The injection can be by any method known in the art, following the enrichment of the injected population of cells for solid tumor stem cells.

In one particular embodiment, to establish human breast cancer tumors in the NOD/SCID mouse model, eight week old female NOD-SCID mice were anesthetized by an intraperitoneal injection of 0.2 ml Ketamine/Xylazine (300 mg Ketamine combined with 20 mg Xylazine in a 4 ml volume. Then, 0.02 ml of the solution was diluted in HBSS is used per 20 g mouse. Mice were then treated with VP-16 (etoposide) via an intraperitoneal injection (30 mg etoposide per 1 kg, diluted in serum-free HBSS for a final injection volume of 0.2 ml). At the same time, estrogen pellets were placed subcutaneously on the back of the necks of the mice using a trocar. The mice were then warmed and placed back in to the cages after they awoke. All tumor injections/implantations were done 3-5 days after this procedure.

For the implantation of fresh specimens, samples of human breast tumors were received within an hour after the surgeries. These tumors were cut up with scissors into small pieces, and the pieces were then minced with a blade to yield 2×2 mm-size pieces. Mincing was done in sterile RPMI 1640 medium supplemented with 20% Fetal Bovine Serum under sterile conditions on ice. The tumor pieces were then washed with serum free HBSS right before implantation. A 2-mm incision was then made in the mid abdomen area, and using a trocar, one to two small tumor pieces were implanted onto the upper right and upper left mammary fat pats (right below the second nipple on both sides). A 6-0 suture was wrapped twice around the MFP-Nipple allowing it to hold the implanted pieces in place. Sutures were removed 5 days later. Nexaban was used to seal the incision and mice were weekly monitored from tumor growth.

For the injection of the pleural effusions or dissociated solid tumor cells, cells were received shortly after surgery and washed with HBSS serum-free. Cells were then suspended in serum free-RPMI/Matrigel mixture (1:1 volume) and then injected into the upper right and left mammary pads using an 18.0 needle. To do this, the desired number of cells were suspended in 0.2 ml and injected. The site of the needle injection was sealed with Nexaban to prevent any cell leakage.

For the injection of digested tumor cells, tumors from a patient (solid tumors) or grown in mice (by the methods of the invention) were cut up into small pieces and then minced completely using sterile blades. The resulting pieces were then mixed with ultra-pure Collagenase III in HBSS solution (200-250 U collagenase/ml) and allowed to incubate at 37 C for 3-4 hr, pipetting with a 10 ml pipette is done every 15-20 minutes. At the end of the incubation, cells were filtered through a 45-micron nylon mesh and washed with RPMI-20% FBS, then washed with HBSS twice. Cells to be injected were then suspended in HBSS/Matrigel mix (1:1 volume) and injected into the mammalian fat pad or subcutaneously as described above. Nexaban can be used to seal the injection site.

For analysis of the xenotransplant tumor, a solid tumor is removed from the mice and made into a single cell suspension. Cells are stained and analyzed by flow cytometry (FACS) using methods known to those skilled in the art (Morrison & Weissman, Immunity 1(8): 661-73 (1994)). The phenotype of tumorigenic cells is $CD44^+CD24^{-/lo}$ in all tumors, and $B38.1^+CD44^+CD24^{-/lo}$ in most tumors. We then do limiting dilution analysis of cells isolated by FACS based upon expression of these markers. Next, we further purify the breast cancer stem cell. Cells are stained with 7AAD (which stains dead cells), anti H2K-PE (which stains mouse cells), and combinations of antibodies against various markers that have heterogeneous expression patterns by the cancer cells including anti-B38.1, -annexin V, -Notch 4, -CD9, -CD24, -MUC1, -CD49F, -CD62P, -P-glycoprotein, -Notch 1, -520C9, -260F9 and -317G5. FACS is used to isolate viable human cells that either do or do not express one of the differentially expressed antigens. A combination of markers allows the greatest enrichment of tumorigenic cells. For the limiting dilution assays, one hundred, one thousand, ten thousand and one hundred thousand cells of each population are analyzed in vivo.

SCID mice, NOD/SCID mice or Beige/SCID mice are injected with the varying number of cells and observed for tumors. Any tumors that form are removed for pathologic examination and FACS analysis. The tests are repeated (for example, about ten times) to confirm the results. The phenotypes of the tumorigenic cells are thus determined.

Other general techniques for formulation and injection of cells may be found in Remington's Pharmaceutical Sciences, 20th ed. (Mack Publishing Co., Easton, Pa.). Suitable routes may include parenteral delivery, including intramuscular, subcutaneous (see, above), intramedullary injections, as well as intrathecal, direct intraventricular, intravenous, intraperitoneal, intranasal, or intraocular injections, just to name a few. For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

By the use of populations of cells enriched for solid tumor stem cells, the invention is an improvement over the methods of Mueller & Reisfeld, Cancer Metastasis Rev. 10: 193-200 (1991) (who used the SCID mouse, which allows disseminated growths for a number of human tumors, particularly hematologic disorders and malignant melanoma) and Sakakibara et al., Cancer J. Sci. Am. 2: 291-300 (1996) (who studied the growth and metastatic potential of surgical specimens of breast carcinomas engrafted into the large abdominal (gonadal) fat pad of severe combined immunodeficient (SCID) mice). Sakakibara et al. observed that placement of human breast tumors within the gonadal fat pad could result in tumors that grew either rapidly, slowly, or not at all. Of 48 tumors studied, 12 (25%), including one of the three lymph node-derived tumors, grew rapidly enough within some or all of the implanted mice (i.e., the tumors reached a diameter of 2-3 em within 2-6 months) to allow repeated passage.

By contrast, the injection of solid tumor stem cells can consistently result in the successful establishment of tumors, more than 75% of the time, preferably more than 80% of the time, more preferably more than 85%, more than 90%, or more than 95% of the time. We have achieved 100% successful establishment of tumors from the five tumors tested, as well as from three pleural effusions (see, EXAMPLES). Moreover, the invention provides for the advantageous' establishment of solid tumors (particularly tumors from breast tumor stem cells) in mammary fat pads, an area not accessible for establishment using the methods of Sakakibara et al., Cancer J. 2: 291-300 (1996).

In vitro proliferation of solid tumor stem cells. Cells can be obtained from solid tumor tissue by dissociation of individual cells. Tissue from a particular tumor is removed using a sterile procedure, and the cells are dissociated using any method known in the art (see, Sambrook et al., Molecular Cloning: A Laboratory Manual (Cold Spring Harbor Press, Cold Spring Harbor, N.Y., 1989); Current Protocols in Molecular Biology, Ausubel et al., eds., (Wiley Interscience, New York, 1993), and Molecular Biology LabFax, Brown, ed. (Academic Press, 1991)), including treatment with enzymes such as trypsin, collagenase and the like, or by using physical methods of dissociation such as with a blunt instrument. Methods of dissociation are optimized by testing different concentrations of enzymes and for different periods of time, to maximize cell viability, retention of cell surface markers, and the ability to survive in culture (Worthington Enzyme Manual, Von Worthington, ed. (Worthington Biochemical Corporation, 2000). Dissociated cells are centrifuged at low speed, between 200 and 2000 rpm, usually about 1000 rpm (210 g), and then resuspended in culture medium. For guidance to methods for cell culture, see Spector et al., Cells: A Laboratory Manual (Cold Spring Harbor Press, Cold Spring Harbor, N.Y., 1998).

The dissociated tumor cells can be placed into any known culture medium capable of supporting cell growth, including HEM, DMEM, RPMI, F-12, and the like, containing supplements which are required for cellular metabolism such as glutamine and other amino acids, vitamins, minerals and useful proteins such as transferrin and the like. Medium may also contain antibiotics to prevent contamination with yeast, bacteria and fungi such as penicillin, streptomycin, gentamicin and the like. In some cases, the medium may contain serum derived from bovine, equine, chicken and the like. However, a preferred embodiment for proliferation of solid tumor stem cells is to use a defined, low-serum culture medium. A preferred culture medium for solid tumor stem cells is a defined culture medium comprising a mixture of Ham's F12, 2% fetal calf serum, and a defined hormone and salt mixture, either insulin, transferrin, and selenium or B27 supplement. Brewer et al., J. Neuroscience Res. 35: 567 (1993).

The culture medium can be a chemically defined medium that is supplemented with fetal bovine serum or chick embryo extract (CEE) as a source of mitogens and survival factors to allow the growth of tumor stem cells in culture. Other serum-free culture medium containing one or more predetermined growth factors effective for inducing stem cell proliferation, such as N2 supplement or B27 supplement, known to those of skill in the art can be used to isolate and propagate solid tumor stem cells from other bird and mammalian species, such as human. See, U.S. Pat. Nos. 5,750,376, 5,851,832, and 5,753, 506; Atlas et al., Handbook of Microbiological Media (CRC Press, Boca, Raton, La., 1993); Freshney, Cutler on Animal Cells, A Manual of Basic Technique, 3d Edition (Wiley-Liss, New York, 1994), all incorporated herein by reference.

The culture medium for the proliferation of solid tumor stem cells thus supports the growth of solid tumor stem cells and the proliferated progeny. The "proliferated progeny" are undifferentiated tumor cells, including solid tumor stem cells, since solid tumor stem cells have a capability for extensive proliferation in culture.

Conditions for culturing should be close to physiological conditions. The pH of the culture medium should be close to physiological pH, preferably between pH 6-8, more preferably between about pH 7 to 7.8, with pH 7.4 being most preferred. Physiological temperatures range between about 30° C. to 40° C. Cells are preferably cultured at temperatures between about 32° C. to about 38° C., and more preferably between about 35° C. to about 37° C. Similarly, cells may be cultured in levels of $O_2$ that are comparatively reduced relative to $O_2$ concentrations in air, such that the $O_2$ concentration is comparable to physiological levels (1-6%), rather than 20% $O_2$ in air.

A particular patient's solid tumor stem cells, once they have been proliferated in vitro, can be analyzed and screened. Solid tumor stem cell proliferated in vitro can also be genetically modified using techniques known in the art (see, below; see also, Sambrook et al., Molecular Cloning: A Laboratory Manual (Cold Spring Harbor Press, Cold Spring Harbor, N.Y., 1989); Current Protocols in Molecular Biology, Ausubel et al., eds., (Wiley Interscience, New York, 1993)). The in vitro genetic modification may be more desirable in certain circumstances than in vivo genetic modification techniques when more control over the infection with the genetic material is required.

Solid tumor stem cells and stem cell progeny can be cryopreserved until they are needed by any method known in the art. The cells can be suspended in an isotonic solution, preferably a cell culture medium, containing a particular cryopreservant. Such cryopreservants include dimethyl sulfoxide (DMSO), glycerol and the like. These cryopreservants are used at a concentration of 5-15%, preferably 8-10%. Cells are frozen gradually to a temperature of −10° C. to −ISO° C., preferably −20° C. to −100° C., and more preferably −ISO° C.

Additional guidance for the in vitro culture of solid tumor stem cells is provided in EXAMPLE 9 and FIG. 9.

Genetic modification of solid tumor stem cells and solid tumor stem cell progeny. In the undifferentiated state, the solid tumor stem cells rapidly divide and are therefore excellent targets for genetic modification. The term "genetic modification" as used herein refers to the stable or transient alteration of the genotype of a precursor cell by intentional introduction of exogenous DNA. DNA may be synthetic, or naturally derived, and may contain genes, portions of genes, or other useful DNA sequences. The term "genetic modification" as used herein is not meant to include naturally occurring alterations such as that which occurs through natural viral activity, natural genetic recombination, or the like. General methods for the genetic modification of eukaryotic cells are known in the art. See, Sambrook et al., Molecular Cloning: A Laboratory Manual (Cold Spring Harbor Press, Cold Spring Harbor, N.Y., 1989); Current Protocols in Molecular Biology, Ausubel et al., eds., (Wiley Interscience, New York, 1993).

Many methods for introducing vectors into cells or tissues are available and equally suitable for use with solid tumor stem cells in vivo, in vitro, and ex vivo. Vectors may be introduced into hematopoietic stem cells taken from the patient and clonally propagated. By the method of the invention, such methods are extended to solid tumor stem cells.

"Transformation" or "genetically modified" as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

Genetic manipulation of primary tumor cells has been described previously by Patel et al., Human Gene Therapy 5: 577-584 (1994). Genetic modification of a cell may be accomplished using one or more techniques well known in the gene therapy field. Mulligan R C, Human Gene Therapy 5: 543-563 (1993). Viral transduction methods may comprise the use of a recombinant DNA or an RNA virus comprising a nucleic acid sequence that drives or inhibits expression of a protein to infect a target cell. A suitable DNA virus for use in the present invention includes but is not limited to an adenovirus (Ad), adeno-associated virus (AAV), herpes virus, vaccinia virus or a polio virus. A suitable RNA virus for use in the present invention includes but is not limited to a retrovirus or Sindbis virus. Several such DNA and RNA viruses exist that may be suitable for use in the present invention.

Adenoviral vectors have proven especially useful for gene transfer into eukaryotic cells for vaccine development (Graham F L & Prevec L, In Vaccines: New Approaches to Immunological Problems, Ellis RV ed., 363-390 (Butterworth-Heinemann, Boston, 1992).

Specific guidance for the genetic modification of solid tumor stem cells is provides in EXAMPLE 13 and in FIGS. 15-18.

"Non-viral" delivery techniques that have been used or proposed for gene therapy include DNA-ligand complexes, adenovirus-ligand-DNA complexes, direct injection of DNA, CaP04 precipitation, gene gun techniques, electroporation, and lipofection. Mulligan R C, Science 260: 926-932 (1993). Any of these methods are widely available to one skilled in the art and would be suitable for use in the present invention. Other suitable methods are available to one skilled in the art, and it is to be understood that the present invention may be accomplished using any of the available methods of transfection. Lipofection may be accomplished by encapsulating an isolated DNA molecule within a liposomal particle and contacting the liposomal particle with the cell membrane of the target cell. Liposomes are self-assembling, colloidal particles in which a lipid bilayer, composed of amphiphilic molecules such as phosphatidyl serine or phosphatidyl choline, encapsulates a portion of the surrounding media such that the lipid bilayer surrounds a hydrophilic interior. Unilammellar or multilammellar liposomes can be constructed such that the interior contains a desired chemical, drug, or, as in the instant invention, an isolated DNA molecule. Delivery by transfection, by liposome injections, or by polycationic amino polymers may be achieved using methods which are well known in the art (see, e.g., Goldman, C. K. et al. Nature Biotechnology 15:462-466 (1997)).

Two types of modified solid tumor stem cells of particular interest are deletion mutants and over-expression mutants. Deletion mutants are wild-type cells that have been modified genetically so that a single gene, usually a protein-coding gene, is substantially deleted. Deletion mutants also include mutants in which a gene has been disrupted so that usually no detectable mRNA or bioactive protein is expressed from the gene, even though some portion of the genetic material may be present. In addition, in some embodiments, mutants with a deletion or mutation that removes or inactivates one activity of a protein (often corresponding to a protein domain) that has two or more activities, are used and are encompassed in the term "deletion mutants." Over-expression mutants are wild-type cells that are modified genetically so that at least one gene, most often only one, in the modified solid tumor stem cell is expressed at a higher level as compared to a cell in which the gene is not modified.

Genetically modified solid tumor stem cells can be subjected to tissue culture protocols known in the art (see, U.S. Pat. Nos. 5,750,376 and 5,851,832, Spector et al., Cells: A Laboratory Manual (Cold Spring Harbor Press, Cold Spring Harbor, N.Y., 1998)). Tumor stem cells can be genetically modified in culture to promote differentiation, cell death, or immunogenicity. For example, tumor stem cells can be modified to enhance expression of products that direct an immune response against the patient's solid tumor. Alternatively, the solid tumor stem cells can be subjected to various proliferation protocols in vitro prior to genetic modification. The protocol used depends upon the type of genetically modified solid tumor stem cell or solid tumor stem cell progeny desired. Once the cells have been subjected to the differentiation protocol, they are again assayed for expression of the desired protein. Cells having the desired phenotype can be isolated and implanted into recipients in need of the protein or biologically active molecule that is expressed by the genetically modified cell. Such molecules can enhance tumor regression or inhibit tumor spread.

In vitro models of solid tumor development, in vivo models, and methods for screening effects of drugs on solid tumor stem cells. Solid tumor stem cells and solid tumor stem cell progeny cultured in vitro (see, EXAMPLE 9) or in vivo (in the xenograft model of the invention) can be used for the screening of potential therapeutic compositions. These compositions for the treatment of solid tumors can be applied to these cells in culture at varying dosages, and the response of these cells monitored for various time periods. Physical characteristics of these cells can be analyzed by observing cells by microscopy. The induction of expression of new or increased levels of proteins such as enzymes, receptors and other cell surface molecules can be analyzed with any technique known in the art see, Clarke et al.) Proc. Natl. Acad. Sci. USA 92: 11024-11028 (1995)) which can identify the alteration of the level of such molecules. These techniques include immuno-histochemistry, using antibodies (see, EXAMPLES) against such molecules, or biochemical analysis. Such biochemical analysis includes protein assays, enzymatic assays, receptor binding assays, enzyme-linked immunosorbant assays (ELISA), electrophoretic analysis, analysis with high performance liquid chromatography (HPLC), Western blots, and radioimmune assays (RIA). Nucleic acid analysis such as Northern blots can be used to examine the levels of mRNA coding for these molecules or PCR (see, EXAMPLE 14).

Alternatively, such cells treated with these pharmaceutical compositions can be transplanted into an animal (such as in the xenograft model of the invention), and their survival, ability to form tumors, and biochemical and immunological characteristics examined.

The solid stem cells and solid stem cell progeny of the invention can be used in methods of determining the effect of biological agents on solid tumor cells. The term "biological agent" or "test compound" refers to any agent (including a virus, protein, peptide, amino acid, lipid, carbohydrate, nucleic acid, nucleotide, drug, antibody, prodrug or other substance) that may have an effect on tumor cells whether such effect is harmful, beneficial, or otherwise.

To determine the effect of a potential test compound on solid tumor stem cells, a culture of precursor cells derived from tumor stem cells can be obtained from tissue of a subject, such as a patient with a tumor or other cancerous disease, such as an epithelial cancer or breast cancer. Once the solid tumor stem cells or other desired populations of cells are obtained from the subject, the cells are cultured in vitro. The choice of culture depends upon the particular test compound being tested and the diagnostic effects that the laboratory personnel want to achieve.

The ability of various biological agents to increase, decrease, or modify in some other way the number and nature of the solid tumor stem cells and solid tumor stem cell progeny can be screened. For example, it is possible to screen for test compounds that decrease the proliferative ability of the solid tumor stem cells, which would be useful for identifying anti-cancer therapeutic agents. In these assays, the relevant cells are cultured in the presence of the test compounds of interest and assayed for the degree of proliferation or cell death that occurs.

The effects of a test compound or combination of test compounds on the extensive proliferation of solid tumor stem cells and their progeny can be determined. It is possible to screen non-tumorigenic solid tumor cells that have already been induced to lose the ability to extensively proliferate before the screening. It is also possible to determine the effects of the test compounds on the proliferation process by applying them to solid tumor stem cells. Generally, the test compound is solubilized and added to the culture medium or to the mouse in the in vivo assay at varying concentrations to determine the effect of the test compounds or agent at each dose. The culture medium may be replenished with the test compound or biological agent every couple of days in amounts so as to keep the concentration of the agent somewhat constant. Similarly, the test compound can be re-administered to the mouse at different intervals to assess the effect of the compound over time.

Changes in proliferation are observed by an increase or decrease in the number of cells that form or an increase or decrease in the size of the foci in vitro, or tumor size in vivo (which is a reflection of the rate of proliferation and the rate of cell death—determined by the numbers of cells per foci or tumor size in the mouse). The effect of the test compound on tumor stem cells are measured by determining the number of tumor stem cells that persist in culture or in the tumors in vivo after treatment with the test compound. In addition to determining the number of tumor stem cells, the effects of the test compound on tumor stem cell cell-cycle status, and marker expression are also determined by flow-cytometry.

The test compounds or biological agents added to the culture medium or injected into the mouse can be at a final concentration in the range of about 10 pg/ml to 1 µg/ml, preferably about 1 ng/ml (or 1 ng/cc of blood) to 100 ng/ml (or 100 ng/cc of blood).

The effects of the test compounds or biological agents are identified on the basis of significant difference relative to control cultures with respect to criteria such as the ratios of expressed phenotypes, cell viability, proliferation rate, number of tumor stem cells, tumor stem cell activity upon transplantation in vivo, tumor stem cell activity upon transplantation in culture, cell cycle distribution of tumor cells, and alterations in gene expression.

Therapeutic compositions and methods. A pharmaceutical composition containing a Notch ligand, an anti-Notch antibody, or other therapeutic agent that acts as an agonist or antagonist of proteins in the Notch signal transduction/response pathway can be administered by any effective method. For example, a physiologically appropriate solution containing an effective concentration of anti-Notch therapeutic agent can be administered topically, intraocularly, parenterally, orally, intranasally, intravenously, intramuscularly, subcutaneously or by any other effective means. In particular, the anti-Notch therapeutic agent may be directly injected into a target cancer or tumor tissue by a needle in amounts effective to treat the tumor cells of the target tissue. Alternatively, a cancer or tumor present in a body cavity such as in the eye, gastrointestinal tract, genitourinary tract (e.g., the urinary bladder), pulmonary and bronchial system and the like can receive a physiologically appropriate composition (e.g., a solution such as a saline or phosphate buffer, a suspension, or an emulsion, which is sterile) containing an effective concentration of anti-Notch therapeutic agent via direct injection with a needle or via a catheter or other delivery tube placed into the cancer or tumor afflicted hollow organ. Any effective imaging device such as X-ray, sonogram, or fiber-optic visualization system may be used to locate the target tissue and guide the needle or catheter tube. In another alternative, a physiologically appropriate solution containing an effective concentration of anti-Notch therapeutic agent can be administered systemically into the blood circulation to treat a cancer or tumor that cannot be directly reached or anatomically isolated.

All such manipulations have in common the goal of placing the anti-Notch therapeutic agent in sufficient contact with the target tumor to permit the anti-Notch therapeutic agent to contact, transduce or transfect the tumor cells (depending on the nature of the agent). In one embodiment, solid tumors present in the epithelial linings of hollow organs may be treated by infusing the vector suspension into a hollow fluid filled organ, or by spraying or misting into a hollow air filled organ. Thus, the tumor cells (such as a solid tumor stem cells) may be present in or among the epithelial tissue in the lining of pulmonary bronchial tree, the lining of the gastrointestinal tract, the lining of the female reproductive tract, genitourinary tract, bladder, the gall bladder and any other organ tissue accessible to contact with the anti-Notch therapeutic agent. In another embodiment, the solid tumor may be located in or on the lining of the central nervous system, such as, for example, the spinal cord, spinal roots or brain, so that anti-Notch therapeutic agent infused in the cerebrospinal fluid contacts and transduces the cells of the solid tumor in that space. (Accordingly, the anti-Notch therapeutic agent can be modified to cross the blood brain barrier using method known in the art). One skilled in the art of oncology can appreciate that the anti-Notch therapeutic agent can be administered to the solid tumor by direct injection of the vector suspension into the tumor so that anti-Notch therapeutic agent contacts and affects the tumor cells inside the tumor.

One skilled in the art of oncology can understand that the vector is administered in a composition comprising the vector together with a carrier or vehicle suitable for maintaining the transduction or transfection efficiency of the chosen vector and promoting a safe infusion. Such a carrier may be a pH balanced physiological buffer, such as a phosphate, citrate or bicarbonate buffers a saline solution, a slow release composition and any other substance useful for safely and effectively placing the anti-Notch therapeutic agent in contact with solid tumor stem cells to be treated.

In treating a cancer patient who has a solid tumor, a therapeutically effective amount of an anti-Notch therapeutic agent is administered. A therapeutically effective dose refers to that amount of the compound sufficient to result in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ as determined in cell culture. Such information can be used to more accurately determine useful doses in humans. Levels in plasma may be measured, for example, by high performance liquid chromatography (HPLC).

The exact formulation, route of administration and dosage can be chosen by the individual physician in view of the patient's condition (see e.g. Fingl et al., In The Pharmacological Basis of Therapeutics, Ch. 1, pg. 1 (1975)). The attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the clinical disorder of interest can vary with the severity of the condition to be treated and the route of administration. See, Merck Index: An Encyclopedia of Chemicals, Drugs and Biologicals, 12 Edition (CRC Press 1996); Physicians' Desk Reference 55th Edition (2000)). The severity of the condition may, for example, be evaluated, in part, by appropriate prognostic evaluation methods. Further, the dose and perhaps dose frequency, also vary according to the age, body weight, and response of the individual patient. A program comparable to that discussed above may be used in veterinary medicine.

Depending on the specific conditions being treated, agents may be formulated and administered systemically or locally. Techniques for formulation and administration may be found in Remington's Pharmaceutical Sciences, 20th ed. (Mack Publishing Co., Easton, Pa.). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

In addition to the active ingredients, these pharmaceutical compositions may contain suitable pharmaceutically acceptable carriers comprising excipients and auxiliaries, which facilitate processing of the active compounds into preparations which can be used pharmaceutically. The preparations formulated for oral administration may be in the form of tablets, capsules, or solutions. The pharmaceutical compositions of the present invention may be manufactured in a manner that is itself known, e.g., by means of conventional mixing, dissolving, granulating, levigating, emulsifying, encapsulating, entrapping or lyophilizing processes. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Polynucleotides and polypeptides obtained from solid tumor stem cells. "Polynucleotide" refers to chain of nucleotides, which can be a nucleic acid, nucleic acid sequence, oligonucleotide, nucleotide or any fragment thereof. It may be DNA or RNA of genomic DNA. mRNA, cDNA, or synthetic origin, double-stranded or single-stranded and combined with carbohydrate, lipids, protein or other materials to perform a particular activity or form a useful composition. "Oligonucleotide" is substantially equivalent to the terms amplimer, primer, oligomer, element, and probe. The term "probe" refers to a polynucleotide sequence capable of hybridizing with a target sequence to form a polynucleotide probe/target complex. A "target polynucleotide" refers to a chain of nucleotides to which a polynucleotide probe can hybridize by base pairing. In some instances, the sequences will be complementary (no mismatches) when aligned. In other instances, there may be up to a 10% mismatch.

DNA or RNA can be isolated from the sample according to any of a number of methods well known to those of skill in the art. For example, methods of purification of nucleic acids are described in Tijssen, Laboratory Techniques in Biochemistry and Molecular Biology: Hybridization With Nucleic Acid Probes, Part 1. Theory and Nucleic Acid Preparation (Elsevier. New York N.Y. 1993). "Sample" is used in its broadest sense. A sample containing polynucleotides or polypeptides can be a bodily fluid; an extract from a cell, chromosome, organelle or membrane isolated from a cell; genomic DNA, RNA or cDNA in solution or bound to a substrate; a cell; a tissue; a tissue print; and the like.

Total RNA can be isolated using the TRIZOL reagent (Life Technologies, Gaithersburg Md. USA), and mRNA is isolated using oligo d(T) column chromatography or glass beads. Alternatively, when target polynucleotides are derived from an mRNA, the target polynucleotides can be a cDNA reverse transcribed from an mRNA, an RNA transcribed from that cDNA, a DNA amplified from that cDNA, an RNA transcribed from the amplified DNA and the like. When the target polynucleotide is derived from DNA, the target polynucleotide can be DNA amplified from DNA or RNA reverse transcribed from DNA.

Several technologies produce pools of restriction fragments of limited complexity for electrophoretic analysis, such as methods combining double restriction enzyme digestion with phasing primers (see, e.g., European patent application EP 0 534 858 A1), or methods selecting restriction fragments with sites closest to a defined mRNA end (see, e.g. Prashar et al., Proc. Natl. Acad. Sci. USA 93: 659-663 (1996)). Other methods statistically sample cDNA pools, such as by sequencing sufficient bases (in each of, multiple cDNAs to identify each cDNA or by sequencing short tags which are generated at known positions relative to a defined mRNA end (see, e.g., Velculescu, Science 270: 484-487 (1995)).

Methods of modifying RNA abundances and activities currently fall within three classes, ribozymes, antisense species (PCT patent application WO 88/09810), and RNA aptamers (Good et al., Gene Therapy 4: 45-54 (1997)). Ribozymes are RNAs which are capable of catalyzing RNA cleavage reactions. (PCT patent application WO 90/11364). Ribozyme methods involve exposing a cell to, inducing expression in a cell, etc. of such small RNA ribozyme molecules. (Grassi & Marini, Annals of Medicine 28: 499-510 (1996); Gibson, Cancer and Metastasis Reviews 15: 287-299 (1996)).

The term "antisense," as used herein, refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

Oligonucleotides may be synthesized by standard methods known in the art, e.g. by use of an automated DNA synthesizer (such as are commercially available from Biosearch, Applied Biosystems, etc.).

"Amplification," as used herein, relates to the production of additional copies of a nucleic acid sequence. Amplification is generally carried out using polymerase chain reaction (PCR) technologies well known in the art. See, e.g., Dieffenbach C W & Dveksler G S, PCR Primer, a Laboratory Manuall-5 (Cold Spring Harbor Press, Plainview, N.Y., 1995). Amplification can be polymerase chain reaction (PCR), ligase chain reaction (LCR), nucleic acid sequence-based amplification (NASBA), or T7 based RNA amplification.

"Polypeptide" refers to an amino acid, amino acid sequence, oligopeptide, peptide, or protein or portions thereof whether naturally occurring or synthetic.

Methods for direct measurement of protein activity are well known to those of skill in the art. Such methods include, e.g., methods which depend on having an antibody ligand for the protein, such as Western blotting, see, e.g., Burnette, A. Anal. Biochem. 112: 195-203 (1981). Such methods also include enzymatic activity assays, which are available for most well-studied protein drug targets. Detection of proteins can be accomplished by antibodies (see, EXAMPLES). The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

Proteins isolated from an enriched population of solid tumor stem cells or isolated solid tumor cells can be separated by two-dimensional gel electrophoresis systems. Two-dimensional gel electrophoresis is well-known in the art and typically involves iso-electric focusing along a first dimension followed by SDS-PAGE electrophoresis along a second dimension. See, e.g., Hames et al, Gel Electrophoresis of Proteins: A Practical Approach (IRL Press, New York 1990); Lander, Science 274:536-539 (1996). The resulting electrophoretograms can be analyzed by numerous techniques, including mass spectrometric techniques, western blotting and immunoblot analysis using polyclonal and monoclonal antibodies, and internal and N-terminal micro-sequencing. Using these techniques, it is possible to identify a substantial fraction of all the proteins produced under given physiological conditions, including in cells (e.g., in solid tumor stem cells) exposed to a drug, or in cells modified by, e.g., deletion or over-expression of a specific gene.

cDNA libraries. The purified solid tumor stem cells, solid tumor stem cell progeny, non-tumorigenic cells, and unfractionated tumor cells can be used to make arrays or cDNA libraries using methods known in the art (see, Sambrook et al., Molecular Cloning: A Laboratory Manual (Cold Spring Harbor Press, Cold Spring Harbor, N.Y., 1989); Current Protocols in Molecular Biology, Ausubel et al., eds., (Wiley Interscience, New York, 1993)) to identify potential novel drug targets.

Molecular biology comprises a wide variety of techniques for the analysis of nucleic acids and proteins, many of which form the basis of clinical diagnostic assays. These techniques include nucleic acid hybridization analysis, restriction enzyme analysis, genetic sequence analysis, and separation and purification of nucleic acids and proteins (Sambrook et al., Molecular Cloning: A Laboratory Manual, Second Ed. (Cold Spring Harbor Laboratory Press, Cold Spring Harbor, N.Y., 1989). Many molecular biology techniques involve carrying out numerous operations on a large number of samples. For guidance to genomics and other molecular biological methods useful in the invention, see Birren et al., Genome Analysis: A Laboratory Manual Series, Volume 1, Analyzing DNA (Cold Spring Harbor Press, Cold Spring Harbor, N.Y., 1997); Birren et al., Genome Analysis: A Laboratory Manual Series, Volume 2, Detecting Genes (Cold Spring Harbor Press, Cold Spring Harbor, N.Y., 1998); Birren et al., Genome Analysis: A Laboratory Manual Series, Volume 4, Mapping Genomes (Cold Spring Harbor Press, Cold Spring Harbor, N.Y., 1999).

Nucleic acid hybridization analysis generally involves the detection of a very small numbers of specific target nucleic acids (DNA or RNA) with probes among a large amount of non-target nucleic acids. Multiple sample nucleic acid hybridization analysis has been conducted on a variety of filter and solid support formats. The "dot blot" hybridization, involves the non-covalent attachment of target DNAs to a filter, which are subsequently hybridized with a labeled probes. The "dot blot" hybridization has been further developed for multiple analysis (European Patent application EP 0 228 075) and for the detection of overlapping clones and the construction of genomic maps (U.S. Pat. No. 5,219,726). Another format, the so-called "sandwich" hybridization, involves attaching oligonucleotide probes covalently to a solid support and using them to capture and detect multiple nucleic acid targets (U.S. Pat. No. 4,751,177; PCT International patent application WO 90/01564). Multiplex versions of these formats are called "reverse dot blots".

Methods are known in the art for amplifying signal using sensitive reporter groups (enzyme, fluorophores, radioisotopes, etc.) and associated detection systems (fluorometers, luminometers, photon counters, scintillation counters, etc.). These methods can be combined with amplification methods, such as the polymerase chain reaction (PCR) for the amplification of target nucleic acid sequences. See, Innis et al., PCR Protocols: A Guide to Methods and Applications, (Academic Press, 1990).

Microarrays. Mimicking the in situ hybridization in some aspects, new techniques are being developed for carrying out multiple sample nucleic acid hybridization analysis on microformatted multiplex or matrix devices (e.g., DNA chips) (see, Barinaga, Science 253: 1489 (1991); Bains, Bio/Technology 10: 757-758 (1992)). Guidance for the use of microarrays is provided by Wang, E et al., Nature Biotechnology 18; 457-459 (2000); Diehn M et al., Nature Genetics 25: 58-62 (2000).

Microarrays are known in the art and consist of a surface to which probes that correspond in sequence to gene products (e.g., cDNAs, oligonucleotides, mRNAs, cRNAs polypeptides, and fragments thereof), can be specifically hybridized or bound at a known position. In one embodiment, the microarray is an array (i.e., a matrix) in which each position represents a discrete binding site for a product encoded by a gene (e.g., a protein or RNA), and in which binding sites are present for products of most or almost all of the genes in the organism's genome.

The polynucleotides, polypeptides, or analogues are attached to a solid support or substrate, which may be made from glass, plastic (e.g., polypropylene, nylon), polyacrylamide, nitrocellulose, or other materials. "Substrate" refers to any suitable rigid or semi-rigid support to which polynucleotides or polypeptides are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores. The polynucleotides can be immobilized on a substrate by any method known in the art. Preferably, the substrates are optically transparent.

A variety of methods are currently available for making arrays of biological macromolecules, such as arrays of nucleic acid molecules or proteins. One method for making ordered arrays of DNA on a porous membrane is a "dot blot" or "slot-blot" method. A more efficient technique employed for making ordered arrays of fragments uses an array of pins dipped into the wells, e.g., the 96 wells of a microtiter plate, for transferring an array of samples to a substrate, such as a porous membrane. An alternate method of creating ordered arrays of nucleic acid sequences is described by U.S. Pat. No. 5,143,854 (to Pirrung) and also by Fodor et al., Science 251: 767-773 (1991). The method involves synthesizing different nucleic acid sequences at different discrete regions of a support. Khrapko et al., DNA Sequence 1:375-388 (1991) describes a method of making an oligonucleotide matrix by spotting DNA onto a thin layer of polyacrylamide, manually with a micropipette. U.S. Pat. No. 5,807,522 (to Brown et al., incorporated by reference) describes methods for fabricating microarrays of biological samples by dispensing a known volume of a reagent at each selected array position, by tapping a capillary dispenser on the support under conditions effective to draw a defined volume of liquid onto the support.

Spotters can use pin, ink jet, and other technologies to deposit samples onto the support material. Several of the more common methods utilize metal pins, which can be either solid or split. When the pins are dipped into wells that contain the compounds of interest, each picks up a small amount of the material. The pin is then brought into contact with the solid support and a nanoliter volume is dispensed at the desired location. In split pins (otherwise known as quills) a slot cut into the head of the pin functions as a reservoir for the compound being spotted. Quill pins are most often used with glass slides, while solid pins are typically used for spotting membranes. Amersham Pharmacia Biotech, GeneMachines, and other companies offer spotting robots.

Ink-jet technology provides another method of spotting microarrays. Adapted from the printer industry and redesigned for use in biotechnological applications, this uses piezoelectric crystal oscillators and an electrode guidance system to deposit the compound in a precise location on the slide or membrane. Companies such as Cartesian Technologies and ProtoGene Laboratories use this technology.

A method for attaching the nucleic acids to a surface is by printing on glass plates, as is described generally by PCT publication WO 95/35505; DeRisi et al., Nature Genetics 14:457-460 (1996); Shalon et al., Genome Res. 6:639-645 (1996); and Schena et al., Proc. Natl. Acad. Sci. USA 93: 10614-10619 (1995). Another method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., Science 251: 767-773 (1991); Pease et al., Proc. Natl. Acad. Sci. USA 91:5022-5026 (1994); Lockhart et al., Nature Biotech 14:1675 (1996); U.S. Pat. Nos. 5,578,832; 5,556,752; and 5,510,270, each of which is incorporated by reference).

U.S. Pat. No. 6,110,426 (to Shalon et al.) a method and apparatus for fabricating microarrays of biological samples for large scale screening assays, such as arrays of DNA samples to be used in DNA hybridization assays for genetic research and diagnostic applications. U.S. Pat. No. 6,221,674 (to Sluka et al.) discloses a process is described for applying spatially defined reagent areas to a solid phase which is characterized in that a liquid containing an adsorptive binding reagent is contacted with spatially defined areas of a solid phase which comprises an essentially continuous metal or metal oxide surface for an adequate time period to enable the formation of adsorptive bonds between the binding reagent and the solid phase. A process is described in PCT application WO 92/1 0092 which can be used to generate a plurality of different structures on a glass support by means of photoreactive compounds and irradiation using masks. A process is described in U.S. Pat. No. 4,877,745 in which differently functionalized spots can be applied to plastic supports by means of ink-jet.

Among the vendors of microarrays and microarray technology useage are Affymetrix, Inc. (USA), NimbleGen Systems, Inc. (Madison, Wis., USA), and Incyte Genomics (USA) (producing microarrays for core facilities in large industrial and academic departments); Agilent Technologies (USA) and Graffinity Pharmaceutical Design, GmbH (Germany) (which provide specific services such as printing and fingerprinting arrays designed and used by individual researchers); and CLONTECH Laboratories (Becton Dickinson Bioscience) and BioRobotics, Ltd. (Great Britain) (which provide the basic tools necessary for individual researchers to carry out the entire process of producing microarrays, including printing). See, Gwynne P & Heebner G, "DNA Chips and Microarrays" Science (2001).

In contrast to plastic surfaces, metal and metal oxide surfaces have the advantage that they can be coated with an exactly defined matrix layer by self-assembly techniques. A self-assembled monolayer (SAM) is formed for example when organic alkylthiols are absorbed onto a gold surface, the spontaneous organization of such a densely packed monolayer being based on strong specific interactions between the support material and the adsorbent. Nuzzo et al., J. Am. Chem. Soc. 105: 4481 (1983). In this manner it is possible to apply an exactly defined monolayer of a binding matrix to the surface of metals such as e.g. gold or silver. Furthermore the specific binding capability of self-assembled solid phases can be further optimized by dilution of the specific solid phase reactants as described in EP-A-O 515 615.

The coating of metal surfaces with microstructures based on self-assembled monolayers is also known and can be used to attach components isolated from solid tumor stem cells. Whitesides et al., Langmuir 10 (1994) 1498-1511 describe a process in which reagents are stamped onto a noble metal surface by means of a special microstructured silicone stamp. This enables microstructured monolayers to be generated with zones that are spatially separated from one another. Microstructures of self-assembled monolayers on noble metal surfaces can be formed by irradiation through masks of substrates whose whole area is covered with thiols and subsequent washing. Hemminger et al., Langmuir 10: 626-628 (1994). Spatially separate zones are also formed in this process which are all identically functionalized. A further possibility of producing reagent spots is firstly to apply gold spots to a support that are already spatially separated from one another which are then subsequently coated with reagents.

The binding of analytes to a functionalized solid phase matrix according to the invention can for example be detected by confocal scanner fluorescence microscopy or by plasmon resonance spectroscopy. Ruthenhausler B et al., Nature, 332: 615-617 (1988).

U.S. Pat. No. 6,228,659 describes an apparatus for producing a plurality of arrays of reagent regions is disclosed. A dispensing assembly in the apparatus has a plurality of heads which are spaced for depositing reagents at selected positions in different array areas in a substrate.

Transcript arrays can be employed for analyzing the transcriptional state in a cell, and especially for measuring the transcriptional states of cells exposed to graded levels of a therapy of interest such as graded levels of a drug of interest or to graded levels of a disease state of interest. In one embodiment, transcript arrays are produced by hybridizing detectably labeled polynucleotides representing the mRNA transcripts present in a cell (e.g., fluorescently labeled cDNA synthesized from total cell mRNA) to a microarray. In alternative embodiments, the cDNA or RNA probe can be synthesized in the absence of detectable label and may be labeled subsequently, e.g., by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent. The label for the probe may be selected from the group consisting of biotin, fluorescent, radioactive, and enzymatic labels. When fluorescently-labeled probes are used, many suitable fluorophores are known, including fluorescein, lissamine, phycoerythrin, rhodamine (perkin Elmer Cetus), Cy2, Cy3, Cy3.5, Cy5, Cy5.5, Cy7, Fluor X (Amersham) and others (see, e.g., Kricka, Nonisotopic DNA Probe Techniques (Academic Press San Diego, Calif., 1992). It will be appreciated that pairs of fluorophores are chosen that have distinct emission spectra so that they can be easily distinguished. In another embodiment, a label other than a fluorescent label is used. For example, a radioactive label, or a pair of radioactive labels with distinct emission spectra, can be used (see Zhao et al., Gene 156:207 (1995); Pietu et al., Genome Res. 6:492 (1996); see also, EXAMPLE 21). For example, $^{32}P$ can be used.

These methods of attaching transcripts usually attach specific polynucleotide sequences to very small specific areas of a solid support, such as micro-wells of a DNA chip. These hybridization formats are micro-scale versions of the conventional "reverse dot blot" and "sandwich" hybridization systems. The micro-formatted hybridization can be used to carry out "sequencing by hybridization" (see, Baringa, Science 253: 1489 (1991); Bains, Bio/Technology 10: 757-758 (1992). Sequencing by hybridization makes use of all possible n-nucleotide oligomers (n-mers) to identify n-mers in an unknown DNA sample, which are subsequently aligned by algorithm analysis to produce the DNA sequence (see, U.S. Pat. No. 5,202,231; see also, United Kingdom patent application GB 8810400 (1988); Southern et al., Genomics 13: 1008 (1992); Fodor et al., Nature 364: 555-556 (1993); Fodor et al., Science 251: 767-773 (1991); U.S. Pat. No. 5,143,854.

Probes can be synthesized, in whole or in part, on the surface of a substrate using a chemical coupling procedure and a piezoelectric printing apparatus, such as that described in PCT publication WO 95/251116 (Baldeschweiler et al.). Alternatively, the probe can be synthesized on a substrate surface using a self-addressable electronic device that controls when reagents are added (U.S. Pat. No. 5,605,662).

Furthermore, the probes do not have to be directly bound to the substrate, but rather can be bound to the substrate through a linker group. The linker groups are typically about 6 to 50 atoms long to provide exposure to the attached polynucleotide probe. Preferred linker groups include ethylene glycol oligomers, diamines, diacids and the like. Reactive groups on the substrate surface react with one of the terminal portions of the linker to bind the linker to the substrate. The other terminal portion of the linker is then functionalized for binding the polynucleotide probe.

Devices and computer systems for forming and using arrays of materials on a chip or substrate are known. For example, PCT International patent applications WO 92/10588 and WO 95/11995, both incorporated herein by reference, describe techniques for sequencing or sequence checking nucleic acids and other materials. Arrays for performing these operations can be formed in arrays according to the methods of, for example, the pioneering techniques disclosed in U.S. Pat. Nos. 5,445,934, 5,384,261 and 5,571,639, each incorporated herein by reference. Improved methods of forming high-density arrays of peptides, polynucleotides, and other polymer sequences in a short period of time have been devised using combinatorial solid phase synthesis. Very Large Scale Immobilized Polymer Synthesis (VLSIPS) technology has greatly advanced combinatorial solid phase polymer synthesis and paved the way to clinical application of deoxyribonucleic acid (DNA) array chips such as those sold under the name GENECHIP™ Kozal et al., Nature Medicine 2: 753-759 (1996). VLSIPS technology is disclosed in U.S. Pat. No. 5,143,854, PCT International patent applications WO 90/15070, WO 92/110092, and WO 95/11995; and Fodor et al., Science 251: 767-777 (1991).

Nucleic acid hybridization and wash conditions are chosen so that the probe "specifically binds" or "specifically hybridizes" to a specific array site, i.e., the probe hybridizes, duplexes or binds to a sequence array site with a complementary nucleic acid sequence but does not hybridize to a site with a non-complementary nucleic acid sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can easily be demonstrated that specific hybridization conditions result in specific hybridization by carrying out a hybridization assay including negative controls. Optimal hybridization conditions will depend on the length (e.g., oligomer versus polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Ausubel et al., Current Protocols in Molecular Biology (Greene Publishing and Wiley-Interscience, New York 1987). Useful hybridization conditions are also provided in, e.g., Tijessen, Hybridization With Nucleic Acid Probes, (Elsevier Science Publishers B.V., 1993) and Kricka, Nonisotopic DNA Probe Techniques, (Academic Press, San Diego, Calif., 1992).

When cDNA complementary to the RNA of a cell is made and hybridized to a microarray under suitable hybridization conditions, the level of hybridization to the site in the array corresponding to any particular gene will reflect the prevalence in the cell of RNA transcribed from that gene. For example, when detectably labeled (e.g., with a fluorophore) cDNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal.

U.S. Pat. No. 6,183,968 (to Bandman et al;) discloses polynucleotide probes that can be used as hybridizable array elements in a microarray, each of the polynucleotide probes having at least a portion of a gene which encodes a protein associated with cell proliferation or a receptor.

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., Genome Research 6:639-645 (1996)). Signals are recorded and, preferably, analyzed by computer, using commercially available methods. The abundance sort program of the invention described in U.S. Pat. No. 5,840,484 can be used to tabulate and sort by frequency the mRNA transcripts corresponding to each gene identified. Since some of the polynucleotide sequences are identified solely based on expression levels, it is not essential to know a priori the function of a particular gene in solid tumor stem cells.

Transcript image comparisons can be obtained by methods well known to those skilled in the art. Transcript levels and images can be obtained and compared, for example, by a differential gene expression assay based On a quantitative hybridization of arrayed DNA clones (Nguyen et al. Genomics 29:207-216 (1995), based on the serial analysis of gene expression (SAGE) technology (Velculescu et al. Science 270:484-487 (1995)), based on the polymerase chain reaction (Peng et al. Science 257:967-971 (1992), based on a differential amplification protocol (U.S. Pat. No. 5,545,522), or based on electronic analysis, such as comparative gene transcript analysis (U.S. Pat. No. 5,840,484) or the GEMTOOLS gene expression analysis program (Incyte Pharmaceuticals, Palo Alto, Calif., USA). Preferably, comparisons between two or more transcript profiles are performed electronically.

U.S. Pat. No. 6,215,894 discloses a system for scanning biochip arrays includes a unique image array identifier recorded for each array, and a computer-stored record corresponding to each identifier and containing the parameters of the experiment in the array identified by the identifier. The system further includes means for accessing a protocol library to retrieve the scanning protocols associated with the identified arrays and then scanning the arrays in accordance with the respective protocols. The resulting image maps generated by the scanners are stored in locations corresponding to the associated identifiers.

Measurement of the translational state may be performed according to several methods. For example, whole genome monitoring of protein (i.e., the "proteome,") can be carried out by constructing a microarray in which binding sites comprise immobilized, preferably monoclonal, antibodies specific to a plurality of protein species encoded by the cell genome.

Use of microarrays. The microarrays describe above can be employed in several applications including solid tumor: cancer diagnostics, prognostics and treatment regimens, drug discovery and development, toxicological and carcinogenicity studies, forensics, pharmacogenomics and the like.

In one embodiment, the microarray is used to monitor the progression of disease. Physicians can assess and catalog the differences in gene expression between healthy and cancerous tissues by analyzing changes in patterns of gene expression compared with solid tumor stem cells from the patient. Thus, cancer can be diagnosed at earlier stages before the patient is symptomatic. The invention can also be used to monitor the efficacy of treatment. For some treatments with known side effects, the microarray is employed to "fine tune" the treatment regimen. A dosage is established that causes a change in genetic expression patterns indicative of successful treatment. Expression patterns associated with undesirable side effects are avoided. This approach may be more sensitive and rapid than waiting for the patient to show inadequate improvement, or to manifest side effects, before altering the course of treatment.

Alternatively, animal models which mimic a disease, rather than patients, can be used to characterize expression profiles associated with a particular disease or condition. This gene expression data may be useful in diagnosing and monitoring the course of disease in a patient, in determining gene targets for intervention, and in testing novel treatment regimens.

Also, researchers can use the microarray to rapidly screen large numbers of candidate drug molecules, looking for ones that produce an expression profile similar to those of known therapeutic drugs, with the expectation that molecules with the same expression profile will likely have similar therapeutic effects. Thus, the invention provides the means to determine the molecular mode of action of a drug.

U.S. Pat. Nos. 6,218,122, 6,165,709, and 6,146,830 (all to Friend et al.) discloses methods for identifying targets of a drug in a cell by comparing (i) the effects of the drug on a wild-type cell, (1i) the effects on a wild-type cell of modifications to a putative target of the drug, and (iii) the effects of the drug on a wild-type cell which has had the putative target modified of the drug. In various embodiments, the effects on the cell can be determined by measuring gene expression, protein abundances, protein activities, or a combination of such measurements. In various embodiments, modifications to a putative target in the cell can be made by modifications to the genes encoding the target, modification to abundances of RNAs encoding the target, modifications to abundances of target proteins, or modifications to activities of the target proteins. The present invention provides an improvement to these methods of drug discovery by providing the tumorigenic solid tumor stem cells, for a more precise drug discovery program.

An "expression profile" comprises measurement of a plurality of cellular constituents that indicate aspects of the biological state of a cell. Such measurements may include, e.g., RNA or protein abundances or activity levels. Aspects of the biological state of a cell of a subject, for example, the transcriptional state, the translational state, or the activity state, are measured. The collection of these measurements, optionally graphically represented, is called the "diagnostic profile". Aspects of the biological state of a cell which are similar to those measured in the diagnostic profile, e.g., the transcriptional state, are measured in an analogous subject or subjects in response to a known correlated disease state or, if therapeutic efficacy is being monitored, in response to a known, correlated effect of a therapy. The collection of these measurements, optionally graphically represented, is called herein the "response profile". The response profiles are interpolated to predict response profiles for all levels of protein activity within the range of protein activity measured. In cases where therapeutic efficacy is to be monitored, the response profile may be correlated to a beneficial effect, an adverse effect, such as a toxic effect, or to both beneficial and adverse effects.

As is commonly appreciated, protein activities result from protein abundances; protein abundances result from translation of mRNA (balanced against protein degradation); and mRNA abundances result from transcription of DNA (balanced against mRNA degradation). Therefore, genetic level modifications to a cellular DNA constituent alters transcribed mRNA abundances, translated protein abundances, and ultimately protein activities. RNA level modifications similarly alter RNA abundance and protein abundances and activities. Protein level modifications alter protein abundances and activities. Finally, protein activity modifications are the most targeted modification methods. As is commonly appreciated, it is ultimately protein activities (and the activities of catalytically active RNAs) that cause cellular transformations and effects. Also, most drugs act by altering protein activities.

In one embodiment, cDNAs from two different cells (one being the solid tumor stem cells of the invention) are hybridized to the binding sites of the microarray. In the case of therapeutic efficacy (e.g., in response to drugs) one cell is exposed to a therapy and another cell of the same type is not exposed to the therapy. In the case of disease states one cell exhibits a particular level of disease state and another cell of the same type does not exhibit the disease state (or the level thereof). The cDNA derived from each of the two cell types are differently labeled so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular mRNA detected. The use of a two-color fluorescence labeling and detection scheme to define alterations in gene expression has been described, e.g., in Shena et al., Science 270:467-470 (1995). An advantage of using cDNA labeled with two different fluorophores is that a direct and internally controlled comparison of the mRNA levels corresponding to each arrayed gene in two cell states can be made, and variations due to minor differences in experimental conditions (e.g., hybridization conditions) will not affect subsequent analyses. Additional guidance is provided in EXAMPLE 21.

U.S. Pat. No. 6,194,158 (to Kroes et al.) for a diagnostic assay for cancer with a DNA chip of specific sequences for measuring expression levels of certain sequences within a cancer cell to determine whether expression is up- or down-regulated. The DNA chip comprising nucleotide sequences capable of hybridizing to one or more members of a panel of DNA sequences may be synthesized using commonly available techniques. mRNA is isolated from a normal, non-cancer cell and a cancer cell and hybridized to the DNA chip comprising one of more of the sequences from the panel. Hybridization is then detected by any of the available methods. In such a manner, sequences that are either overexpressed or underexpressed in a cancer cell as compared to a normal cell are. In a similar manner, mRNA from a cancer cell that has been contacted with a compound may be hybridized to sequences on the DNA chip to determine whether that compound affects expression of a particular sequence. The present invention provides an improvement over this method, in that the "cancer cell" from which mRNA can be isolated is the tumorigenic solid tumor stem cell of the invention.

Gene expression profiles of purified stem cells could give clues for the molecular mechanisms of stem cell behavior. Terskikh A V et al., Proc Natl Acad Sci USA 98(14): 7934-7939 (2001) analyzed hematopoietic stem cells (HSC)-enriched cells by comparison with normal tissue and mouse neurospheres (a population greatly enriched for neural progenitor cells) by comparison with terminally differentiated neural cells, using cDNA microarray techniques and in situ hybridization, thus identifying potential regulatory gene candidates. The invention provides an improved method of drug discovery over the methods of Terskikh, in that the use of the solid tumor stem cells of the invention can provide a distinct set of drug targets when compared with a patient's normal tissue (such as from the area of the solid tumor) or compared with the other populations of cells obtained from the solid tumor.

Several other methods for utilizing DNA chips are known, including the methods described in U.S. Pat. Nos. 5,744,305; 5,733,729; 5,710,000; 5,631,734; 5,599,695; 5,593,839; 5,578,832; 5,556,752; 5,770,722; 5,770,456; 5,753,788; 5,688,648; 5,753,439; 5,744,306 (all of which are incorporated by reference in their entirety). U.S. Pat. No. 5,807,522 (to Brown et al.) discloses a method to monitor early changes in a cell that correlate with levels of a disease state or therapy and which precede detectable changes in actual protein function or activity.

Moreover, microarrays of genomic DNA from solid tumor stem cells can be probed for single nucleotide polymorphisms (SNP), to localize the sites of genetic mutations that cause cells to become precancerous or tumorigenic. Guidance for such methods are available from the commercial vendors described above and may be found in general genetic method books, such as those described herein.

Vaccines. The solid tumor stem cells of the invention can be used to raise anti-cancer cell antibodies. In one embodiment, the method involves obtaining an enriched population of solid tumor stem cells or isolated solid tumor stem cells; treating the population to prevent cell replication (for example, by irradiation); and administering the treated cell to a human or animal subject in an amount effective for inducing an immune response to solid tumor stem cells. For guidance as to an effective dose of cells to be injected or orally administered; see, U.S. Pat. Nos. 6,218,166, 6,207,147, and 6,156,305, incorporated herein by reference. In another embodiment, the method involves obtaining an enriched population of solid tumor stem cells or isolated solid tumor stem cells; mixing the tumor stem cells in an in vitro culture with immune effector cells (according to immunological methods known in the art) from a human subject or host animal in which the antibody is to be raised; removing the immune effector cells from the culture; and transplanting the immune effector cells into a host animal in a dose that is effective to stimulate an immune response in the animal.

Monoclonal antibodies to solid tumor stem cells may be prepared using any technique which provides for the production of antibody molecules by continuous cell lines in culture.

These include, but are not limited to, the hybridoma technique, the human B-cell hybridoma technique, and the EBV-hybridoma technique (see, e.g., Kozbor, D. et al., J. Immunol. Methods 81:31-42 (1985); Cote R J et al. Proc. Natl. Acad. Sci. 80:2026-2030 (1983); and Cole S P et al. Mol. Cell. Bioi. 62:109-120 (1984>>.

In addition, techniques developed for the production of "chimeric antibodies," such as the splicing of mouse antibody genes to human antibody genes to obtain a molecule with appropriate antigen specificity and biological activity, can be used (see, e.g., Morrison S L et al. Proc. Natl. Acad. Sci. 81:6851-6855 (1984); Neuberger M S et al. Nature 312:604-608 (1984); and Takeda S et al. Nature 314:452-454 (1985>>.

Various immunoassays may be used for screening to identify antibodies having the desired specificity. Numerous protocols for competitive binding or immunoradiometric assays using either polyclonal or monoclonal antibodies with established specificities are well known in the art.

The antibody can also be a humanized antibody. The term "humanized antibody," as used herein, refers to antibody molecules in which the amino acid sequence in the non-antigen binding regions has been altered so that the antibody more closely resembles a human antibody, and still retains its original binding ability. Antibodies are humanized so that they are less immunogenic and therefore persist longer when administered therapeutically to a patient.

Human antibodies can be generated using the XenoMouse™ technology from Abgenix (Fremont, Calif., USA), which enables the generation and selection of high affinity, fully human antibody product candidates to essentially any disease target appropriate for antibody therapy. See, U.S. Pat. Nos. 6,235,883, 6,207,418, 6,162,963, 6,150,584, 6,130,364, 6,114,598, 6,091,001, 6,075,181, 5,998,209, 5,985,615, 5,939,598, and 5,916,771, each incorporated by reference; Yang X et al., Crit. Rev Oncol Hemato 38(1): 17-23 (2001); Chadd H E & Chamow S M. Curr Opin Biotechnol 12(2): 188-94 (2001); Green L L, Journal of Immunological Methods 23111-23 (1999); Yang et al., Cancer Research 59(6): 1236-1243 (1999); and Jakobovits A, Advanced Drug Delivery Reviews 31: 33-42 (1998). Antibodies with fully human protein sequences are generated using genetically engineered strains of mice in which mouse antibody gene expression is suppressed and functionally replaced with human antibody gene expression, while leaving intact the rest of the mouse immune system.

Moreover, the generation of antibodies directed against markers present in or on the solid tumor stem cells of the invention can be used as a method of identifying targets for drug development. The antibodies that are raised in an immune response to the solid tumor stem cells can be used to identify antigenic proteins on the solid tumor stem cells using methods known in the art (Harlow, Using Antibodies: A Laboratory Manual (Cold Spring Harbor Press, Cold Spring Harbor, N.Y., (1999)) and can further be used to identify polynucleotides coding for such proteins (Sambrook et al., Molecular Cloning: A Laboratory Manual (Cold Spring Harbor Press, Cold Spring Harbor, N.Y., 1989); Current Protocols in Molecular Biology, Ausubel et al., eds., (Wiley Interscience, New York, 1993). Once identified, the proteins and polynucleotides can be compared with other proteins and polynucleotides previously identified to be involved in cancer. In one embodiment, the XenoMouse™ technology to produce fully human antibodies can be used to generate antibodies directed against drug development targets (see, Jeffrey Krasner, Boston Globe (Jul. 25, 2001) at F4). The present invention provides an improvement to these antibody-based methods of drug discovery by providing the tumorigenic solid tumor stem cells, to which the immune response is raised, for a more precise drug discovery program.

The Microarray Network. In addition to the cDNA libraries and DNA array techniques described above for systematically studying gene expression patterns, one of skill in the molecular biological art can obtain guidance for the use of microarray technology from the University of Michigan Microarray Network (see also, EXAMPLE 9). Furthermore, the University of Michigan has made a large commitment to bioinformatics, by providing funding specifically for microarray data management and analysis, as well as by founding a new Bioinformatics Center for the University.

Alternatively, methods for raising an immune response can take advantage of the "stem cell" qualities of the solid tumor stem cell of the invention. Solid tumor stem cells, solid tumor stem cell protein extracts, purified proteins from solid tumor stem cells, or proteins derived from the expression of cDNAs from solid tumor stem cells (see, above for genetic modification of solid tumor stem cells) to induce an immune response in an animal. The immune response can be directed against cancer cells, as shown by standard immunological methods. For example, the solid tumor stem cells (enriched populations of isolated cells) or proteins can be contacted with o dendritic cells in culture, antigen presenting cells in culture, or antigen presenting cells and T cells in culture. Then antigen-stimulated cells are infused back into the patient.

Alternatively, the solid tumor stem cells of the invention can be genetically engineered to promote an immune response against the tumor stem cells. For example, hematopoietic stem cells can be engineered to contain a T-cell receptor targeting a tumor stem cell antigen. See, U.S. Pat. Nos. 5,914,108 and 5,928,638 incorporated by reference. Thus T cell receptors that recognize antigens expressed by tumor stem cells can be identified, then cloned into hematopoietic stem cells. The engineered hematopoietic stem cells can then be transplanted into a patient and allowed to engraft, giving rise to large numbers of T cells that express receptors recognizing the tumor stem cells. By increasing the numbers of tumor stem cell-specific T cells the anti-tumor immune response can be potentiated.

Other means are also available for increasing the anti-tumor immune response, including using the tumor stem cells as the basis of a vaccine, using the tumor stem cells to stimulate antigen presenting dendritic cells, and using the tumor stem cells as an innoculum to generate anti-tumor antibodies. Tumor stem cells can be used as a vaccine by killing a patient's tumor stem cells, such as by irradiation, and readministering the killed stem cells back into the patient in a physiological and immunologically acceptable carrier, for the purpose of generating an immune response against the tumor stem cells. See, U.S. Pat. No. 4,960,716, in which antibodies were raised to membrane vesicle preparations of breast carcinoma cell cells; U.S. Pat No. 4,584,268, in which anti-human mammary epithelial antibody was produced a membrane fraction of delipidated human milk fat globules; both incorporated by reference.

Dendritic cells from a patient can be cultured in vitro and killed tumor stem cells from the same patient can be added to the cultures to stimulate the dendritic cells. The activated dendritic cells, presenting tumor stem cell antigens, can then be re-administered to the patient to stimulate the patient's anti-tumor response. Finally, tumor stem cells can be administered to an animal such as a mouse, rat, hamster, goat, sheep, rabbit, or donkey to generate antibodies against the tumor stem cells. Preferably, monoclonal anti-tumor stem cell antibodies are made in mouse, rat, or hamster. Monoclonal antibodies that are made in this way can then be administered to patients, or first humanized (as described above) and then administered to patients, to promote an immune response against the tumor stem cells in the patient.

Furthermore, adenoviral vectors have proven especially useful for gene transfer into eukaryotic cells for vaccine development. Graham F L & Prevec L, In Vaccines: New Approaches to Immunological Problems, Ellis RV ed., 363-390 (Butterworth-Heinemann, Boston, 1992).

Probe for scanning microarrays. The complete sequencing of the human genome makes possible the identification of the genes expressed by a particular population of cells. Probes from enriched populations of tumor stem cells can be made using methods known to the art (see, Wang et al., Nature Biotechnology 18: 457 (2000). Analysis of gene expression patterns and protein expression patterns for tumor stem cells and tumor cell progeny populations can be performed by comparing results to known Gene Pattern Databases or to known Protein Pattern Databases (for example, PROSITE, PRINTS: Protein Motif Fingerprint Database, BLOCKS, PFAM, nOMa, PROnOM, or other databases). Searches can be preformed, for example, using the BCM Search Launcher: General Protein Sequence/Pattern Searches (Baylor College of Medicine, Human Genome Sequencing Center, One Baylor Plaza, Houston, Tex.). Commercially available programs for gene and protein analysis are also available (such as CGC (from Genetics Computer Group, Inc.) and DNA STRIDER).

The factors involved in the proliferation, differentiation, or survival of tumor stem cells and tumor stem cell progeny, or their responses to biological agents can be isolated either by constructing cDNA for libraries or to probe microarrays from tumor stem cells, or tumor stem cell, non-tumorigenic cancer cells, or normal tumor cells using techniques known in the art. cDNA can also be made from any of the different populations after exposure to biological agents or drugs to determine the response to such manipulations. The libraries from cells of one population are compared with those of cells of different populations to determine the sequence of gene expression during development and to reveal the effects of various biological agents or to reveal new biological agents that alter gene expression in cancer cells. When the libraries are prepared from neoplastic tissue, genetic factors may be identified that play a role in the cause of cancer cell growth, for example, by comparing the libraries from the cancerous tissue with those from normal tissue. This information can be used in the design of anti-cancer therapies. Additionally, probes can be identified for use in the diagnosis of various cancers or for use in identifying cells at a particular stage in tumor development.

Diagnostic and prognostic evaluation of tumors. A variety of methods can be employed for the diagnostic and prognostic evaluation of tumor and metastasis, and for the identification of subjects having a predisposition to such conditions. Among the methods well known in the art are the use of bone scans, X-ray imaging, MRI tests, CAT scans, and blood tests for tumor associated antigens (see, American Cancer Society, Cancer Facts and Figures 1999: Selected Cancers (1999); American Cancer Society, Breast Cancer Guidelines and Statistics (1999); Kopans Breast Imaging. rd Edition (JB Lippincott, Philadelphia, Pa., 1998); Potter & Partin, NCCN Practice Guidelines for Early Detection of Prostate Cancer 13(11A) Oncology (November 1999). For additional methods of detection, see Franklin et al, Breast Cancer Research & Treatment 41(1): 1-13 (1996); Kufe et al., Cancer Research 43(2): 851-7 (1983). For bone scans, nuclear medicine imaging can be used. Nuclear medicine may be used in addition to mammography to help identify certain abnormalities. Nuclear medicine is also a good tool for evaluating the metastasis of cancer into the lymphatic system, other organs and skeletal system. Tumor associated antigens include for example, BCA 225 (U.S. Pat. No. 5,681,860); Bladder Tumor Associated Antigen (BTA stat test, ARUP Laboratories, Salt Lake City, Utah); tumor-associated antigen CA 125 (Wagner et al., Hybridoma 16(1): 33-40 (1997)); 22-1-1 Ag, YH 206, GA 733, CA 125, carcinoembryonic antigen, and sialyl Lex (Sonoda et al., Cancer 77(8): 1501-1509 (1996). For breast cancer prognosis, cancerous cells can be looked for in the patientls bone marrow. See, for example, Bruan et al., *New Engl. J. Med* (Feb. 24, 2000>>.

Such methods may, for example, utilize reagents such as VEGF nucleotide sequences and VEGF antibodies. Specifically, such reagents may be used, for example, for: (1) the detection of the presence or over-expression of VEGF mRNA relative to the non-carcinogenic tissue state; (2) the detection of an over-abundance of VEGF protein relative to the non-carcinogenic tissue state; (3) the detection of hypoxic conditions in the tumor mass; (4) the detection of the expression of VEGF tyrosine kinase receptors and other angiogenic receptors in adjacent endothelial tissues; and (5) the detection of the expression of oncogenes. The methods may be performed, for example, by utilizing pre-packaged diagnostic kits comprising at least one specific VEGF nucleotide sequence or VEGF antibody reagent described herein, which may be conveniently used, e.g., in clinical settings, to diagnose patients at risk for tumor angiogenesis and metastasis.

Further, the expression of different oncogene alleles may be assessed using these methods. The additional information obtained regarding the expression of other markers provides guidance for the design of appropriate therapies to inhibit angiogenesis or tumor proliferation tailored to the molecular stage of the cancer in a particular patient.

Drug discovery. The invention provides a method for identifying a test compound for reducing solid tumors. The practice of the method can be further determined using the guidance provided in the EXAMPLES below. The steps of the method include assaying the response of tumor cells to biological agent and determining the effects of the biological agent on the tumor stem cell. In other words, the invention provides improved methods of drug discovery by the use of the solid tumor stem cells of the invention.

Figure 11A:
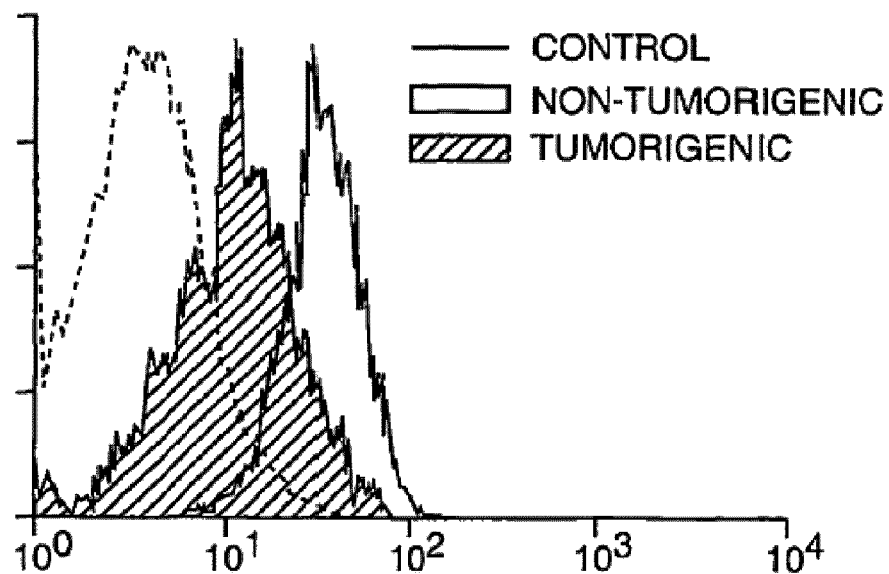
FIG. 11 shows the expression of HER2/neu and EGF-R. Flow cytometry was used to isolate subpopulations of Tumor T1 cells that had been passaged once in NOD/SCID mice. Cells were stained with, in FIG. 11A, anti-EGF-R-PE, anti-B38.1-APC, anti-CD24-FITC, anti-LINEAGE-Cytochrome, anti-mouse-H2K-Cytochrome, and 7AAD or, in FIG. 11B anti-HER2/neu-FITC, anti-B38.I-APC, anti-CD24-PE, anti-LINEAGE-Cytochrome, anti-mouse-H2K-Cytochrome, and 7AAD. Dead cells (7AAD$^+$), mouse cells (H2K$^+$) and LINEAGE$^+$ cells were eliminated from all analyses. The histogram in FIG. 11A depicts the EGF-R expression of the unstained cells (dotted line), B38.1$^+$CD24$^-$LINEAGE$^-$ tumorigenic population (shaded) and the B38$^+$CD24$^+$LINEAGE$^-$ non-tumorigenic (solid line) population. The histogram in FIG. 11B shows HER2/neu expression of the unstained cells (dotted line), B38.1$^+$CD24$^-$LINEAGE$^-$ tumorigenic population (shaded) and the B38$^+$CD24$^+$LINEAGE$^-$ non-tumorigenic (solid line) population. RT-PCR was performed using nested primers to detect EGF-R (FIG. 11C and FIG. 11D) or to detect HER2/neu (FIG. 11E). One cell per sample in panels FIG. 11D and FIG. 11E, or ten cells per sample in panel FIG. 11C, were analyzed. EGF-R is expressed at lower levels in tumorigenic cells than in non-tumorigenic cells at both the protein (FIG. 11A) and mRNA levels (FIG. 11C, FIG. 11D).

Proof of principle of the use of the invention for drug discovery is provided in drug discovery in EXAMPLE 11 and FIG. 11, where the epidermal growth factor (EGF) receptor (EGF-R) and HER2/neu markers (known to be involved in cancers) were identified on solid tumor stem cells. Accordingly, therapies directed against the EGF-R (e.g., Yang X et al., Crit. Rev Oncol Bematol. 38(1): 17-23 (2001)) and HER2/neu markers (see, Breast Disease, Vol. II, HER2: Basic Research, Prognosis and Therapy, Y. Yarden, ed. (1OS Press, Amsterdam, 2000)) can be effectively targeted to solid tumor stem cells.

The identification of biological pathways is an important part of modem drug discovery process. Biological pathways in solid tumor stem cells and other cell populations obtained from solid tumors, particularly pathways involved in drug actions, i.e., pathways that originate at a drug target (e.g., proteins), can be identified for use as shown by U.S. Pat. No. 5,965,352, which is incorporated herein by reference.

In one set of methods, drugs are screened to determine the binding of test compounds to receptors, in which the binding activates a cell's biological pathway to cause expression of reporter polypeptides. Frequently the reporter polypeptides are coded for on recombinant polypeptides, in which the coding polynucleotide is in operable linkage with a promoter.

The terms "operably associated" or "operably linked," as used herein, refer to functionally related polynucleotides. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The detectable signal can be fluorescence, absorbence, or luminescence, depending on the reporter polypeptide, which can be, for example, luciferase (firefly luciferase, *Vibrio* fisceri luciferase, or *Xenorhabdus luminescens* luciferase), green fluorescent protein, green fluorescent protein variant, chloramphenicol acetyltransferase, β-glucuronidase, β-galactosidase, neomycin phosphotransferase, guanine xanthine phosphoribosyltransferase, thymidine kinase, β-lactamase, alkaline phosphatase, invertase, amylase (for yeast based assays) human growth hormone (for activity based assays). The fluorescent detectable signal can be fluorescence resonance energy transfer (FRET), bioluminescence resonance energy transfer (BRET), time-resolved fluorescence (TRF) or fluorescence polarization (FP). Where appropriate, the detectable signal is detected by a machine such as a fluorometer, luminometer, fluorescence microplate reader, dual-monochromator microplate spectrofluorometer, spectrophotometer, confocal microscope (laser scanner), or a charge-coupled device (CCD). The detectable signal is determined by comparing the amount of signal produced when the reporter polypeptide is expressed in the tumor stem cell with the signal produced when the reporter polypeptide is not expressed in the tumor stem cell.

Another technique for drug screening provides for high throughput screening of compounds (see, e.g., PCT application WO 84/03564.) In this method, large numbers of different small test compounds are synthesized on a solid substrate, such as plastic pins or some other surface. The test compounds are reacted with solid tumor stem cells, or portions thereof, and washed. Bound solid tumor stem cells are then detected by methods well known in the art, using commercially available machinery and methods, for example, the Automated Assay Optimization (AAO) software platforms (Beckman, USA) that interface with liquid handlers to enable direct statistical analysis that optimizes the assays; modular systems from CRS Robotics Corp. (Burlington, Ontario), liquid handling systems, readers, and incubators, from various companies using POLARA™ (CRS), an open architecture laboratory automation software for a Ultra High Throughput Screening System; 3P (Plug&Play Peripherals) technology, which is designed to allow the user to reconfigure the automation platform by plugging in new instruments (ROBOCON, Vienna, Austria); the Allegro™ system or Staccato™ workstation (Zymark), which enables a wide range of discovery applications, including HTS, ultra HTS, and high-speed plate preparation; MICROLAB Vector software (Hamilton Co., Reno, Nev., USA) for laboratory automation programming and integration; and others.

For any of these machines and methods, the assays measure a response the target cells (solid tumor stem cells or genetically modified solid tumor stem cells) that provides detectable evidence that the test compound may be efficacious. The detectable signal is compared to control cells and the detectable signal identified by subtraction analysis. The relative abundance of the differences between the "targeted" and "untargeted" aliquots are simultaneously compared using a "subtraction" analysis (differential analysis) technique such as differential display, representational difference analysis (RDA), GEM-Gene Expression Microarrays (U.S. Pat. No. 5,545,531), suppressive subtraction hybridization (SSH) and direct sequencing (PCT patent application WO 96/17957). The subtraction analysis can include the methods of differential display, representational differential analysis (RDA), suppressive subtraction hybridization (SSB), serial analysis of gene expression (SAGE), gene expression microarray (GEM), nucleic acid chip technology, or direct sequencing.

The solid tumor stem cell of the invention is particularly useful in the drug development process because solid tumor stem cells provide a limited and enriched set of targets for drug development. One of the most important steps in rational drug design is the identification of a target, the molecule with which the drug itself interacts. Frequently, the target will be a receptor on or in a tumorigenic solid tumor stem cell.

Likewise, the genetically modified solid tumor stem cell of the invention is particularly useful in the drug development. For example, the genetically modified stem cell can contain polynucleotide with a promoter operably linked to the polynucleotide encoding a reporter polypeptide. The reporter polypeptide is expressed in the tumor stem cell after a receptor of the tumor stem cell is activated by binding to a test compound or inactivated by binding to a test compound. Such a detectable signal makes the genetically modified solid tumor stem cell appropriate for use in high throughput screening (HTS).

The detectable signal can be a result of a positive selection or a negative selection. The positive selection includes manipulations that test the ability of cells to survive under specific culture conditions, ability to express a specific factor, changes in cell structure, or differential gene expression. The selection can be based on the ability of the solid tumor stem cells or genetically modified solid tumor stem cells to:

(a) Grow or survive under specific culture conditions, such as in vitro cell culture.

(b) Express a specific factor that can be measured, the measurement adaptable for a selection. This factor can be anything that is accessible to measurement, including but not limited to, secreted molecules, cell surface molecules, soluble and insoluble molecules, binding activities, activities that induce activities on other cells or induce other organic or inorganic chemical reactions.

(c) Changes in cell structure, including morphological changes that are measured by physical methods such as differential sedimentation, differential light scattering, differential buoyant density, differential cell volume selected by sieving.

(d) Differences in gene expression that can be directly measured, including changes in cell surface markers, changes in biochemical activities, any changes that would be re-selected in changes in binding of fluorescent labeled probes that could be used in conjunction with a Fluorescence Activated Cell Sorter (FACS) or any property that can be used as a basis for a selection. Genetically modified solid tumor stem cells containing polynucleotides that express reporter polypeptides are particularly useful here.

(e) Differences in gene expression that can be indirectly measured, including changes in transcription factor activity that are measured by a synthetic gene construct encoding a selective marker (such as a drug resistance marker or a cell surface marker that could be used in a FACS selection). This category would also include changes in mRNA stability, mRNA localization, mRNA translation control. All of these changes could be the basis of a selection because a synthetic construct which is controlled by one of these regulatory events could be constructed which would drive the expression of an easily selected gene product.

Pharmacogenomics. The invention provides an improved method of ascertaining propensity for malignancy, monitoring the progress of chemotherapy or other anticancer therapy, screening for re-occurrence of cancer, or other similar detection of present or potential cancer, where such method detects for the expression of at least one gene which is over- or under-expressed in a potential cancer cell, as compared with either a solid tumor stem cell isolated from the patient or a collection of solid tumor stem cells. In one embodiment, the method is the assaying of a biological sample (such as from the patient) to be tested for a signal indicating the transcription of a significant (by comparison with the solid tumor stem cell) polynucleotide transcript. In addition, screening assays of biological samples are contemplated, where such assays are conducted during the course of chemotherapy alone, or after surgical intervention to treat cancer, to monitor for the continued presence or return of cancerous cells.

Other embodiments of the invention. The invention provides an article of manufacture (a system or a kit), comprising packaging material and a primary reagent contained within said packaging material. The primary reagent is solid tumor stem cell preparation as described above. The packaging material includes a label that indicates that the primary reagent can be used for identifying an agent for reducing solid tumors. Also, the invention provides a kit for determining the activity level of a particular polynucleotide or protein in a cell. Such kits contain arrays or microarrays containing a solid phase, e.g., a surface, to which are bound, either directly or indirectly, solid tumor stem cells (enriched populations of or isolated), polynucleotides extracted from such solid tumor stem cells, or proteins extracted from such solid tumor stem cells. The kit may also contain probes that are hybridized or bound to the solid tumor stem cell components at a known location of the solid phase. These probes consist of nucleic acids of known, different sequence, with each nucleic acid being capable of hybridizing to an RNA species or to a cDNA species derived therefrom. In particular, the probes contained in the kits of this invention are nucleic acids capable of hybridizing specifically to nucleic acid sequences derived from RNA species which are known to increase or decrease in response to perturbations correlated to the particular diseases or therapies to be monitored by the kit. The probes contained in the kits of this invention preferably substantially exclude nucleic acids which hybridize to RNA species that are not increased or decreased in response to perturbations correlated to the particular levels of disease states or therapeutic effects to be determined by the kit.

The details of one or more embodiments of the invention have been set forth in the accompanying description above. Although any methods and materials similar or equivalent to those described herein can be used in the practice or testing of the present invention, the preferred methods and materials are now described. Other features, objects, and advantages of the invention will be apparent from the description and from the claims.

In the specification and the appended claims, the singular forms include plural referents. Unless defined otherwise in this specification, all technical and scientific terms used herein have the same meaning as commonly understood by one of ordinary skill in the art to which this invention belongs. All patents and publications cited in this specification are incorporated by reference.

The following EXAMPLES are presented in order to more fully illustrate the preferred embodiments of the invention. These EXAMPLES should in no way be construed as limiting the scope of the invention, as defined by the appended claims.

EXAMPLE 1

Isolation of Breast Cancer Stem Cells

The purpose of this EXAMPLE is to show structural and cell functional characterization of breast cancer stem cells.

We have developed both a tissue culture and a mouse model to identify the breast tumor clonogenic cell. In the mouse model, NOD/SCID mice Lapidot et al., Nature 367 (6464): 645-8 (1994>> are treated with VP-16 (Etoposide) (available from commercial sources, such as Moravek Biochemicals, Brea, Calif., USA), and implanted with primary human breast cancer tissue (obtained from mastectomy or lumpectomy specimens). Three of five primary tumors formed tumors in this system.

The tumor cells isolated from malignant pleural effusions obtained from two patients (see, Zhang et al., Invasion & Metastasis 11(4): 204-15 (1991)) were suspended in Matrigel™ (available from Becton Dickinson, Franklin Lakes, N.J., USA), then were injected into mice. Tumors formed in the injected mice.

By this method, we can generate enough tumor cells for analysis by FACS. We also can generate enough tumor cells to perform biological assays to characterize the cells. (For clonogenic assay for detecting rare tumor cells in hematopoietic samples, see U.S. Pat. No. 5,674,694, incorporated by reference).

Phenotypically distinct subsets of tumor cells can be isolated by any suitable means known in the art, including FACS using a fluorochrome conjugated marker-binding reagent. Any other suitable method including attachment to and disattachment from solid phase, is also within the scope of the invention. Procedures for separation may include magnetic separation, using antibody-coated magnetic beads, affinity chromatography and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. Dead cells may be eliminated by selection with dyes that bind dead cells (such as propidium iodide (PI), or 7-AAD). Any technique may be employed that is not unduly detrimental to the viability of the selected cells.

The marker-binding reagent can be directly or indirectly conjugated to a magnetic reagent, such as a superparamagnetic microparticle (microparticle). Direct conjugation to a magnetic particle is achieved by use of various chemical linking groups, as known in the art. Antibody can be coupled to the microparticles through side chain amino or sufhydryl groups and heterofunctional cross-linking reagents. A large number of heterofunctional compounds are available for linking to entities. A preferred linking group is 3-(2-pyridyldithio)propionic acid N-hydroxysuccinimide ester (SPDP) or 4-(N-maleimidomethyl)-cyclohexane-1-carboxylic acid N-hydroxysuccinimide ester (SMCC) with a reactive sulfhydryl group on the antibody and a reactive amino group on the magnetic particle. Alternatively, the marker-binding reagent is indirectly coupled to the magnetic particles. The marker-binding reagent is directly conjugated to a hapten, and hapten-specific, second stage antibodies are conjugated to the particles. Suitable haptens include digoxin, digoxigenin, FITC, dinitrophenyl, nitrophenyl, avidin, biotin, etc. Methods for conjugation of the hapten to a protein, i.e. are known in the art, and kits for such conjugations are commercially available. Fluorochrome labeled antibodies are useful for FACS separation, magnetic particles for immunomagnetic selection, particularly high gradient magnetic selection (HUMS), etc. Exemplary magnetic separation devices are described in PCT patent applications WO 90/07380 and WO 96/09550, and European patent 0 438 520.

We have extensively studied the tumors formed by one of the primary tumors and one of the malignant pleural effusion cells. We have identified low serum tissue culture conditions in which primary breast cancer cells and cells isolated from a mouse xenograft proliferates for at least 1-3 weeks in tissue culture. Using the in vitro tissue culture model, we found that stimulation of a specific receptor can affect the growth and survival of breast cancer cells.

Figures 2A, 2B:
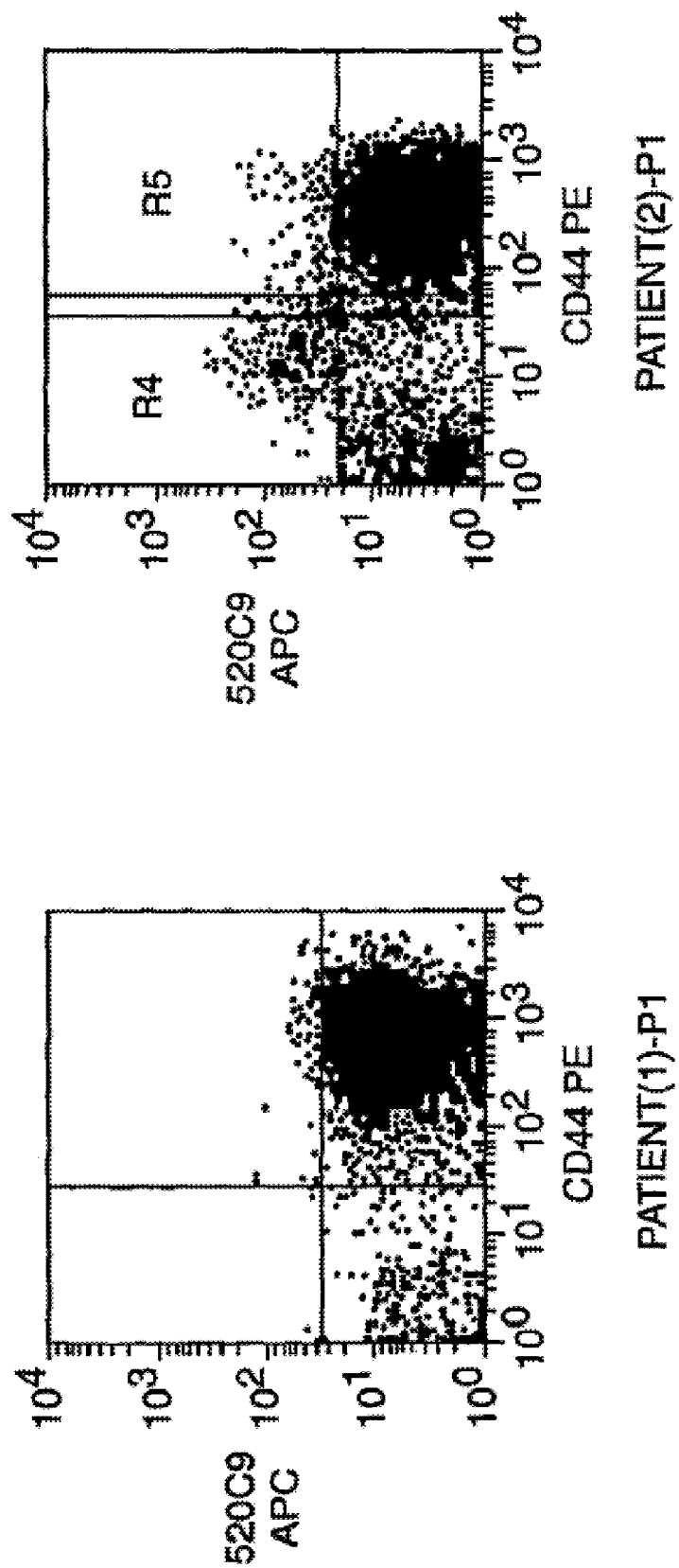
FIGS. 2A and 2B show FACS plots of tumor cells obtained from mice implanted with primary breast cancer tumor cells removed from human Patient (1) and human Patient (2), respectively. Live, human $CD44^+$ and human $CD44^-$ cells were isolated and used for in vitro and in vivo studies.

We have used the in vitro (tissue culture) and in vivo (mouse xenograft) models of human breast cancer. A human tumor growing in the mouse model was harvested and made into a single cell suspension and analyzed by FACS. We found a heterogeneity of expression of cell surface markers on tumor cells. Initially, breast cancer cells isolated from a malignant pleural effusion were separated into groups based upon CD44 expression. Cells were analyzed for expression of markers 520C9 and CD44 (see, FIG. 2). 520C9 is known to recognize c-erbB-2 (HER-2/neu). Ring et al., Molecular Immunology 28:915 (1991). See also, U.S. Pat. No. 4,753,894, which discloses murine monoclonal antibodies that bind selectively to human breast cancer cells. Four populations of cells were identifiable. There was a small population of cells that expressed both markers 520C9 and CD44, a population that expressed either marker alone, as well as a population that expressed neither marker. Cells were isolated with regard to CD44 expression (FIG. 2). $CD44^+$ or $CD44^-$ cells were tested for their ability to proliferate. Marker $CD44^+$ tumor cells, but not marker $CD44^-$ tumor cells, were able to form colonies in vitro and tumors in vivo (TABLE 1). Note that isolation of $CD44^+$ cells results in at least a 2.5-fold purification of the tumorigenic cells.

TABLE 1

ISOLATED POPULATIONS OF BREAST CANCER STEM CELLS

|  | $CD44^+$ | $CD44^-$ |
|---|---|---|
| Colonies in vitro | + | − |
| Tumorigenicity in mice | + | − |

Human breast cancer cells were collected using FACS. Analysis of in vitro colonies was done in 2 separate wells using 5,000 cells of the respective phenotype. In vivo growth of sorted cells was done by injecting mice with $2 \times 10^6$ marker $CD44^+$ or $CD44^-$ cells. Mice were analyzed at week 3 in experiment 1 and week 4 in experiment 2. The injections of marker $CD44^+$ cells, but not marker $CD44^-$ cells, resulted in tumor formation and growth in vitro. The in vitro experiments have been replicated using frozen cells isolated from the patient and support the in vitro experiments. The in vivo experiments have been replicated twice.

These results serve as a proof-of-principle of the stem cell model of solid cancer and demonstrate the following:

(a) solid tumor cells are phenotypically and functionally heterogeneous; some tumor cells are tumorigenic, while others have limited proliferative potential and do not form tumors upon transplantation;

(b) by separating cells by FACS, one can enrich for tumorigenic cells; and (c) by studying the tumorigenic fractions one can isolate tumor stem cells and more carefully focus strategies for identifying therapeutic targets.

This EXAMPLE shows that that the clonogenic breast cancer tumor cell from two tumors express CD44. Other markers also allow the further purification of the breast cancer stem cell. We have analyzed the tumor cells for expression of several antigens. Some antigens with heterogeneous expression patterns include MUCI, Notch-4, annexin V, 317G5, CD9, CD24, 260F9~P-glycoprotein and CD49F. 260F9 binds to a 55 kilodalton glycoprotein (mucin) B cell surface antigen. Weiner L M et al., Cancer Res. 49:4062-4067 (1989); Gregg, E O. et al J. Immunol, 138:4502-4508 (1987). See also, U.S. Pat. No. 4,753,894, which discloses murine monoclonal antibodies that bind selectively to human breast cancer cells. Combinations of these markers with CD44 permit increased enrichment of the tumor stem cells beyond what was achieved with CD44 alone.

Remarkably, all of the $CD44^+$ (tumorigenic) cells are also $B38.1^+$. See, Kufe et al., Cancer Research 43(2): 851-7 (1983) for description of B38.1 antibody. Annexin, Notch-4, and CD24 expression is heterogeneous by the $B38.1^+$ cells. We can thus further purify the breast cancer stem cell from two tumors by analyzing various subpopulations of $B381^+$ or $CD44^+$ cells. Indeed, we have isolated $B38.1^+CD24^+$, and $B38.1^+CD24^-$ cells obtained from a primary biopsy and placed them in tissue culture. Only the $B38.1^+CD24^-$ cells formed colonies. In another tumor, we isolated the $260F9^+CD24^-$, $260F9^+CD24^{hi}$, and the $260F9^+CD24^{lo}$ populations of cells. Only the $CD24^{-/lo}$ population of cells formed tumors (TABLE 2). Note that there is a 5-6 fold enrichment of tumorigenic cells using B38.1 or 260F9 and CD24.

TABLE 2

ANALYSIS OF TUMORIGENICITY OF CD24+ AND CD24−/l0 CELLS

| Tumor formation | CD24+ | $CD24^{-/lo}$ |
|---|---|---|
| Tumor T1 | − | + |
| Tumor T2 | − | + |

NOD/SCID mice were injected with either 50,000-200,000 $CD24^+$ or $CD24^{-/lo}$ cells and analyzed for tumor formation two weeks later.

EXAMPLE 2

Role for Notch in Breast Cell Proliferation

The purpose of this EXAMPLE is to provide preliminary evidence that in at least two different tumors, Notch 4 is expressed by a minority of the tumorigenic cells. Cells from tumor T1 and tumor T2 from EXAMPLE 1 were analyzed for expression of Notch 4. Cells were stained with an anti-Notch 4 polyclonal antibody and analyzed by FACS. 5-15% of cells expressed detectable levels of Notch4. Furthermore, different populations of non-tumorigenic cells express different Notch ligands and members of the Fringe family. To determine which Notch RNAs are expressed by normal breast tissue and breast tumor tissue, we performed RT-PCR using primers specific for each Notch mRNA. Interestingly, Notch 1, Notch 3 and Notch 4, but not Notch 2, were expressed by both normal breast cells and breast tumor cells. We prepared RNA from 100,000 cells. RT-PCR of RNA from normal breast cells or breast tumor cells was performed using primers specific for Notch 1, Notch 2, Notch 3, and Notch 4. A PCR product of the predicted size was present for Notch 1, 3, and 4, showing the presence of these markers in these cells. The signal was lost if the RNA was pretreated with Rnase.

To determine the role of Notch in proliferation, a Notch recombinant ligand or agonist peptides of the ligand were added to the medium in cultures of normal mammary epithelial cells. Both Notch agonists stimulated the survival/proliferation of single cells: in the presence of the Notch agonists, 2-3 times more colonies formed and they included a higher percentage of large, mixed colonies (40% versus 20%). When single cells were plated at clonal density, we obtained two kinds of colonies. There were large colonies made up of hundreds to thousands of cells, presumably arising from solid tumor stem cells, that were of a mixture of myoepithelial cells and ductal epithelial cells. There were also smaller colonies of cells that appeared to contain only a single lineage and that probably represented the progeny of restricted progenitors.

From a normal breast epithelial cell grown in vitro, bilineage colonies (containing both myoepithelial and ductal epithelial cells) were generated by single cells. Myoepithelial cells were identified by staining with an anti-CALLA antibody. Ductal epithelial cells were identified by staining with an anti-ESA antibody. Organoids grown in Matrigel™ in the presence or absence of the Notch agonist peptide branched and proliferated more in the presence of the Notch agonist peptide. This agonist peptide also inhibited differentiation, as indicated by the inhibition of casein production. These results demonstrate that these assays also provide a means for detecting multipotent progenitors from normal breast epithelium. This assay may be used for the purification of normal breast stem cells. These results also demonstrate that Notch has a function in normal breast development.

We then examined Notch 4 expression in breast cancer tumor cells. High levels of Notch 4 were expressed on a minority of the tumor cells. When the B38.1 population, which identifies the tumorigenic population, was analyzed for Notch 4 expression, a distinct minor population of cells that were B38.1low, $Notch\ 4^+$ became apparent.

We sorted $Notch\ 4^+$ and $Notch\ 4^-$ cells and analyzed them in vitro. Surprisingly, neither population grew in tissue culture. There were two possible explanations. First, it was possible that interaction between the two populations of cells was required for cell growth. Next, the antibody may be either an agonist or an antagonist of Notch 4 and may inhibit tumor cell growth. To distinguish between these possibilities, tumor cells were incubated with the anti-Notch 4 antibody, and then assayed in vitro. Breast cancer cells were placed in tissue culture after exposure to an anti-Notch 4 antibody. Cells were incubated on ice for 1 hr. in HBSS containing no anti-Notch 4 antibody, anti-Notch 4 antibody, or anti-Notch 4 antibody that had been preincubated with the peptide used to generate the antibody. Cells were also grown in the presence of soluble Delta and without soluble Delta as a control.

While control cells grew in tissue culture and formed colonies, cells incubated with the Notch 4 antibody did not. When the anti-Notch 4 antibody was incubated with the peptide used to generate the antibody before addition to the cells, growth was restored. To confirm a role for Notch for growth in vitro, cells were incubated in serum free conditions in media that contained soluble Delta, a Notch ligand, or a control culture without Delta. The cultures with Delta formed many colonies, whereas only a few small colonies formed without soluble Delta or in cultures using cells exposed to the anti-Notch 4 antibody. When the antibody was preincubated with the peptide, the antibody no longer blocked proliferation. Thus, the Notch 4 pathway is critical for breast cancer cell growth in vitro.

Tumor cells were exposed to the anti-Notch 4 antibody and then the cells were injected into mice to determine whether the antibody inhibits tumor formation. 35,000 tumor cells were incubated with no antibody, the anti-Notch 4 antibody, or the anti-Notch 4 antibody that had been preincubated with the peptide used to generate the antibody. After two weeks, the diameter of tumors formed by the cells exposed to the anti-Notch 4 antibody was 40% smaller than the control tumors. Thus the cells that were exposed to the anti-Notch 4 antibody formed smaller tumors than cells that were exposed to the anti-Notch 4 antibody that was incubated with the peptide used to generate the antibody.

Figure 4B:
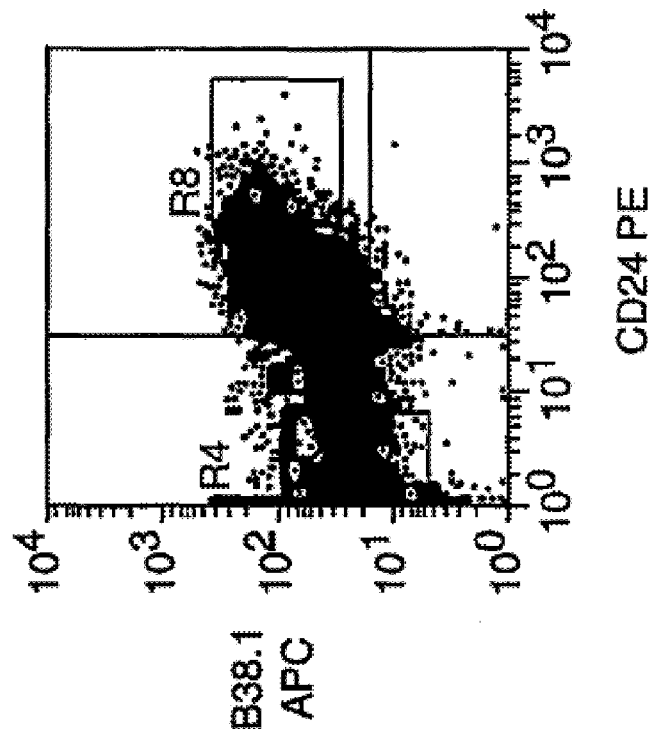
FIG. 4 is a set of FACS plots showing an analysis of tumors arising from the $CD24^-$ cell population from human breast cancers. According to the solid tumor stem cell model, the $CD24^-$ cells give rise to tumors that contain both $CD2^+$ and $CD24^-$ cells. Accordingly, secondary transplants were performed using $B38.1^+CD24^-$ cells (FIG. 4A). The resultant tumors were removed and the cells were re-analyzed with respect to B38.1 and CD24 expression. As predicted by the stem cell model, cells obtained from a tumor arising from transplanted $B38.1^+CD24^-$ cells were heterogeneous with respect to expression of both B38.1 and CD24 (FIG. 4B). The marker expression pattern of the cells isolated from the tumor initiated by the $B38.1^+CD24^-$ cells was similar to that of the original tumor (FIG. 4).
Figure 4A:
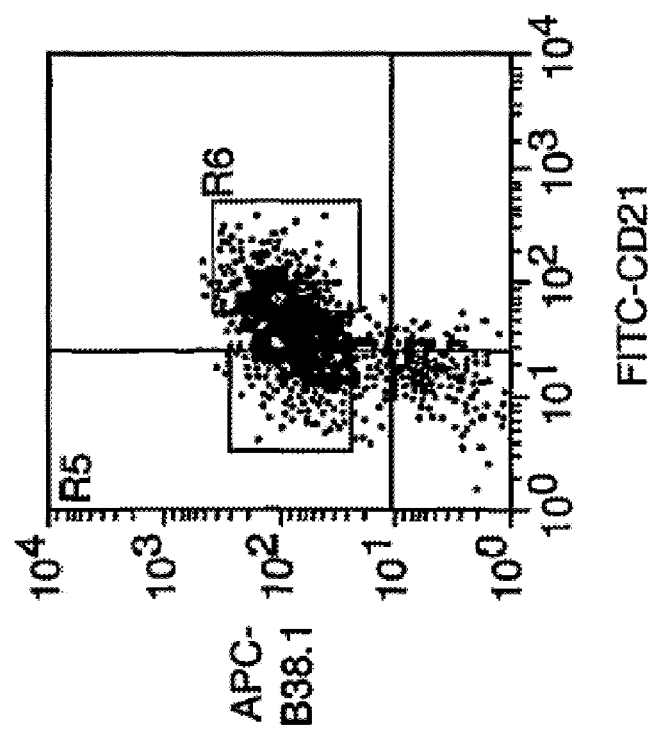

Expression of Notch, Notch ligands, and Fringe family members in subpopulations of breast cancer tumor cells. We examined the expression of members of the Notch receptor family, Notch ligands and Notch signal modifying proteins in populations of breast tumor cells. We initially focused on the markers in the Notch 4$^+$ and Notch 4$^-$ populations. One hundred Notch 4$^+$ or Notch 4$^-$ cells were isolated by FACS (see, FIG. 4). Forty rounds of PCR were performed to detect the indicated mRNA. The Notch 4$^+$ population expressed Notch 1, Notch 4, and Jagged (a Notch ligand). The Notch 4$^-$ population expressed Notch 1 and Notch 3 as well as Jagged. Interestingly, Notch 3 (which may inhibit signaling through other Notch receptors) was not expressed by the Notch 4$^+$ population.

Summary. We have developed in vitro and in vivo assays for normal human breast cells and human breast tumor stem cells. In two different tumors arising in the NOD/SCID mouse model, the tumor cells were heterogeneous with respect to the expression of several cell surface markers. In both tumors, the phenotype of the clonogenic tumor stem cell was B38.1$^+$CD44$^+$CD24$^{-/lo}$. The same population was found to be the clonogenic in the in vitro assay. This B38.1$^+$ population can be further subdivided using several additional markers. In vitro and in vivo evidence strongly implicates the Notch pathway, especially Notch 4, as playing a central pathway in tumorigenesis.

EXAMPLE 3

Mouse Xenograft Model

We have developed a xenograft model in which we have been able to establish tumors from primary breast tumors via injection of tumors in the mammary gland of severely immunodeficient mice. Xenograft tumors have been established from mastectomy specimens of all five patients that have been tested to date. We have also been able to establish tumors from three malignant pleural effusions. NOD/SC1D mice were treated with VP-16, and implanted with primary human breast cancer tissue. Tumor cells isolated from three malignant pleural effusions suspended in Matrigel® were injected into mice and also formed tumors. This enabled us to generate enough malignant tumor cells to facilitate analysis by flow-cytometry and assay for the ability of different subsets of cells to form tumors. We have extensively studied the tumors formed by one of the primary tumors and one of the malignant pleural effusion cells. Furthermore, in the three tumors that we have attempted to do so, we have been able to make single-cell suspensions and transfer the tumors. These improvements in the xenograft assay have allowed us to do biological and molecular tests to characterize the clonogenic breast cancer cell. In addition, we have found tissue culture conditions in which primary breast cancer cells and cells isolated from a mouse xenograft tumor have proliferated for a short period of time (1-3 weeks) in tissue culture.

A human tumor growing in the mouse model was harvested, made into a single cell suspension, and analyzed by FACS. There was heterogeneity of expression of cell surface markers by tumor cells. Initially, breast cancer cells isolated from a malignant pleural effusion were separated into groups based upon CD44 expression. Cells were analyzed for expression of markers 520C9 and CD44. Three populations of cells were identifiable. There was a small population of cells that expressed both markers 520C9 and CD44, a population that expressed either marker alone, as well as a population that expressed neither marker. Cells were isolated with regard to CD44 expression. CD44$^+$ or CD44$^-$ cells were tested for their ability to proliferate. Marker CD44$^+$ tumor cells, but not marker CD44$^-$ tumor cells, were able to form colonies in vitro and tumors in vivo (TABLE 3). Note that isolation of CD44$^+$ cells results in a 2-fold enrichment of the tumorigenic cells.

TABLE 3

HUMAN BREAST CANCER CELLS COLLECTED USING FACS

|  | CD44 | CD44 |
| --- | --- | --- |
| Colonies in vitro | + | − |
| Tumorigenicity in mice | + | − |

Analysis of in vitro colonies was done in 2 separate wells using 5,000 cells of the respective phenotype. In vivo growth of sorted cells was done by injecting mice with 2 × 10$^6$ marker CD44$^+$ or CD44$^-$ cells. Mice were analyzed at week 3 in test 1 and week 4 in test 2. The injections of marker CD44$^+$ cells, but not marker CD44$^-$ cells, resulted in tumor formation and growth in vitro. The in vitro tests have been replicated using frozen cells isolated from the patient and support the in vitro tests. The in vivo tests have been replicated twice.

These results show that the clonogenic breast cancer tumor cell expresses CD44. We have begun to search for other markers that might allow us to further purify the breast cancer stem cell. To do this, we have analyzed the tumor cells for expression of several antigens.

Surprisingly, all of the CD44$^+$ (tumorigenic) cells were also B38.1$^+$. Indeed, we have isolated B38.1$^+$CD24$^+$ cells and B38.1$^+$CD24$^-$ cells obtained from a primary biopsy and placed them in tissue culture. Only the B38.1$^+$CD24$^-$ cells formed colonies.

We next isolated cells from two of the tumors based upon expression of marker CD24. In tumor T2, we isolated the CD24$^-$, the CD24$^{lo}$ and the CD24$^{hi}$ populations. In both cases, only the CD24$^{-/lo}$ populations formed tumors (TABLE 4). Note that there was a 5-6-fold enrichment of tumorigenic cells using B38.1 and CD24.

TABLE 4

FRACTIONS OF HUMAN BREAST CANCER CELLS ISOLATED BY FLOW-CYTOMETRY

| Mouse tumor formation | CD24 | CD24$^{-/lo}$ |
| --- | --- | --- |
| Tumor T1 | − | + |
| Tumor T2 | − | + |

Mice were injected with 50,000 CD24 or CD24$^{-/lo}$ cells. The formation of tumors was determined 4 weeks after injection.

Analysis of tumors arising from the CD24$^-$ cell population. By the solid tumor stem cell model, CD24$^-$ cells give rise to tumors that contain both CD24$^+$ and CD24$^-$ cells. To test this hypothesis, secondary transplants were performed using B38.1$^+$CD24$^-$ cells.

The resultant tumors were removed and the cells were re-analyzed with respect to B38.1 and CD24 expression. As predicted by the stem cell model, cells obtained from a tumor arising from transplanted B38.1$^+$CD24$^-$ cells were heterogeneous with respect to expression of both B38.1 and CD24. The marker expression pattern of the cells isolated from the tumor initiated by the B38.1$^+$CD24$^-$ cells was similar to that of the original tumor.

These results are a proof-of-principle of the solid tumor stem cell model of solid cancer and demonstrate the following:

(1) tumor cells are phenotypically and functionally heterogeneous;

(2) by separating cells by FACS, one can enrich for tumorigenic cells; and (3) by testing the tumorigenic fractions, one can isolate tumor stem cells and more carefully focus strategies for identifying therapeutic targets.

EXAMPLE 4

Analysis of Primary Breast Tumor Cells in a Mouse Model

We have established tumors from eight patients in our mouse model. We also characterize tumors established from three primary tumors and two pleural effusions. Two are fast growing tumors and three are slow growing tumors.

The phenotype of the tumorigenic cell is determined for each different tumor. For analysis, a tumor is removed from the mice and made into a single cell suspension. We first confirm the solid tumor stem cell model of the invention and that the phenotype of tumorigenic cells is indeed $B38.1^+$ $CD44^+CD24^{-/lo}$. In all tumors, we do limiting dilution analysis of cells isolated by FACS based upon expression of these markers.

Based on our preliminary data, the antibody cocktail that leads to the greatest purification of the putative tumorigenic cell follows: anti-38.1-APC, anti-CD44-FITC, and anti-CD24-PE, anti-CD3-cytochrome, anti-CD2-cytochrome, anti-CD10-cytochrome, anti-CD14-cytochrome, anti-CD16-cytochrome, anti-CD3I-cytochrome, CD45-eytochrome, CD140b-cytochrome, anti-CD64-cytochrome, anti-ESA-Phar-red and 7AAD (a viability marker). All antibodies labeled with cytochrome are considered to be part of a lineage cocktail (LINEAGE). FACS is used to isolate the putative breast cancer stem cell, which in xenograft tumor TI are the $CD44^+CD24^{-/lo}LINEAGE^-$ population of cells, the $CD44^+$ $B38.1^+CD24^{-/lo}LINEAGE^-$ population of cells are more enriched, and the $ESA^+CD44^+B38.1^+CD24^{-/lo}LINEAGE^-$ population of cells are most enriched for the breast cancer stem cell. The different populations of malignant cells are tested in the in vivo and in vitro models to confirm that the phenotype of the primary tumorigenic cell does not change while growing in the mouse xenograft model As we progressively enrich the tumorigenic cells, the number of cells and time needed to form a tumor decreases.

EXAMPLE 5

Role for Notch in Breast Cell Proliferation

The Notch protein is a receptor for the growth/survival factors Delta and Jagged (Panin et al., Nature 387(6636): 908-912 (1997); Perron et al., Cellular & Molecular Life Sciences 57(2): 215-23 (2000); Shimizu et al., Journal of Biological Chemistry 274(46): 32961-9 (1999)). In some normal stem cells, Notch is known to play a role in proliferation, survival and differentiation. Apelqvist et al., Nature 400(6747): 877-81 (1999); Berry et al., Development 124(4): 925-36 (1997); Yasutomo et al., Nature 404(6777): 506-10 (2000); Morrison, Cell 101: 499-510 (2000). In certain situations, stimulation of Notch can promote stem cell self-renewal while in other situations it can promote differentiation. Delta activates all four Notch receptors.

We examined Notch 4 expression in the breast cancer tumor cells. Notch 4 was expressed on the minority of the tumor cells. When the B38.1 population, which identifies the tumorigenic population, was analyzed for Notch 4 expression, a distinct minor population of cells that were B38.110 and Notch $4^+$ became apparent.

We sorted Notch $4^+$ and Notch $4^-$ cells and analyzed their ability to form colonies in vitro. Surprisingly, neither population grew in tissue culture. There are two possible explanations. First, it is possible that interaction between the two populations of cells is required for cell growth. Alternately, the antibody may be either an agonist or antagonist of Notch 4 and inhibition or activation of the receptor may inhibit tumor cell growth.

Figure 5:
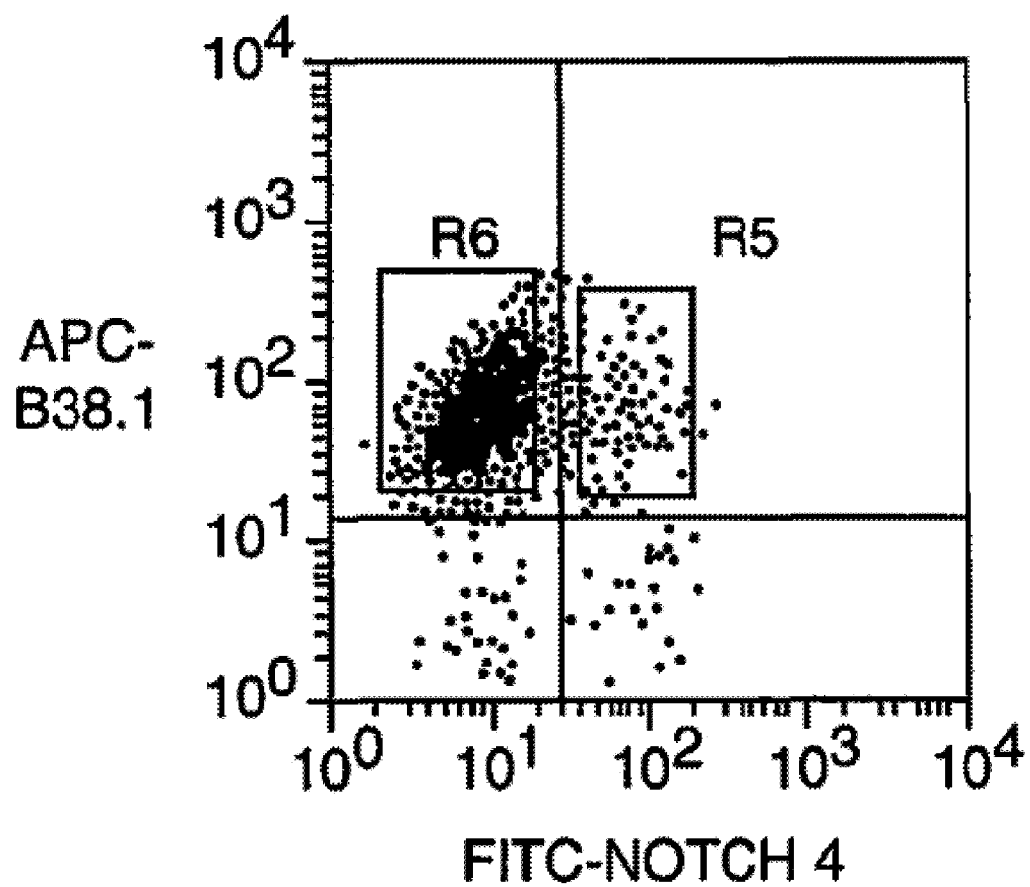
FIG. 5 is a FACS plot showing an analysis of Notch 4 expression. Cells were isolated from a mouse xenograft tumor (see. below) and stained with antibodies. Malignant cells were analyzed for expression of B38.1 and Notch 4. Mouse cells and dead cells were gated out of the analysis.
Figure 6A:
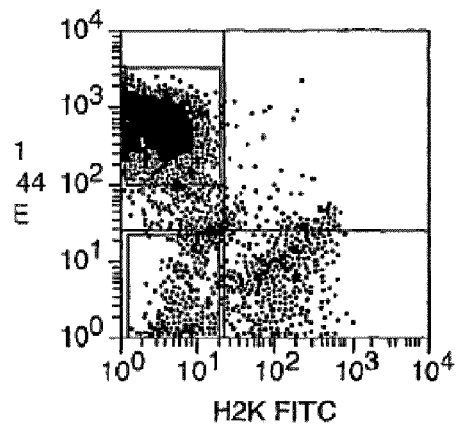
FIG. 6A and FIG. 6B are dot plots of the unfractionated T1 and T2 cells showing CD44 and H2K expression as indicated. Plots showing the isolated $CD44^+$ (FIG. 6C, FIG. 6D) and $CD44^-$ (FIG. 6E, FIG. 6F) populations depict reanalyses of cells that had been isolated by flow-cytometry. These cells were injected into the mammary fat pads of mice to examine their tumorigenicity. TABLES 1 and 3 show that the $CD44^+$ cells but not the $CD44^-$ cells were tumorigenic.
Figure 6B:
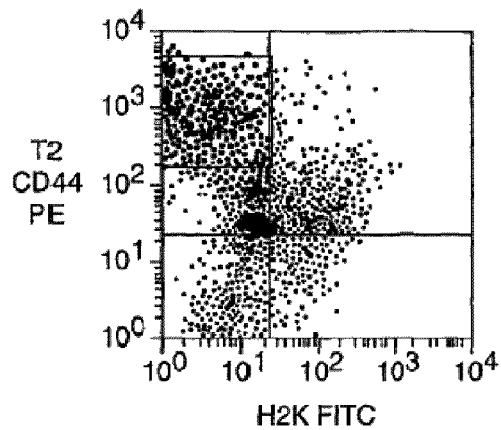
Figure 6C:
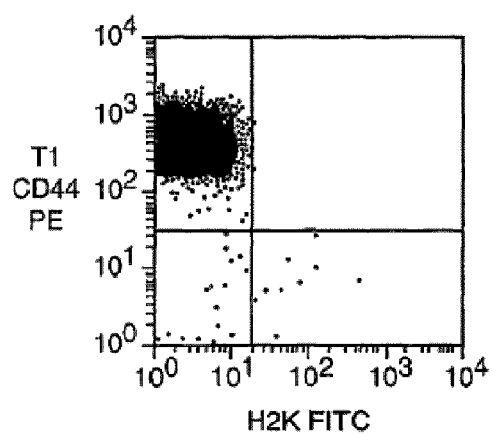
FIG. 6 shows the fractionation of breast cancer cells based upon CD44 expression. Tumor T1 cells (FIG. 6A, FIG. 6C, and FIG. 6E) and Tumor 1'2 cells (FIG. 6B, FIG. 6D, and FIG. 6F) were stained with anti-CD44-PE, anti-mouse H2K-FITC and the viability dye 7AAD. Flow cytometry was used to isolate live, human (H2K–) cells that were either $CD44^+$ (FIG. 6C, FIG. 6D) or $CD44^-$ (FIG. 6E, FIG. 6F). Dead cells (7AAD) were eliminated from all analyses.
Figure 6D:
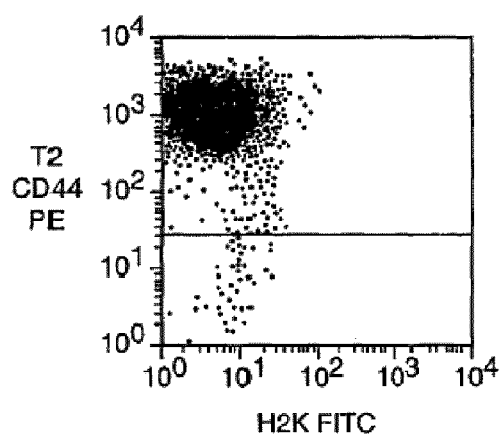
Figure 6E:
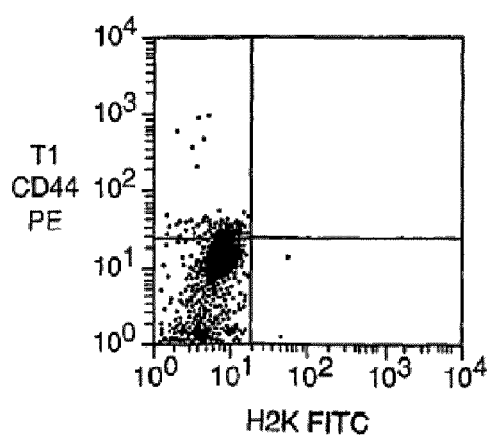
Figure 6F:
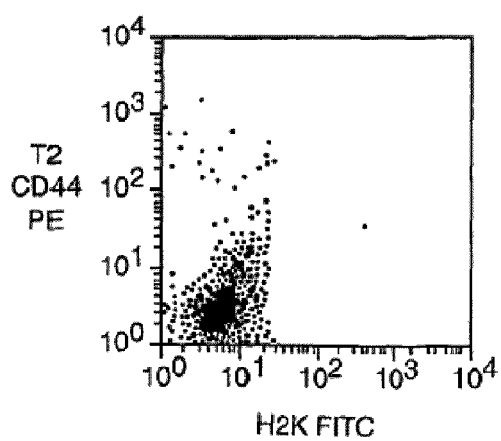
Figure 8:
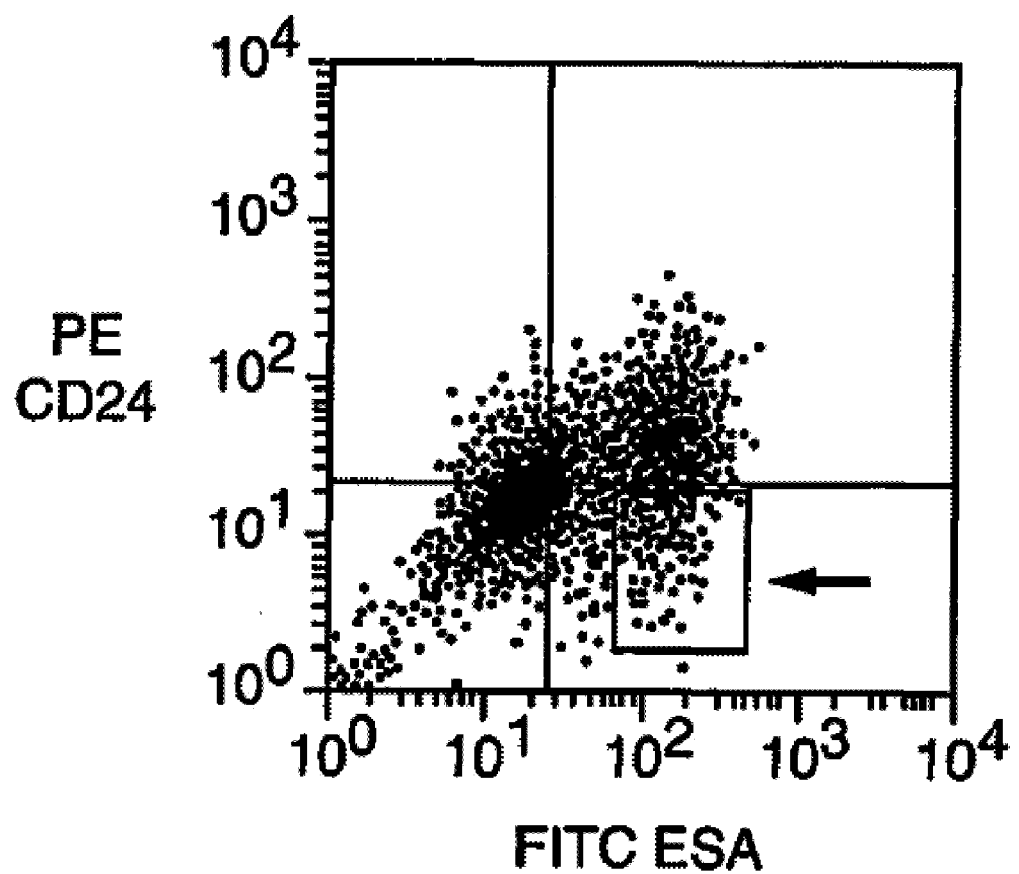
FIG. 8 shows the enrichment of tumorigenic cells based upon ESA expression. Flow cytometry was used to isolate subpopulations of Tumor T1 cells that were tested for tumorigenicity in NOD/SCID mice. T1 cells had been passaged once in NOD/SCID mice. Cells were stained with anti-B38.1-APC, anti-CD24-PE, anti-ESA-FITC, anti-LINEAGE-Cytochrome, anti-mouse-H2K-Cytochrome (T1), and 7AAD. Dead cells ($7AAD^+$), mouse cells ($H2K^+$) and $LINEAGE^+$ cells were eliminated from the analysis. The dot plot in FIG. 8A depicts the CD24 and ESA staining pattern of live human B38.1+LINEAGE– cells. The tumorigenic population is boxed and marked with an arrow.

To distinguish between these possibilities, unseparated tumor cells were incubated with the anti-Notch 4 antibody, and then assayed for the ability to form colonies in vitro. While control cells grew in tissue culture and formed colonies (FIG. 5A), cells incubated with the Notch 4 antibody did not grow (FIG. 5B). When the anti-Notch 4 antibody was pre-incubated with the peptide used to generate the antibody (this peptide should theoretically block binding of the antibody to the cells), the ability of the tumor cells to form colonies was restored (FIG. 8C). To confirm that Notch regulates colony formation by tumor cells, cells were incubated in medium with or without soluble Delta (FIG. 5A and FIG. 5D, respectively). The cultures with Delta formed many colonies (FIG. 5A), whereas only a few small colonies formed in medium lacking soluble Delta or in cultures using cells exposed to the anti-Notch 4 antibody (FIG. 5B, FIG. 5D, and FIG. 5E). Taken together, these results show that the Notch 4 pathway regulates the proliferation/survival of breast cancer cells in cells and that the anti-Notch 4 antibody blocks activation in vitro.

Next, tumor cells were incubated with the anti-Notch 4 antibody and then the cells were injected into mice to determine whether the antibody inhibits tumor formation. The cells that were exposed to the anti-Notch 4 antibody formed smaller tumors than cells that were exposed to the anti-Notch 4 antibody that was incubated with the peptide used to generate the antibody before addition to the cells. Approximately 350,000 tumor cells were incubated with no antibody, the anti-Notch 4 antibody, or the anti-Notch 4 antibody that had been incubated with the peptide used to generate the antibody. After two weeks, the diameter of tumors formed by the cells exposed to the anti-Notch 4 antibody was 40% smaller than either of the control tumors. The simplest explanation of the in vitro and in vivo assays is that Notch 4 activation promotes proliferation/survival of stem cells and that the anti-Notch 4 antibody blocks receptor activation.

EXAMPLE 6

Further Characterization of Breast Cancer Stem Cells

Human breast cancer tumors have been established in NOD/SCID mice from five tumors (mastectomy specimens of three primary breast tumors and two malignant pleural effusions from metastatic breast cancer). The five tumors were initially used to understand neoplastic cell marker heterogeneity. Based upon these results, experiments using cells isolated from primary tumors directly after removal from a patient were done to confirm that the mouse xenograft model accurately reflects human breast cancer.

CD44 expression and tumorigenicity. Cells obtained from the metastatic breast cancer, designated T1, and one primary breast tumor, designated T2, were chosen to expand in the mice to obtain sufficient cells for analysis. To accomplish this, $10^6$-$10^7$ pleural effusion cells from T1 (a frozen sample) or a 1-2 mm³ piece of T2 (fresh biopsy sample) were grown in the mouse mammary fat pad for 1 to 3 months. The resulting human tumors were then harvested, made into a single cell suspension and analyzed by flow-cytometry for expression of several different antigens. Contaminating mouse cells were gated out of the analysis by eliminating cells expressing mouse H-2K (major histocompatibility complex class I) and dead cells were eliminated using a viability dye.

As predicted by the solid tumor stem cell model, cells displayed heterogeneous expression of a variety of cell surface-markers including CD44 and B38.1. To determine whether these markers could distinguish tumorigenic from non-tumorigenic cells, CD44$^+$ and CD44$^-$ cells (FIG. 6) were isolated from these in vivo passaged n or T2 cells and NOD/SCID mice were injected with CD44$^+$ or CD44$^-$ cells.

Identification of other informative markers. Between 6 and 12 weeks after injecting, mice were examined for tumors by observation and palpation, then all mice were necropsied to look for growths at injection sites that might be too small to palpate. All of the CD44$^+$ injections gave rise to visible tumors, but none of the CD44$^-$ injections formed detectable tumors (TABLE 5). Next, cells from first passage T1 and T2 were sorted based upon the expression of B38.1 and injected into mice. Tumors appeared from all injections of B38.1$^+$ cells but no tumor formation was detected from B38.1$^-$ cells (TABLE 5). Thus, tumorigenic cells from both passaged tumors were B38.1$^+$CD44$^+$.

TABLE 5

Tumorigenicity of different populations of tumor T1 and tumor T2 cells

| Cells/injection | # tumors/# of injections | | |
|---|---|---|---|
| | $8 \times 10^5$ | $5 \times 10^5$ | $2 \times 10^5$ |
| T1 cells | | | |
| CD44$^-$ | 0/2 | 0/2 | – |
| CD44$^+$ | 2/2 | 2/2 | – |
| B38.1$^-$ | 0/2 | 0/2 | – |
| B38.1$^+$ | 2/2 | 2/2 | – |
| CD24$^+$ | – | – | 1/6 |
| CD24$^-$ | – | – | 6/6 |
| T2 cells | | | |
| CD44$^-$ | 0/2 | 0/2 | – |
| CD44$^+$ | 2/2 | 2/2 | – |
| B38.1$^-$ | 0/2 | 0/2 | – |
| B38.1$^+$ | 2/2 | 2/2 | – |
| CD24$^+$ | – | – | 1/6 |
| CD24$^-$ | – | – | 6/6 |

Cells were isolated by flow cytometry as described in FIG. 2 based upon expression of the indicated marker and assayed for the ability to form tumors after injection of 2-8 × 10⁵ cells into the mammary fat pad of NOD/SCID mice. The number of tumors that formed/the number of injections that were performed is indicated for each population of cells.

The tumors were also heterogeneous for CD24 expression. When 200,000 CD24$^+$ or CD24$^{-/lo}$ cells were injected into NOD/SCID mice, all mice injected with CD24$^{-/lo}$ cells grew tumors (TABLE 5). Although no tumors could be detected by palpation in the locations injected with CD24$^+$ cells, two of twelve mice injected with CD24$^+$ cells did contain small growths at the injection site that were detected only upon necropsy. The sites injected with CD24$^{-/lo}$ cells, by contrast, all had tumors greater than 1 cm in diameter that were readily apparent visually and by palpation. Since it is extremely difficult to completely eliminate CD24$^-$ cells from the CD24$^+$ fraction by flow-cytometry, the small growths likely represent contamination by the 1-3% of CD24$^-$ cells that are typically present in the sorted CD24$^+$ population. Alternately, the small growths might have arisen from CD24$^+$ cancer cells that had reduced proliferative capacity. At present we cannot distinguish between these possibilities. Nonetheless, all of the cells that produced palpable tumors in this xenograft model were B38.1$^+$CD44$^+$CD24$^{-/lo}$.

Several antigens associated with normal cell types, to which we refer collectively as LINEAGE (CD2, CD3, CD10, CD14, CD16, CD19, CD31, –CD45, –CD64 and –CD140b) markers, were found not to be expressed by the cancer cells based on analyses of tumors that had been passaged multiple times in mice. By eliminating LINEAGE cells, normal human leukocytes, endothelial cells, and fibroblasts were eliminated, especially from unpassaged or first passage tumors.

Figure 7A:
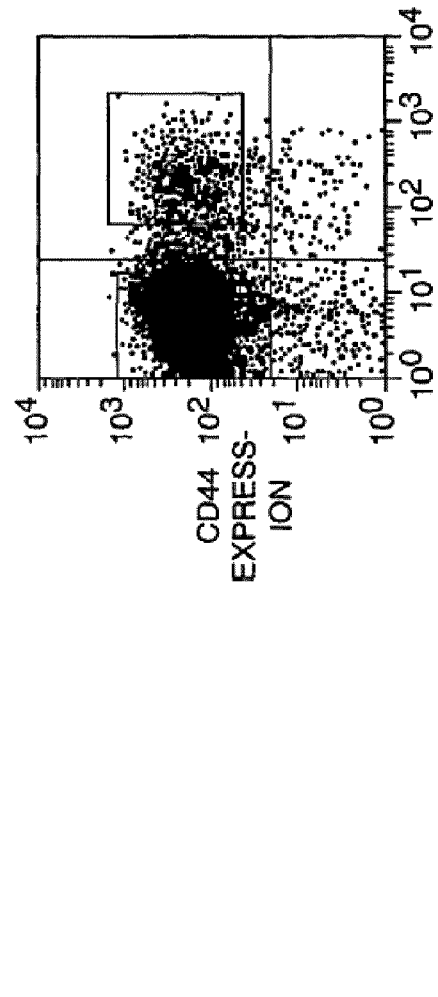
FIG. 7A, FIG. 7B, and FIG. 7C show unfractionated tumor cells. $B38.1^+CD44^+LINEAGE^-$ cells that were either $CD24^{-/lo}$ (FIG. 7G, FIG. 7H, FIG. 7I) or $CD24^+$ (FIG. 7D, FIG. 7E, FIG. 7F) were isolated from these tumor cells by flow-cytometry.
Figure 7B:
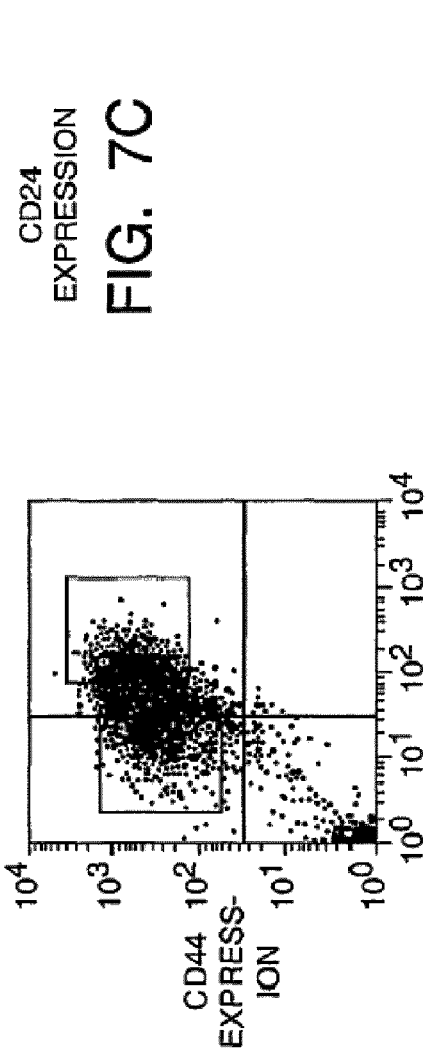
Figure 7C:
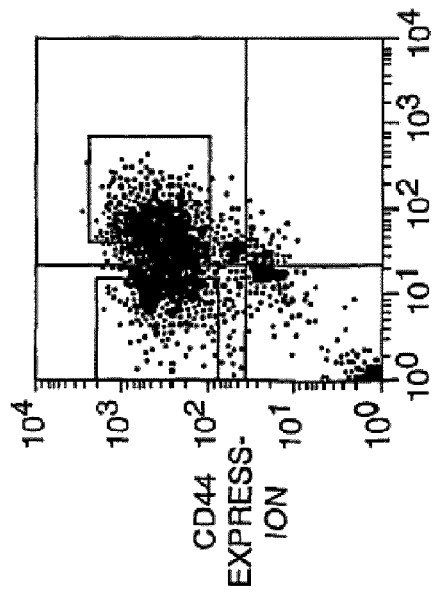
Figure 7D:
FIGS. 7D-7I depict reanalyses of these sorted populations, which were subsequently injected into the mammary fat pads of NOD/SCID mice to test tumorigenicity.
Figure 7E:
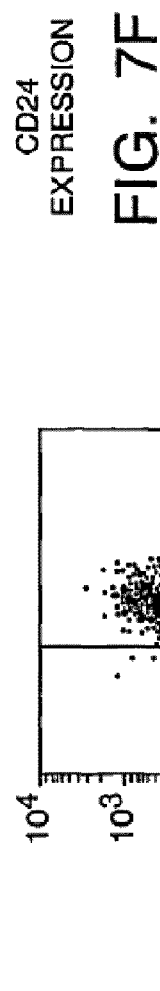
Figure 7F:
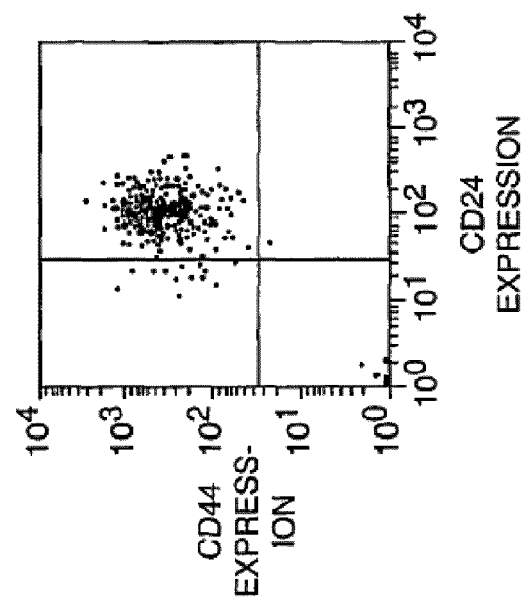
Figure 7J:
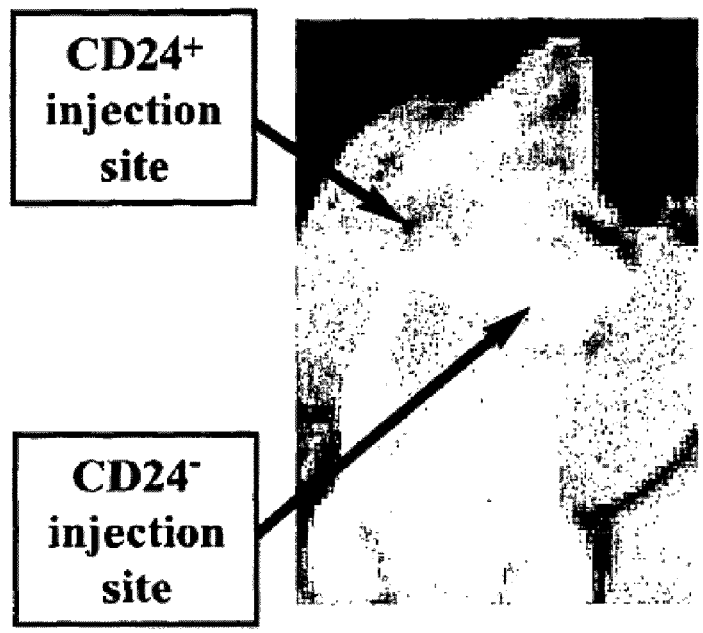
FIG. 7J shows a representative tumor in a mouse at the $B38.1^+CD44^+CD24^{-/lo}LINEAGE^-$ injection site, but not at the $B38.1^+CD44^+CD24^+LINEAGE^-$ injection site. Histology performed on tissue from the $CD24^+$ (FIG. 7K, 20× objective magnification) and C024.flo (FIG. 7L, 40× objective magnification) injection sites exhibited normal mouse tissue and malignant cells respectively.
Figure 7K:
FIG. 7 shows the isolation of tumorigenic cells. Flow cytometry was used to isolate subpopulations of Tumor T1 (FIG. 7A, FIG. 7D, and FIG. 7G), Tumor 2 (FIG. 7B, FIG. 7E, and FIG. 7F) or Tumor T5 cells (FIG. 7C, FIG. 7F, and FIG. 7I) that were tested for tumorigenicity in NOD/SCID mice. T1 and T2 cells had been passaged once in NOD/SCID mice while T5 cells were obtained from material that had been frozen immediately after removal from a patient. Cells were stained with anti-B38.1-APC, anti-CD44-PE, anti-CD24-FITC, anti-LINEAGE-Cytochrome, anti-mouse-H2K-Cytochrome (T1 and T2 cells only), and 7AAD. Dead cells (7AAD), mouse cells (H2K) and $LINEAGE^+$ cells were eliminated from all analyses. Each dot plot depicts the CD24 and C044 staining patterns of live human $B38.1^+CD44^+LINEAGE^-$ cells.
Figure 7L:
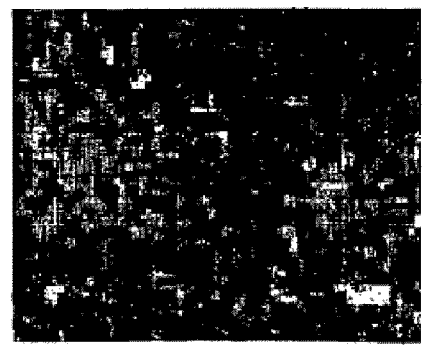

Flow-cytometric analysis of four of the tumors established in NOD/SCID mice revealed that all of these tumors were heterogeneous with respect to B38.1, CD44, and CD24 expression (see, for example, FIG. 7A, FIG. 7B). However, each of the tumors contained a distinct population of B38.1$^+$CD44$^+$CD24$^{-/lo}$ cells. In four independent tumors that were analyzed after one passage in NOD/SCID mice, the frequency of B38.1$^+$CD44$^+$CD24$^{-/lo}$ cells was 9.5±4.5% (mean±standard deviation) of live human tumor cells. Seven weeks after inoculation, the injection sites of B38.1$^+$CD44$^+$CD24$^{-/lo}$LINEAGE$^-$ cells and B38.1$^+$CD44$^+$CD24$^+$LINEAGE$^-$ cells were examined by histology. The B38.1$^+$CD44$^+$CD24$^{-/lo}$LINEAGE$^-$ injection sites contained tumors greater than 1 cm in diameter while the B38.1$^+$CD44$^+$CD24$^+$LINEAGE$^-$ injection sites contained no detectable tumors. Only normal mouse mammary tissue was seen by histology at the sites of the B38.1$^+$CD44$^+$CD24$^+$LINEAGE$^-$ injections (FIG. 7K), whereas the tumors formed by B38.1$^+$CD44$^+$CD24$^{-/lo}$LINEAGE$^-$ cells contained malignant cells as judged by morphology in hematoxylin and eosin stained sections (FIG. 7L). Even when B38.1$^+$CD44$^+$CD24$^+$LINEAGE$^-$ injection sites were examined after 11 weeks, no tumors were detected.

Enrichment of tumorigenic cells using B38.1, CD44, CD24, and LINEAGE markers. T1, T2, and T3, a third tumor that had been passaged once in NOD/SCID mice, were tested to determine whether tumorigenic cells could be enriched based upon expression of B38.1, CD44, CD24 and LINEAGE markers. In all cases, the B38.1$^+$CD44$^+$CD24$^{-/lo}$LINEAGE$^-$ cells were markedly enriched for tumorigenic cells. When injecting unsorted T1 or T2 cells, 5×10⁴ cells consistently gave rise to a tumor, but 10⁴ cells gave rise to tumors in only a minority of cases (TABLE 6). In contrast when B38.1$^+$CD44$^+$CD24$^{-/lo}$LINEAGE$^-$ cells were isolated from T1 or T2 (FIG. 7), as few as 10³ cells from this population were able to give rise to tumors in all cases (TABLE 6, FIG. 7J and FIG. 7L). Cells that were B38.1$^+$CD44$^+$LINEAGE$^-$ but CD24$^+$ failed to form tumors. These data indicate that the B38.1$^+$CD44$^+$CD24$^{-/lo}$LINEAGE$^-$ population is at least 10-fold enriched for the ability to form tumors in NOD/SC1D mice relative to unfractionated tumor cells. This population accounted for 4-17% of the cells in T1 and T2 (5-23% of cancer cells).

EXAMPLE 7

Analysis of Primary Human Tumor Cells

To rule out the possibility that the tumorigenic activity in the enriched population of EXAMPLE 7 arose as a result of propagation in the xenograft model, we isolated unfrozen pleural effusion breast cancer cells based upon expression of CD44 and CD24. Approximately 11% of the neoplastic cells were CD44$^+$CD24$^{-/lo}$LINEAGE$^-$ and 75% CD44$^+$CD24$^+$ LINEAGE$^-$. All three injections of 100,000 CD44$^+$CD24$^{-/lo}$ LINEAGE$^-$ but none of the CD44$^+$CD24$^+$LINEAGE$^-$ cells, formed tumors (TABLE 6). We next tested whether the B38.1$^+$CD44$^+$CD24$^{-/lo}$ population from unpassaged breast tumor specimens (FIG. 7I) was tumorigenic. Of four independent tumors that were analyzed after being passaged in mice, there were only enough frozen unpassaged cells available of T1 to permit flow-cytometry. In addition, frozen unpassaged cells from a fifth patient (T5) were analyzed. Five percent of unpassaged T1 cells and 35% of unpassaged T5 cells were B38.1$^+$CD44$^+$CD24$^{-/lo}$LINEAGE$^-$.

All 40,000 B38.1$^+$CD44$^+$CD24$^{-/lo}$LINEAGE$^-$ cells or 40,000 B38.1$^+$CD44$^+$CD24$^+$LINEAGE$^-$ cells that were isolated by flow-cytometry from unpassaged T1 were injected into a single mouse. From the unpassaged T5 cells, 60,000-100,000 cells of the B38.1$^+$CD44$^+$CD24$^{-/lo}$LINEAGE$^-$ (FIG. 7I) and B38.1$^+$CD44$^+$CD24$^+$LINEAGE$^-$ (FIG. 7F) populations were isolated and injected into each of three NOD/SCID mice. The CD24$^{-/lo}$ population formed tumors from the T1 cells and in 2 of 3 injections from T5 cells, but the CD24$^+$ population never formed tumors, demonstrating that the tumorigenic population identified in the passaged tumors also existed in the unpassaged T1 and T5 samples. When tumors that arose from the unpassaged T1 cells were analyzed, the frequency of B38.1$^+$CD44$^+$CD24$^{-/lo}$LINEAGE$^-$ cells was similar in both passaged and unpassaged T1 samples.

EXAMPLE 8

Further Characterization of the Cell Populations from a Breast Cancer Tumor

In one tumor, tumorigenic cells were further enriched by selecting the ESA$^+$ subset of the B38.1$^+$CD44$^+$CD24$^{-/lo}$ population. When ESA$^+$ CD44$^+$CD24$^{-/lo}$LINEAGE$^-$ cells were isolated from T1 (FIG. 8A), as few as 200 cells from this population were able to give rise to a tumor while injection of 2,000 B38.1$^+$CD44$^+$CD24$^{-/lo}$LINEAGE$^-$ but ESA$^-$ cells failed to form tumors in any case (TABLE 6). At least 10,000 unfractionated cells were required to form any tumors. Thus, the ESA$^+$ CD44$^+$CD24$^{-/lo}$LINEAGE$^-$ population was at least 50 fold enriched for the ability to form tumors relative to unsorted tumor cells. The ESA$^+$B38.1$^+$CD24$^{-/lo}$LINEAGE$^-$ population accounted for 2-4% of T1 cells (2.5-5% of cancer cells). The ESA$^+$B38.1$^+$CD24$^{-/lo}$LINEAGE$^-$ and the non-tumorigenic cells were examined by cytology and both populations consisted of malignant cells that were virtually indistinguishable in appearance.

EXAMPLE 9

Use of Cancer Stem Cells to Improve Tissue Culture Conditions for Growth of Breast Cancer Cells In tissue culture, it has long been known that only a minority of primary tumor cells are capable of forming colonies.

TABLE 6

Tumorigenic breast cancer cells are highly enriched in the CD44$^+$B38$^+$CD24$^-$ population

| Cells | \multicolumn{9}{c}{Number of tumors/number of injections for each cell dose injection} | | | | | | | | |
|---|---|---|---|---|---|---|---|---|---|
| | $5 \times 10^5$ | $1 \times 10^5$ | $5 \times 10^4$ | $2 \times 10^4$ | $1 \times 10^4$ | $5 \times 10^3$ | $1 \times 10^3$ | $5 \times 10^2$ | $2 \times 10^2$ |
| T1 cells (xenograft) | | | | | | | | | |
| Unsorted | 4/4 | 4/4 | 6/6 | — | 2/6 | — | 0/6 | — | — |
| B38.1$^+$CD44$^+$CD24$^+$ | — | — | — | 0/5 | 0/5 | 0/5 | 0/5 | — | — |
| B38.1$^+$CD44$^+$CD24$^-$ | — | — | — | 5/5 | 5/5 | 5/5 | 5/5 | — | — |
| ESA$^+$B38$^+$CD24$^-$ | — | — | — | — | — | — | 8/8* | 2/2 | 1/2 |
| ESA$^-$B38$^+$CD24$^-$ | — | — | — | — | — | — | 0/8* | 0/2 | 0/2 |
| T2 cells (xenograft) | | | | | | | | | |
| Unsorted | 4/4 | 4/4 | 4/4 | — | 1/6 | — | 0/6 | | |
| B38.1$^+$CD44$^+$CD24$^+$ | — | — | — | 0/5 | 0/5 | 0/5 | 0/5 | — | — |
| B38.1$^+$CD44$^+$CD24$^-$ | — | — | — | 5/5 | 5/5 | 5/5 | 5/5 | — | — |
| T3 cells (xenograft) | | | | | | | | | |
| B38.1$^+$CD44$^+$CD24$^+$ | — | — | — | — | 0/2 | — | — | — | — |
| B38.1$^+$CD44$^+$CD24$^-$ | — | — | — | — | 2/2 | — | — | — | — |
| T5 cells (primary cells) | | | | | | | | | |
| CD44$^+$CD24$^+$ | | 0/3 | | | | | | | |
| CD44$^+$CD24$^-$ | | 3/3 | | | | | | | |
| T1 cells (primary cells) | | | | | | | | | |
| B38.1$^+$CD44$^+$CD24$^+$ | | | 0/1 | | | | | | |
| B38.1$^+$CD44$^+$CD24$^-$ | | | 1/1 | | | | | | |
| T6 cells (primary cells) | | | | | | | | | |
| B38.1$^+$CD44$^+$CD24$^+$ | | 0/1 | 0/2 | | | | | | |
| B38.1$^+$CD44$^+$CD24$^-$ | | 1/1 | 1/2 | | | | | | |

Cells were isolated from first passage tumor T1, tumor T2, or tumor T3 cells. B38.1$^+$CD44$^+$CD24$^{-/lo}$LINEAGE$^-$ and B38.1$^+$CD44$^+$CD24$^+$LINEAGE$^-$ cells were isolated by flow-cytometry as described in FIG. 3. The indicated number of cells of each phenotype was injected into the mammary fat pad of NOD/SCID mice. The number of tumors that formed from injections of each group of cells is indicated. Note that isolation of B38.1$^+$CD44$^+$CD24$^{-/lo}$LINEAGE$^-$ cells results in more than a ten-fold enrichment in tumorigenic cells and that no tumors arose from injection of B38.1$^+$CD44$^+$CD24$^+$LINEAGE$^-$ cells. When cells were sorted as ESA$^+$ in addition to B38.1$^+$CD24$^-$, injections of as few as 200 cells gave rise to a tumor, an approximately 50-fold enrichment in tumorigenicity relative to unsorted cells.
* for these injections $2 \times 10^3$ cells were used instead of $1 \times 10^3$.

According to the solid tumor stem cell model, while the non-tumorigenic population of cells might retain some ability to proliferate, the tumorigenic population of cells would have a greater capacity to do so. Equal numbers of the tumorigenic phenotype and the non-tumorigenic cells, isolated either directly from a primary tumor or from tumor T1 and tumor T4 growing in mice, were seeded at clonal density in tissue culture plates and colony formation was measured. The primary patient cells were from an aliquot of frozen primary cells from a tumor that easily forms a breast cancer cell line and proliferates well in tissue culture.

Cytology showed that each population contained cancer cells of epithelial origin (FIG. 9).

Initially, colonies formed from not only the tumorigenic cells but in some tumors also from the non-tumorigenic cells (FIG. 9). However, by day twelve, the colonies formed by the tumorigenic cells had grown while the non-tumorigenic cells had died (FIG. 9). By day 14, only B38.1$^+$CD44$^+$CD24$^+$LINEAGE$^-$ cells formed numerous large colonies of cancer cells (FIG. 9C).

We have passed these cells in tissue culture over 3 passages, and the epithelial neoplastic cells continue to proliferate. By contrast, the non-tumorigenic cells were capable of forming only small colonies consisting of 2-4 cells that stopped proliferating after a few days (FIG. 9C).

These results illustrate two important points. First, the phenotype of the stem cells is not an artifact of the immune-deficient mouse assay. The fact that the phenotypically identical population of cells had increased proliferative ability in both the mouse xenograft model and the in vitro assays shows that this population is the tumorigenic population of cells found in patients with breast cancer.

Second, at least some of the non-tumorigenic cells have the capacity for limited proliferation. This shows that the markers used to identify the non-tumorigenic population were not simply selecting for cells that lacked viability.

These results of this EXAMPLE provides a solution to the problem that the use of the in vitro clonogenic assay to predict chemotherapy drug sensitivity frequently does not predict a particular patient's response to therapy. In one of the tumors used in this EXAMPLE, the non-tumorigenic population of cells formed colonies almost as efficiently as the tumorigenic cells (the solid tumor stem cells of the invention) on day 4. In using this tumor for a drug-screening assay, if the non-tumorigenic and tumorigenic cells that are clonogenic in vitro respond differently to a particular test compound, then the assay, especially if scored early, would not have reflected the ability of the test compound to eliminate breast cancer stem cells in vivo.

EXAMPLE 10

The Stem Cell Population Regenerates Both the Stem Cell and the Non-Tumorigenic Populations of Cells According to the deterministic solid tumor stem cell model (FIG. 1B), B38.1$^+$CD44$^+$CD24$^{-/lo}$LINEAGE$^-$ tumorigenic cells form tumors that contain additional B38.1$^+$CD44$^+$CD24$^{-/lo}$LINEAGE$^-$ tumorigenic cells as well as phenotypically heterogeneous populations of non-tumorigenic cells. Classical models would suggest that tumors that form from B38.1$^+$CD44$^+$CD24$^{-/lo}$LINEAGE$^-$ cells consist solely of expanded numbers of B38.1$^+$CD44$^+$CD24$^{-/lo}$LINEAGE$^-$ cells.

Tumors arising from 1,000 B38.1$^+$CD44$^+$CD24$^{-/lo}$LINEAGE$^-$ cells were dissociated and analyzed by flow-cytometry with respect to B38.1, CD44 and CD24 expression (FIG. 10). As expected from the deterministic solid tumor stem cell mode, cells obtained from a tumor arising from transplanted B38.1$^+$CD44$^+$CD24$^{-/lo}$LINEAGE$^-$ cells were heterogeneous with respect to expression of all markers (FIG. 10C and FIG. 10F). In both cases, the marker expression pattern of the cells isolated from the tumor initiated by the B38.1$^+$CD44$^+$CD24$^{-/lo}$LINEAGE$^-$ cells was similar to that of the original tumors (compare FIG. 10A and FIG. 10B with FIG. 10C and FIG. 10F) none of the B38.1$^+$CD44$^+$CD24$^+$LINEAGE$^-$ population, gave rise to new tumors.

We tested whether the tumors formed by B38.1$^+$CD44$^+$CD24$^{-/lo}$LINEAGE$^-$ cells contained tumorigenic B38.1$^+$CD44$^+$CD24$^{-/lo}$LINEAGE$^-$ cells in addition to other non-tumorigenic cells. B38.1$^+$CD44$^+$CD24$^{-/lo}$LINEAGE$^-$ cells or B38.1$^+$CD44$^+$CD24$^+$LINEAGE$^-$ cells were isolated from second passage T1 tumors that had been initiated by injections of 1,000 B38.1$^+$CD44$^+$CD24$^{-/lo}$LINEAGE$^-$ cells seven weeks earlier. 1,000 cells were used per injection into each of four animals in an attempt to establish third passage tumors. As with the original T1 and T2 tumors, all four of the injections of B38.1$^+$CD44$^+$CD24$^{-/lo}$LINEAGE$^-$ population, but none of the B38.1$^+$CD44$^+$CD24$^+$LINEAGE$^-$ population gave rise to new tumors.

This EXAMPLE demonstrates that the B38.1$^+$CD44$^+$CD24$^{-/lo}$LINEAGE$^-$ population gives rise to both additional tumorigenic B38.1$^+$CD44$^+$CD24$^{-/lo}$LINEAGE$^-$ cells and phenotypically distinct non-tumorigenic cells.

EXAMPLE 11

Expression of Potential Therapeutic Targets by the Different Populations of Neoplastic Cells In the deterministic solid tumor stem cell model (FIG. 1B), expression of genes by the tumorigenic and non-tumorigenic populations of tumor cells may differ. Accordingly, the inability of current cancer treatments to significantly improve outcome is due to the tendency of therapeutics to target non-tumorigenic cells but not the rare tumorigenic solid tumor stem cells. If only the non-tumorigenic populations are killed by particular therapies, then tumors may shrink, but the remaining tumorigenic solid tumor stem cells can drive regrowth of the tumor.

We examined first passage T1 cells for expression of either the EGF receptor (EGF-R) or HER2/neu. The EGF-R and HER2/neu are potential therapeutic targets that have been implicated in breast cancer cell proliferation. Tumorigenic T1 cells stained with lower levels of anti-EGF-R antibody than non-tumorigenic cells, and EGF-R expression could not be detected at the single cell level in tumorigenic cells (FIG. 11).

Figure 11B:
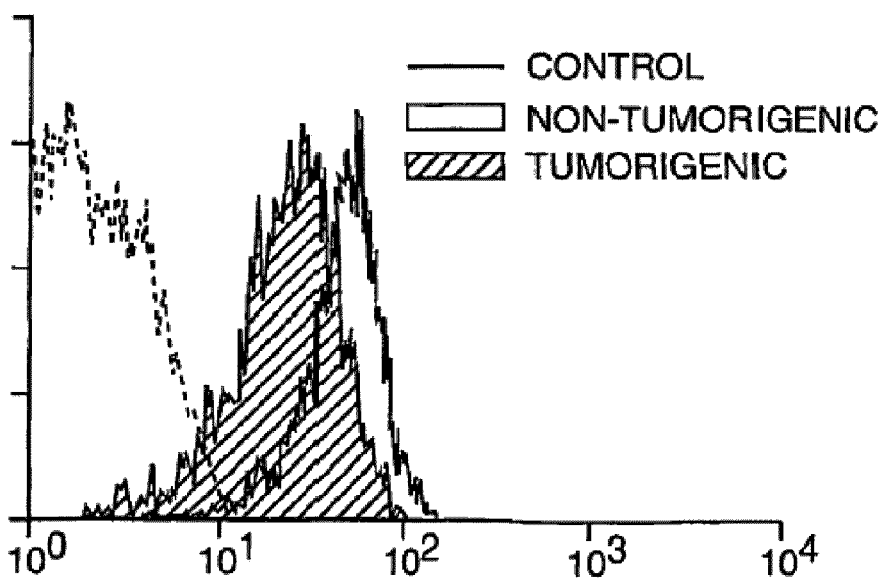

To test whether cells that did not express detectable levels of the EGF-R were tumorigenic, 1,000-2,000 EGFR$^-$B38.1$^+$CD24$^-$LINEAGE$^-$ cells were injected into NOD/SCID mice. Tumors formed in four out of four cases, continuing that the EGF-R$^-$ cells are tumorigenic. By contrast, we could not detect a substantial difference in HER2/neu expression between tumorigenic and non-tumorigenic T1 cells (FIG. 11B and FIG. 11E).

As expected from the solid tumor stem cell model, 1,000-2,000 HER2/neu$^+$B38.1$^+$CD24$^-$ LINEAGE$^-$ cells gave rise to tumors in four out of four cases. This EXAMPLE shows that there can be differences in the expression of therapeutic targets between the tumorigenic and non-tumorigenic populations.

These experiments serve as a proof-of-principle of our stem cell model of solid cancer and demonstrate the following:

(a) tumor cells are phenotypically and functionally heterogeneous;

(b) by separating cells by FACS one can enrich for tumorigenic cells; and (c) by studying the tumorigenic fractions, one can isolate solid tumor stem cells to more carefully focus molecular and biological assays.

EXAMPLE 12

Further Evidence for a Role for Notch in Breast Cell Proliferation

To determine whether Notch was a solid tumor stem cell marker, we sorted Notch $4^+$ and Notch $4^-$ cells and analyzed their ability to form colonies in vitro. Surprisingly, neither population grew in tissue culture.

Figure 12:
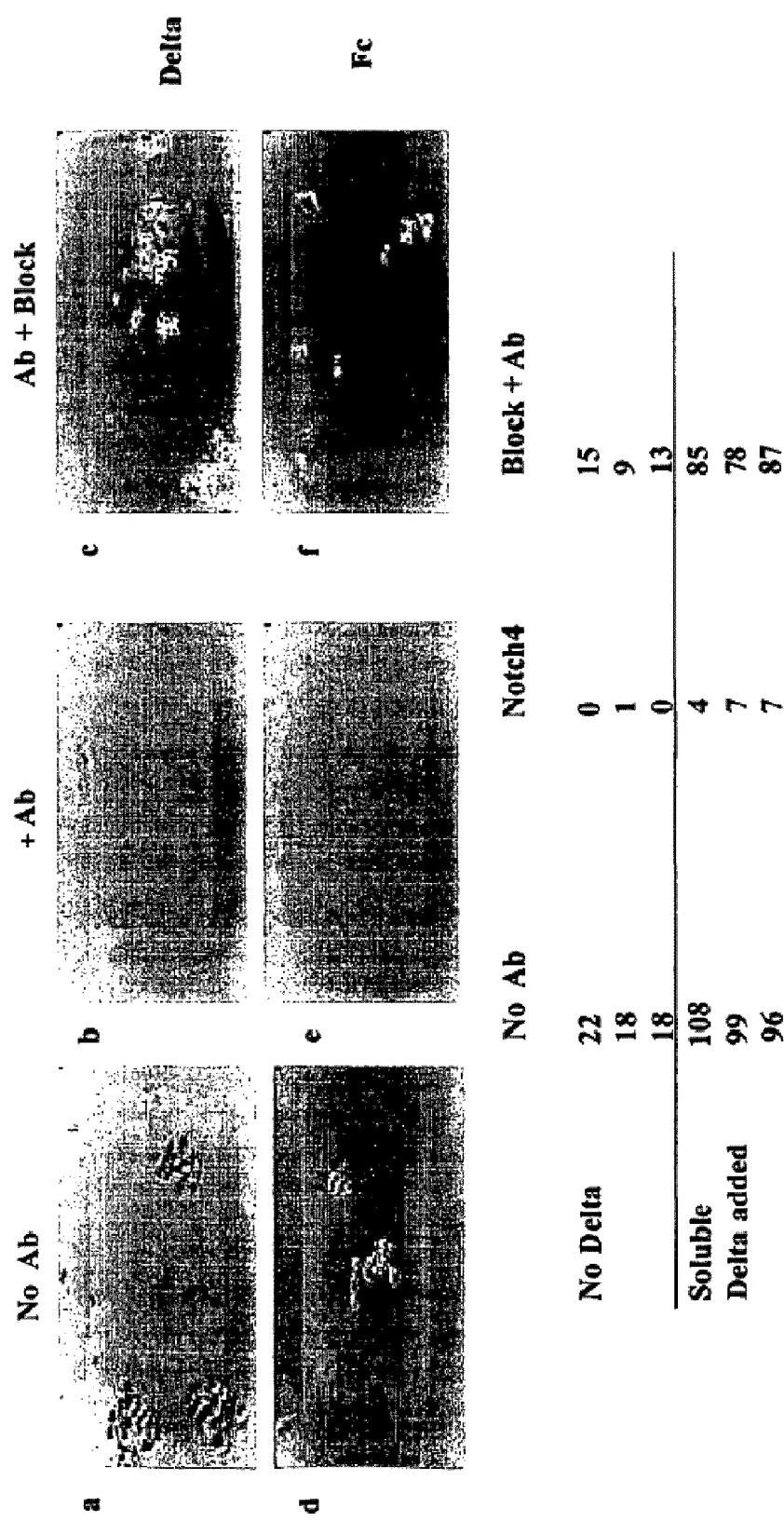
FIG. 12 is a photomicrograph of breast cancer cells placed in tissue culture after exposure to an anti-Notch 4 antibody. Cells were incubated on ice for one hour in HBSS with or without soluble Delta but no anti-Notch 4 antibody, with anti-Notch 4 antibody, or with anti-Notch 4 antibody that had been preincubated with the peptide used to generate the antibody. The number of colonies that formed in the triplicate experiments is shown. Soluble Delta was added to the culture. Fc-control medium without soluble Delta was added to the culture. Symbols: Ab=the anti-Notch 4 antibody; Block=the peptide used to generate the anti-Notch 4 antibody.

There are two possible explanations for these results. First, interaction between the two populations of cells may be required for cell growth. Alternately, the antibody may be either an agonist or antagonist of Notch 4 and inhibition or activation of the receptor may inhibit tumor cell growth. To distinguish between these possibilities, unseparated tumor cells were incubated with the anti-Notch 4 antibody, and then assayed for the ability to form colonies in vitro in tissue culture medium containing soluble Delta, a Notch ligand. Delta was essential for colony formation from cells isolated from this tumor. While control cells grew in tissue culture and formed colonies (FIG. 12A), cells incubated with the Notch 4 antibody did not grow (FIG. 12B). When the anti-Notch 4 antibody was pre-incubated with the peptide used to generate the antibody (this peptide should theoretically block binding of the antibody to the cells), the ability of the tumor cells to form colonies was restored (FIG. 12C). An anti-Notch 2 antibody did not affect colony formation.

To confirm that Notch regulates colony formation by tumor cells, cells were incubated in medium with or without soluble Delta (FIG. 12A and FIG. 12D, respectively). The cultures with Delta formed many colonies (FIG. 12A), whereas only a few small colonies formed in medium lacking soluble Delta or in cultures using cells exposed to the anti-Notch 4 antibody (FIG. 12B, FIG. 12D, and FIG. 12E). Taken together, these data suggest that the Notch 4 pathway regulates the proliferation/survival of breast cancer cells in cells and that the anti-Notch 4 antibody blocks activation in vitro.

We also tested whether the anti-Notch 4 antibody inhibits breast cancer tumor cell growth in vivo. To do this, 20,000, 10,000 or 5,000 tumorigenic cells were incubated with the anti-Notch 4 antibody or the anti-Notch 4 antibody and the blocking peptide. The antibody delayed the appearance of the tumors by one week when either 20,000 or 10,000 tumorigenic cells were injected, and by 13 days when 5,000 cells were injected. This suggests that the antibody may block tumor formation in vivo.

We then tested four breast cancer cell lines for expression of Notch 4 and growth inhibition by the anti-Notch 4 antibody. We found that the MCF-7 and the SKBR-3 breast cancer cell lines expressed Notch 4 and that the anti-Notch 4 antibody inhibited the growth of these cells. RT-PCR showed that both expressed Notch 4. To determine whether the anti-Notch 4 antibody inhibits growth, 5,000 MCF-7 cells were incubated with the anti-Notch 4 antibody, the anti-Notch 4 antibody and the peptide used to generate the antibody, or an irrelevant control antibody. The anti-Notch 4 antibody, inhibited colony formation of both cell lines by more than ten-fold.

This EXAMPLE shows that Notch 4 activation promotes proliferation/survival of solid tumor stem cells and that the anti-Notch 4 antibody blocks receptor activation.

EXAMPLE 13

Targeting Breast Cancer Stem Cells with a Gene Therapy Suicide Vector

Figure 13:
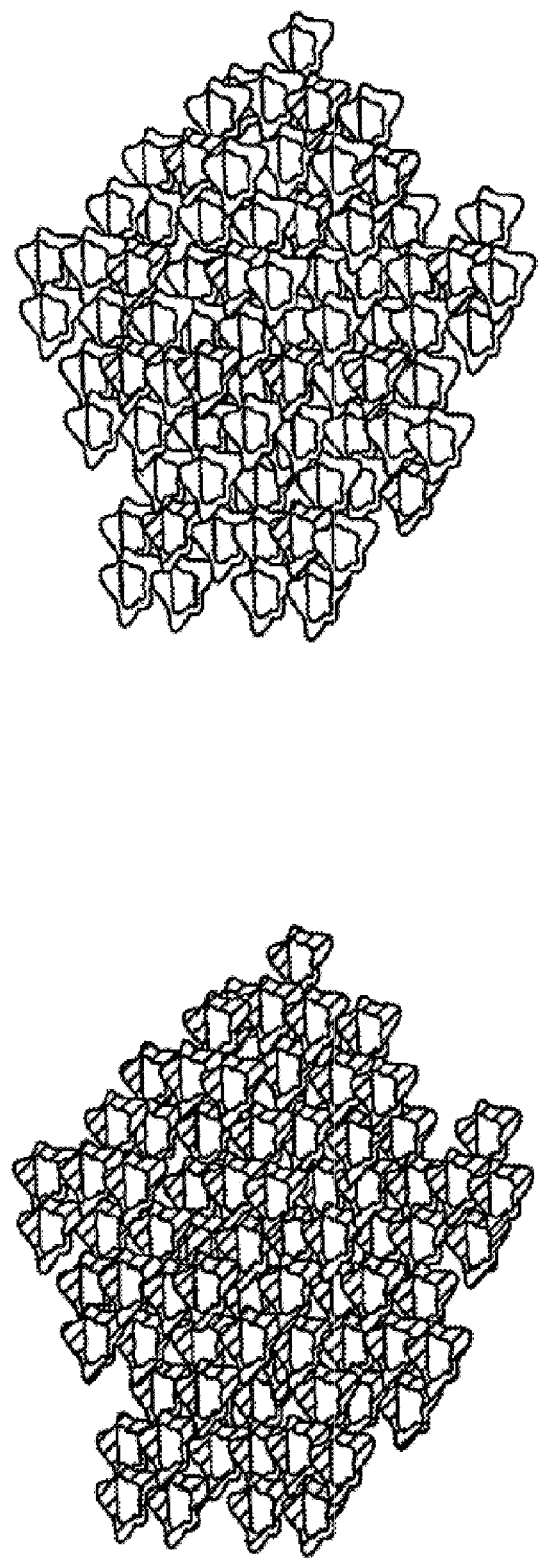
FIG. 13 is a schematic diagram of B38.1$^+$ cells within a tumor. The breast cancer stem cells from multiple patients are B38.1$^+$. To successfully treat a cancer with a gene therapy approach, these cells can be targeted with a vector.

The breast cancer stem cell comprises a minority of the tumor cells in a breast tumor. It is an object of the invention that gene therapy strategies target these cells (FIG. 13).

We targeted virus vectors to breast cancer stem cells using markers expressed by stem cells. To do this, we stained different cell lines with the B38.1 antibody and analyzed them by flow cytometry. MCF7, SKBR3, T47D and BT474 breast cancer cell lines were highly positive.

Figure 14:
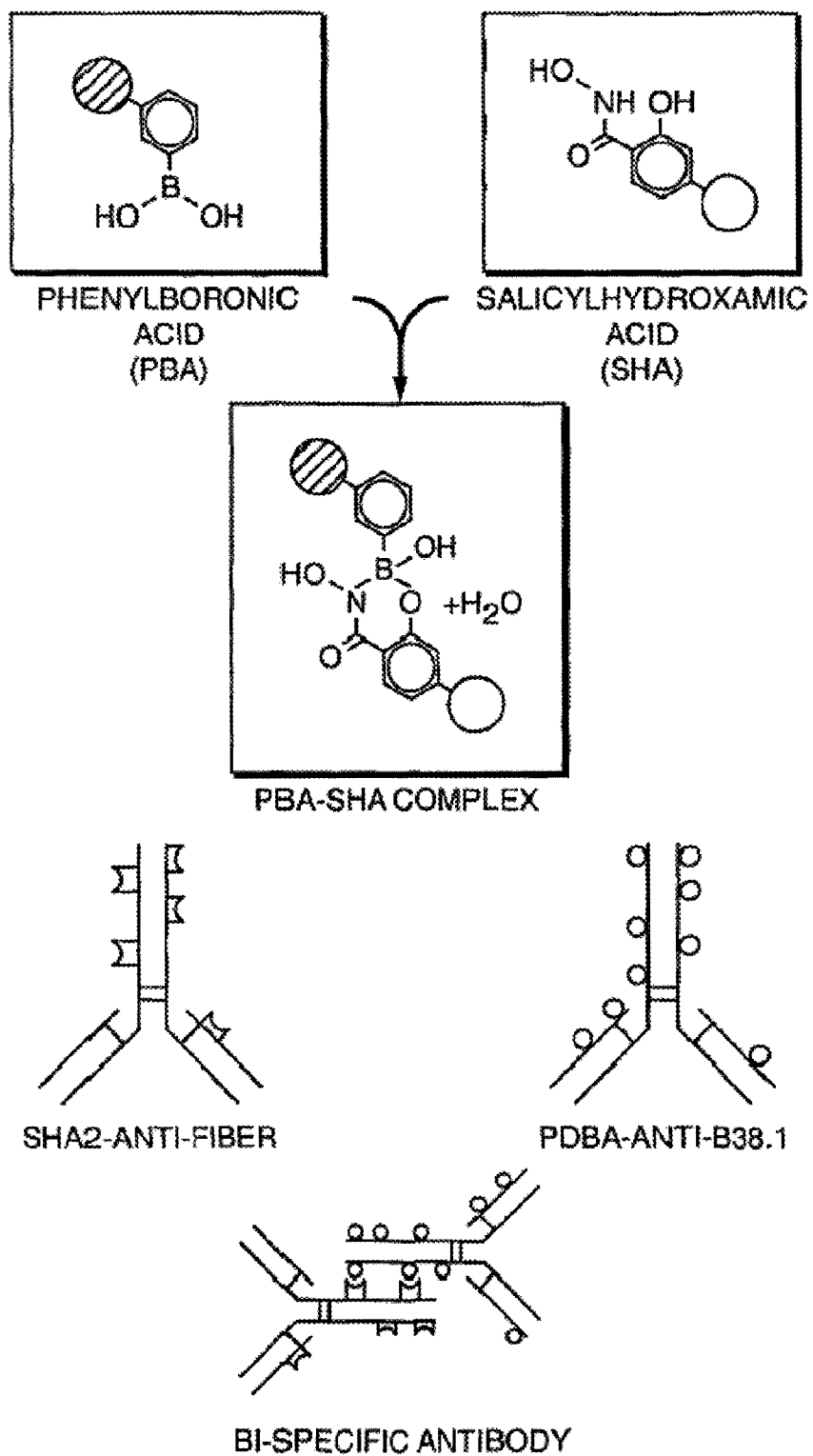
FIG. 14 is a description of the method for obtaining the bi-specific conjugate and the chemical modifications introduced in the antibodies.
Figure 15:
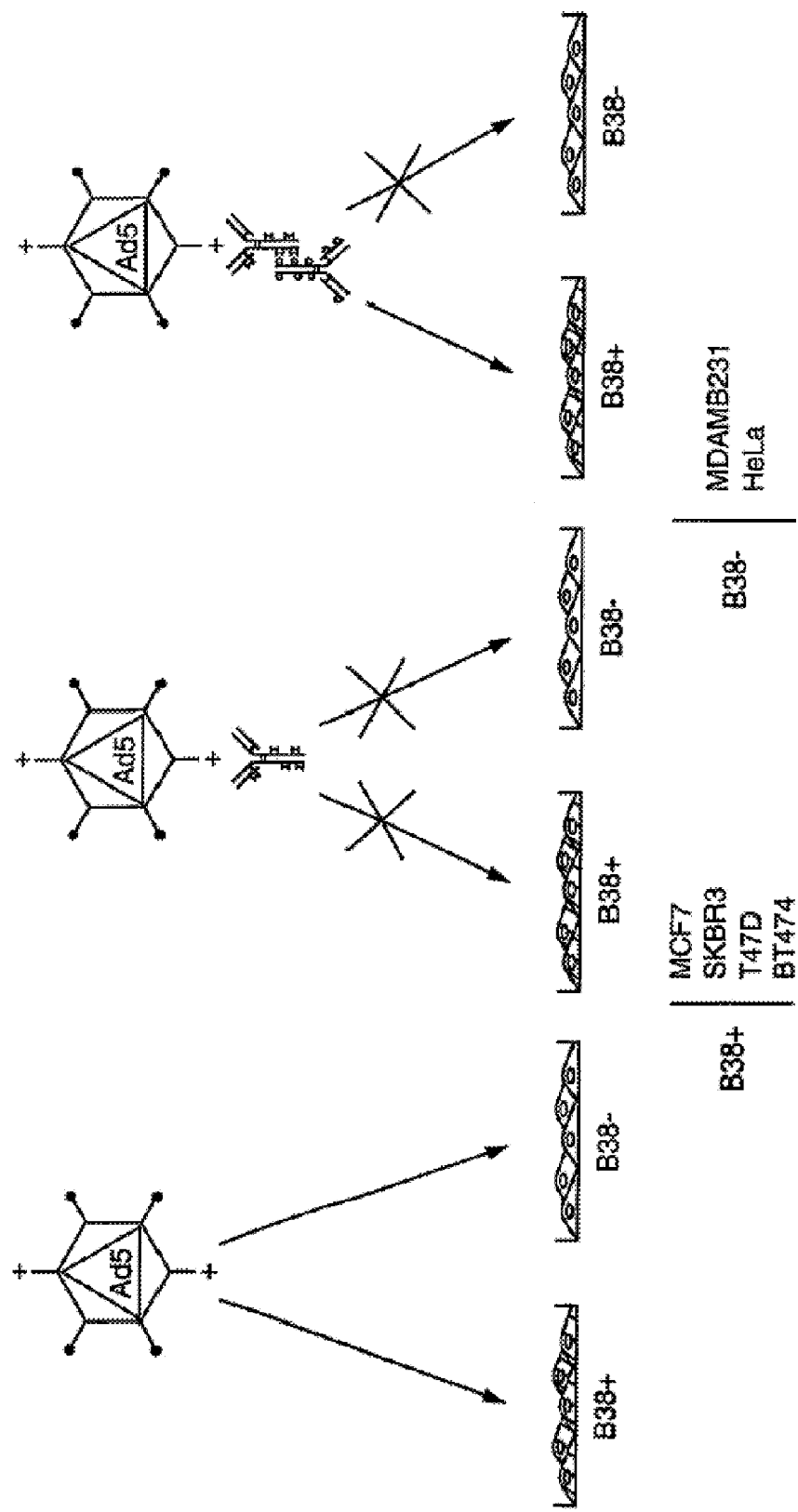
FIG. 15 is a strategy for re-targeting Adenovirus. The LaZ virus can infect most of the cells from a tumor. After the LaZ virus is incubated only with the anti-fiber antibody, the LaZ virus loses ability to infect all of the cells. After the LaZ virus is incubated with the bi-specific conjugate, the B38.1 moiety of the molecule allows the attachment of the virus to the B38.1$^+$ cells, so only these cells are infected.
Figure 16:
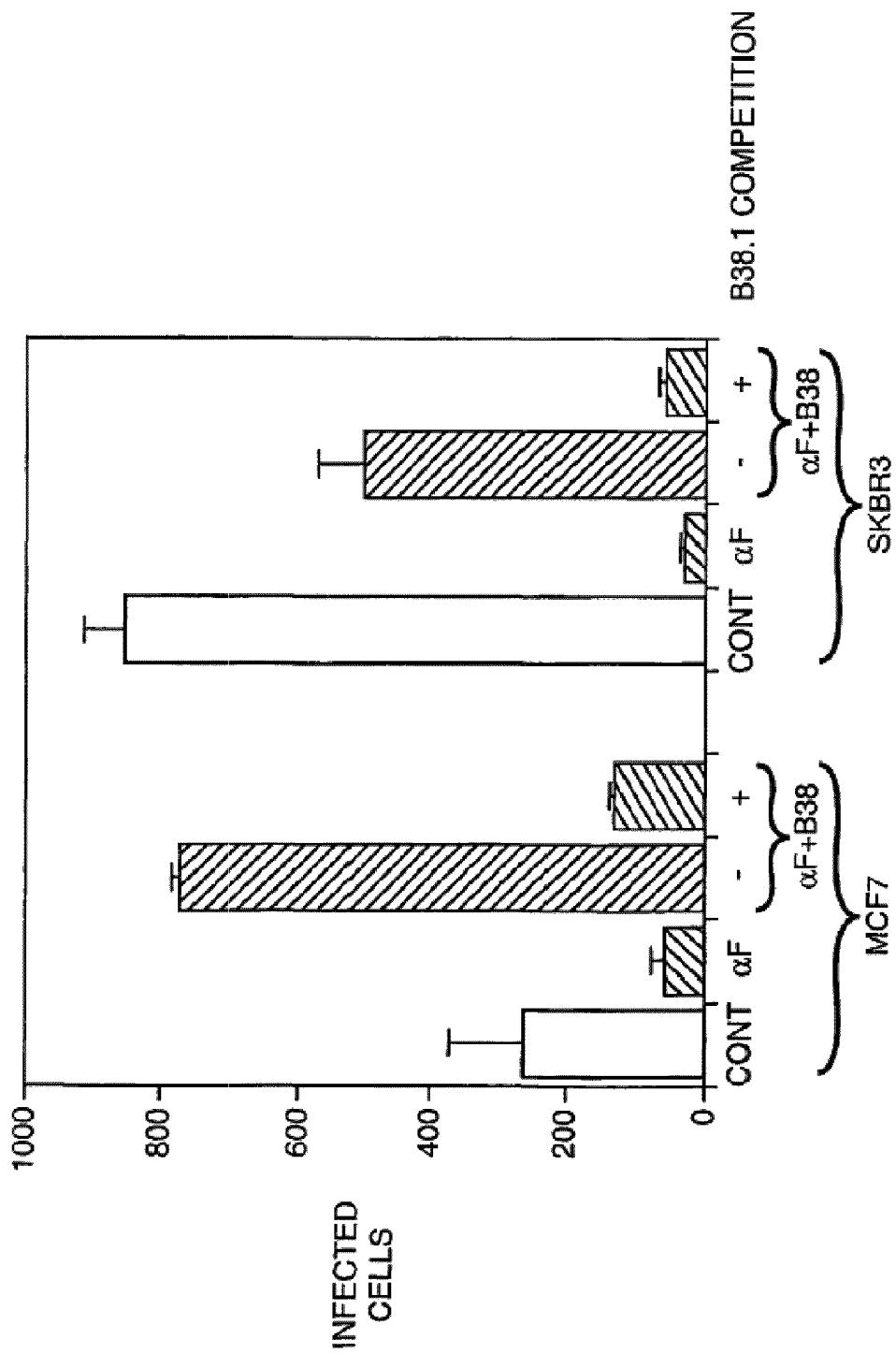
FIG. 16 shows the targeting of breast cancer stem cells with the bi-specific antibody. Different cell lines were infected with AdLaZ, which is an E1-deleted Adenovirus that expresses the β-galactosidase gene (gray columns, control for virus infection). In some cases, the virus was incubated with the anti-fiber antibody for 30 min before infection (yellow columns). In other cases, the virus was incubated with the bi-specific conjugate (green columns). After 24 hr of infection, the monolayers were fixed and incubated with X-Gal-contained buffer. The infected cells are blue, and the graphic shows the percentage of blue cells obtained, relative to the control infection (i.e., the reduction or increase in infectivity of the virus after incubation with the different antibodies).
Figure 17:
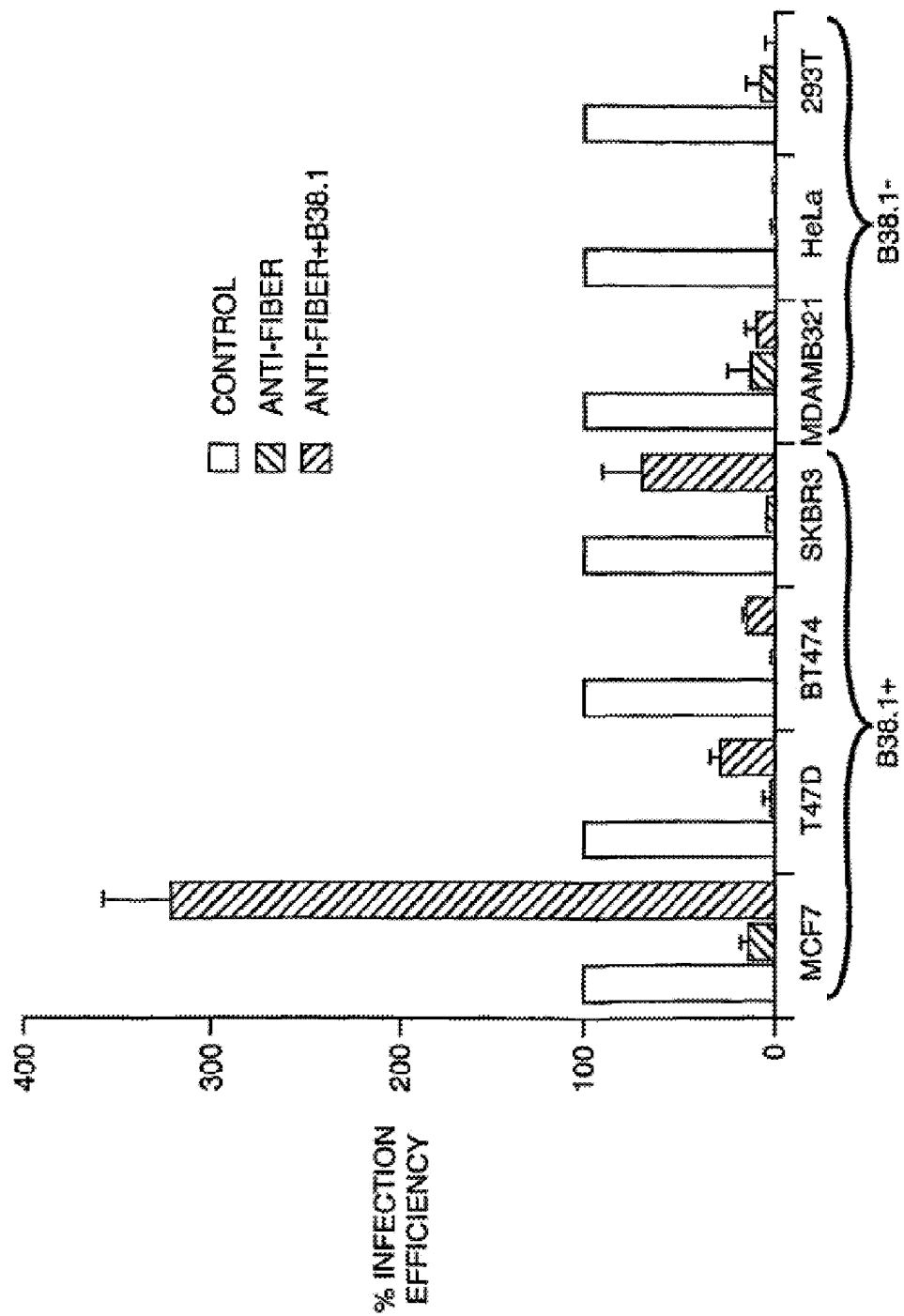
FIG. 17 shows that the bispecific antibody can target an adenovirus vector to breast cancer stem cells. The columns represent the absolute number of infected cells per field. Gray: the indicated cells infected with the control adenovirus. Yellow: the indicated cells were infected with the adenovirus that had been incubated with the anti-fiber antibody. Green: the indicated cells were incubated with the bi-specific conjugate antibody. Red: cells were infected with the virus that had been incubated with the bi-specific conjugate antibody, but the cells were pre-treated with an excess of B38.1 antibody.
Figure 18:
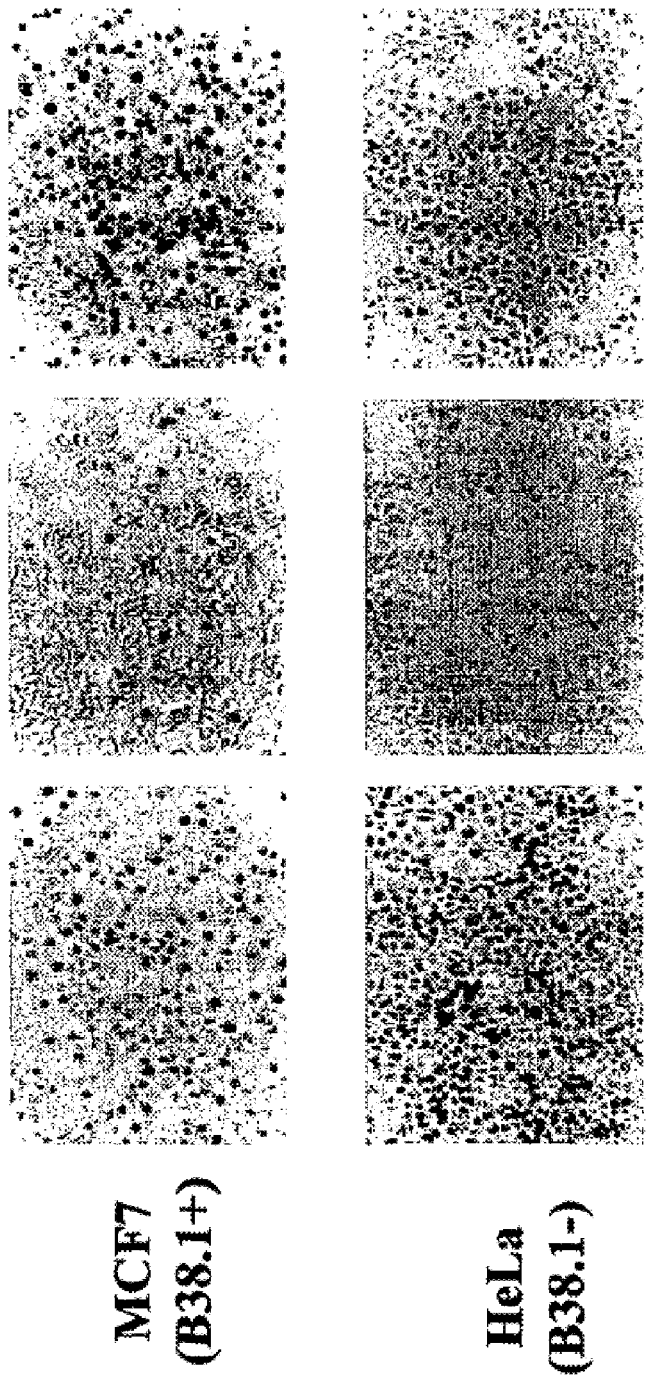
FIG. 18 is a photograph of some of the cell monolayers after X-Gal staining. The infected cells appear like dark dots in this black and white picture (the β-galactosidase gene of the LaZ virus has a nuclear localization signal. The staining is in the nuclei of the cells.

We had the anti-fiber and the B38.1 antibodies conjugated with the Prolinx (Prolinx, Inc., Bothell, Wash., USA) method (FIG. 14, see Douglas J T et al., Nature Biotechnology. 14(11):1574-8 (1996)). When we mixed the modified anti-knob and anti-B38.1 antibodies together, they became cross-linked and generated the bi-specific conjugate (FIG. 15). The anti-fiber antibody part of the conjugate binds to the adenovirus, while the anti-B38.1 moiety binds to the breast cancer stem cell. Incubation of the AdLacZ virus with the anti-fiber alone blocks the infectivity of the virus (FIG. 16). If we incubate the virus with the bi-specific conjugate, the infectivity is restored only in the cells that express high levels of the B38.1 antigen (FIG. 18). The re-targeting is specific, because it can be inhibited by free B38.1 antibody (FIG. 18).

The conclusion is that the new bi-specific conjugate modifies the infectivity of Adenovirus, blocking its natural tropism and directing the infection to cells that express the breast cancer stem cell surface marker.

EXAMPLE 14

Downstream Targets in the Breast Cancer Stem Cells

The methods used in this EXAMPLE provide guidance for the development of Notch-related and other anti-cancer therapies using the cancer stem cells of the invention. We use array technology to begin to understand the molecular pathways that might be regulated by Notch-signaling induced by specific Notch ligands. Sequence verified human cDNAs from Research Genetics, provided by the University of Michigan Microarray Network, are arrayed by the Cancer and Microarray Facility. Probes are prepared from self-renewing breast cancer stem cells or cells from the various populations of cells found in a tumor. Probes are hybridized to the arrays and the hybridization patterns are read by the Cancer and Microarray Facility. We then analyze the hybridization patterns to identify genes that hybridize to probe from the breast cancer stem cells stimulated with various Notch ligands and non-stimulated cells. Such genes may represent those that are involved in the regulation of breast cancer cell survival or self-renewal.

Preparation of microarrays. We have used the microarray technology to analyze gene expression of hematopoietic stem cells. We now extend this work to cancer stem cells.

The University of Michigan Microarray Network currently has 32,500 sequence verified human cDNAs from Research Genetics. A "cancer" chip has been assembled in collaboration with the NCI. This chip contains a comprehensive constellation of 1,200 genes involved in proliferation and tumorigenesis. There is also an "apoptosis chip" developed by the University of Michigan that contains all genes known to be involved in programmed cell death. Note that the HES genes, known to be downstream targets of Notch, are included in the arrays.

Preparation of probe from breast cancer stem cells. Messenger RNA is isolated either from freshly purified breast cancer stem cells or from breast cancer stem cells incubated in the presence or absence of various Notch ligands. The RNA is amplified if necessary, such as by PCR or linear RNA amplification Wang et al., Nature Biotechnology. 18: 457-459 (April 2000). Probe are prepared by reverse transcription from an oligo-dT primer, and labeled by incorporating CY3 or CY5 conjugated nucleotides. Gene expression profiles are examined using probe prepared from freshly isolated, uncultured breast cancer cells, as well as from cultured breast cancer cells, such as cells that have been exposed to the appropriate Notch ligands, including Fringe family members, either singly or in combination as determined by which ligands are expressed by the different populations of tumor cells. To do these assays, we expose the cells to a soluble form of Delta or Jagged family members in which the transmembrane region has been deleted, or one of the Fringes. The Fringes are secreted proteins. We make recombinant protein of each Notch ligand of the Delta, Jagged and Fringe families from insect cells or mammalian cells transfected with a baculovirus or mammalian expression vector, respectively.

Comparisons of gene expression patterns between control breast cancer tumorigenic cells and tumorigenic cells exposed to various Notch ligands are made. Probe from breast cancer stem cells from each tumor is combined with probe labeled with a different fluor made from cultured breast cancer stem cells exposed to various Notch ligands to compare their hybridization patterns. To do this, breast cancer stem cells are isolated by FACS. Cells are seeded at single cell density to preclude Notch interactions between cells. Cells are exposed to soluble forms of Delta (see, EXAMPLE 6), Delta-like, Jagged 1, Jagged 2, or each of the Fringes. Cells are exposed to each protein both alone and in combinations suggested by the Notch-ligand expression pattern of individual cell populations. The microarrays hybridized with probe from each test condition are compared and analyzed to gain insights into molecular pathways affected by Notch ligand interactions. For example, if a particular population of cells expresses Delta and Manic Fringe, then one group of breast cancer stem cells is exposed to Delta alone, a second to Delta and Manic Fringe and a third to Manic Fringe alone. cDNA is made from each population with CY5 or CY3 labeling, and used to probe a microarray chip. In addition, cDNA from each population is used with cDNA made from cells cultured in control medium and freshly isolated breast cancer cells to probe a microarray chip. Each group is compared 5 times to assure that any differences in expression profiles of the arrayed genes by each test groups are real.

Preparation of probe from cells treated with the anti-Notch 4 antibody. An antibody against Notch 4 inhibits growth in vitro and tumorigenesis in vivo. This effect could be explained if the antibody acts as either a Notch-4 agonist or antagonist. Since soluble Delta promotes cancer cell growth in vitro, the antibody most likely is a Notch 4 antagonist. To confirm the mechanism by which the anti-Notch 4 antibody inhibits tumor growth, probe is made from cells incubated in the presence or absence of the anti-Notch 4 or control irrelevant antibody and the various combinations of the Notch ligands and used for microarray expression analysis as described above. Another control group includes cells incubated with the antibodies and no Notch ligand. Each comparison is performed in at least six independent tests employing independently prepared batches of probe. By comparing the gene expression patterns of each group, we should be able to determine how the anti-Notch 4 antibody affects Notch signaling.

Making the cDNA probe. 1-2 µg of mRNA is commonly used to synthesize probe for screening gene expression profiles on microarrays (Wang et al., Nature Biotechnology. 18: 457-459 (April 2000)). Since we screen a set of three slides (containing a total of 32,500 cDNAs) in each test, 6 µg of mRNA is required per assay (reverse transcription of 6 µg of mRNA should yield around 3 µg of cDNA probe, or 1 µg of probe per slide). Cancer cells tend to have a high RNA content. In past assays, $10^7$ cancer cells yielded around 100 µg of total RNA, which in turn yielded around 3 µg of poly $A^+$ RNA. Thus in order to generate 6 µg of mRNA, around $2 \times 10^7$ cells would be required. As described in the preliminary data, that number of flow-cytometrically purified breast cancer stem cells can be isolated from approximately five-ten 1 cm tumors.

The breast cancer stem cells represent approximately 5% of the total number of cells within a tumor. It is not practical to isolate more than $10^6$ freshly dissociated (uncultured) breast cancer stem cells by flow-cytometry in one day. This would yield less than 0.5 µg of mRNA from one day of sorting. While breast cancer stem can be combined from multiple days of sorting to pool enough mRNA to prepare probe from freshly isolated cells, it may not be practical to perform all assays in this manner. Some assays require brief periods of tissue culture. Plating efficiency of the sorted cells is approximately 10%. Thus it may be necessary to enzymatically amplify the template prior to synthesizing probe. This can be done either by PCR or by linear amplification of RNA using T7 RNA polymerase. Our protocol employs 15-18 rounds of PCR to amplify cDNA from small numbers of stem cells. This protocol was used to construct a high quality hematopoietic stem cell (HSC) cDNA library and to make probe from hematopoietic stem cells. To produce probe from freshly isolated breast cancer stem cells, we test the same approach. Alternately, a number of groups have reported success in using linear RNA amplification to produce probe for microarray hybridization. Thus we compare the two methods by preparing probe both ways and examining the hybridization patterns that result. cDNA is primed using an oligo-dT primer that contains a T7 RNA polymerase binding site and synthesized by Superscript reverse transcriptase (Gibco) and the Clontech 5's switch oligomer that allows the tagging of the $5^+$ end of the cDNA. Second strand cDNA is synthesized using *E. coli* DNA polymerase. Then amplified RNA (aRNA) is produced using T7 RNA polymerase or PCR. Which of the two that amplification methods are used is determined by comparing probe made with standard cDNA synthesis. After preparing aRNA, cDNA is re-synthesized using random hexamers. This cDNA can then be used for probe, or if necessary, additional rounds of amplification can be performed. Both approaches are used to prepare probe from 40,000 MCF-7 cells (a human breast cancer stem cell line). This probe is hybridized to human cDNA microarrays along with probe from unamplified MCF-7 cells. The amplification approach that most closely reproduces the hybridization pattern of the unamplified probe is selected. Then amplification conditions are modified until the amplified probe reproduces the hybridization pattern of the unamplified probe as closely as possible.

Analysis of the hybridization pattern. Hybridization patterns are analyzed in the Cancer and Microarray Core facility using their laser scanning system. The use of an integrated system for arraying, hybridizing, scanning, and analyzing hybridization patterns in which all components are provided by Genomics Solutions permits a seamless and efficient analysis of hybridization patterns.

A transcript is differentially expressed if there is at least a 3-fold difference in normalized hybridization levels between probes. Hybridization signals from CY3 and CY5 labeled probes within a single test are normalized to each other to correct for potential differences in the effective concentration of each probe and replicates of each test are done using the opposite fluor for each group to correct for differences in the amounts or labeling efficiencies of probes.

Verification of differential expression. cDNAs that consistently hybridize to probe from groups of cells but not to probe from the control groups of cells are further characterized. The sequences of these cDNAs are obtained from the Microarray Network. Two approaches are used to confirm the differential expression of candidate genes between cell populations. The first is to prepare in situ hybridization probes against candidate genes, and then perform in situ hybridizations on breast cancer stem cells cultured in medium with or without various Notch ligands as described above. In situ hybridizations are then performed on cultured cells. The advantage of this approach would be that expression could be compared at the level of individual. cells.

An alternate approach is to design nested PCR primers against candidate genes, and to perform RT-PCR on multiple 1-10-cell aliquots of freshly purified breast cancer stem cells (isolated as described above). By performing RT-PCR on small numbers of cells it is possible to observe a difference in the ability to amplify particular transcripts, even if the "non-expressing" population contains rare expressing cells. We used this approach to demonstrate the differential expression of RGS18 between different subpopulations of multipotent hematopoietic progenitors.

Differential expression can be confirmed by Northern analysis. Poly A+ RNA from $1-2 \times 10^7$ breast cancer stem cells cultured with or without the Notch ligands, are hybridized-to probes of the differentially expressed cDNAs. Hybridization signals are quantitatively compared between these samples.

We then confirm that genes are differentially expressed at the protein level. In cases where immunocytochemical staining is uninformative we also perform western blots on protein from the different cells.

Certain molecular analyses are difficult using the primary breast cancer cells that only proliferate for prolonged periods of time in the xenograft model. These analyses can be done in cell lines. One can use any of a large number of breast cancer cell lines, including early passages of lines that we have studied in the past. Clarke et al., *Proc. Natl. Acad. Sci. USA.* 92: 11024-28 (*November* 1995); Hernandez-Alcoceba et al., *Human Gene Therapy.* 11(11): 20 (September 2000). These cell lines are plated at single-cell density with and without various Notch ligands, as well as the anti-Notch 4 or control antibodies as described in the assays with the primary breast cancer cells. If clonogenicity is affected by Notch signaling, then probe for the microarray analysis is made using cDNA made from the cell line incubated in medium with or without the various Notch ligands or anti-Notch 4 or control antibodies. Since a virtually unlimited number of cells can be analyzed, we can make probe that has not been amplified.

Finally, cell lines are useful for confirming whether the anti-Notch 4 antibody is an agonist or antagonist. If a cell line is identified that clonogenicity is enhanced by soluble Delta and inhibited by the anti-Notch 4 antibody, then it is used in these assays. The cells are stably transfected with a luciferase minigene under the control of the Notch-inducible HET-1 promoter. Jarriault et al., Molecular & Cellular Biology. 18(12): 7423–31 (December 1998). The cells are plated at single cell density to prevent cell-cell Notch-Notch ligand interactions. They are treated with the various combinations of Notch ligands and either the anti-Notch 4 antibody or a control antibody. The cells are harvested and a luciferase assay is done to determine how each condition affects Notch signal transduction as reflected by transactivation of the HET1 promoter.

A comprehensive functional analysis of candidate genes that emerge from the microarray analysis can be performed. Full-length cDNAs are isolated and cloned into a retroviral expression vector. Breast cancer cell lines and breast cancer stem cells isolated from the five xenograft tumors are infected in vitro and the effect of the retroviral transgene on self-renewal and tumorigenicity is assayed relative to clones infected with a control vector. The transgene is expressed as a bicistranic message that contains IRES-GFP. This allows identification of transduced cells via FACS or fluorescent microscopy. The effect of the transgene on Notch signaling is examined in vitro and in vivo. To do this, transduced cells are tested for response to the various combinations of Notch ligands found to affect colony formation in tissue culture and tumorigenicity in mice.

The expression patterns of candidate genes are examined in detail in vivo to determine how widely the genes are expressed beyond the xenograft. In addition to performing more extensive in situ hybridizations of tissue sections from slices of primary breast cancer, we make antibodies against selected gene products being studied. The Hybridoma Core facility at the University of Michigan has extensive experience preparing monoclonal antibodies using both peptides, and expressed recombinant proteins.

Ultimately, the functions of unknown genes are tested in vivo, using gene targeting to make knockout mice. The University of Michigan Transgenic Core has established murine ES cell technology, they provide ES cells that 'go germline at a high rate and assist with the generation of homologous recombinant ES clones.

The ability of microarray analysis to simultaneously compare the expression of many genes provides unparalleled power to screen for changes in gene expression patterns. Combined with the ability to purify stem cells and to regulate their self-renewal and differentiation in vitro, microarray analyses can be applied with great precision to screen for specific types of regulatory genes.

EXAMPLE 15

How Notch Signaling Affects Breast Cancer Tumorigenesis

To verify the importance of Notch in normal mammary growth and development, we test the effects of Notch ligands or agonist peptides on the growth and tumor formation of mammary tumor stem cells.

Effect of Notch activation on tumor formation in vivo. The effects of the various combinations of Notch ligands on tumor formation are correlated with the microarray data obtained in EXAMPLE 14. These assays are done using xenograft tumor cells before and after enrichment of populations of malignant breast cells, allowing us to differentiate Notch effects on both stem and progenitor cells respectively. The effects of Notch ligands on growth and differentiation of each population of cancer cells are determined utilizing the in vivo assay.

To determine the effect of Notch stimulation on tumor growth in vivo, one thousand, ten thousand, and one hundred thousand breast cancer tumor cells are incubated with soluble Notch ligands, alone or in combination, or control media and then injected (6 replicates of each) into NOD/SCID mice. The soluble forms of Delta, Delta-like, Jagged 1, and Jagged 2 are used as well as members of the Fringe family. The cells are incubated with each ligand individually, as well as combinations of different ligands, for two hours. The cells are suspended in Matrigel® with the Notch ligands and then injected into the mice. The effects of each ligand of Notch stimulation on both the number of cells needed to form a tumor as well as the time needed to form a tumor are determined. This allows us to determine whether Notch affects tumor growth in vivo.

In previous EXAMPLES, the anti-Notch 4 antibody retarded tumor formation after a single, brief incubation with cells. Next, one thousand, ten thousand, and one hundred thousand tumorigenic cells from each of the five xenograft tumors are incubated with either a control antibody or the anti-Notch 4 antibody alone, or with various combinations of Delta, Jagged and Fringe family proteins. Each group is then mixed in Matrigel® containing the same antibody or Notch ligands and injected into mice. The effects of the anti-Notch 4 antibody on the number of cells and time needed to form a tumor are measured. The results are correlated with the microarray expression data, obtained in EXAMPLE 14.

Stimulation of Notch should drive the proliferation of the normal breast stem cells. Like in normal stem cells, members of the Fringe family should modulate Delta or Jagged signaling. Notch should also play a role in the self-renewal of the breast cancer stem cell.

EXAMPLE 15

Human Subjects

The following human sources of material are obtained for use in the methods of diagnosis of the invention: (1) primary tumors from patients with breast cancer and (2) pleural fluid from patients with metastatic breast cancer. A portion of the tumor or the pleural fluid is obtained during routine treatment when the patient's physician deems removal of the tumor or pleural fluid to be clinically indicated.

For example, at the University of Michigan Hospital, there is an IRB approved protocol to obtain the specimens. Patients are asked to sign an informed consent where indicated. There are no additional risks to patients.

EXAMPLE 16

Vertebrate Animals

The University of Michigan complies with the Animal Welfare Act as amended (7 U.S.C. §2131 et seq.), and other Federal statutes and regulations relating to animals. We use the laboratory mouse strain NOD/SC1D mice and other strains of immunocompromised mice, such as Beige/SCID mice.

There should not be any discomfort from cancer cell growth, because mice undergo euthanasia prior to development of illness. If the mice do show evidence of discomfort from tumors (posture, appetite, or behavior changes, weight loss), they can be immediately sacrificed. Should the mice show evidence of more than mild discomfort (posture, appetite, or behavior changes) they are given analgesics such as oral morphine or codeine. Mice have bone marrow cells inoculated into their retro-orbital vein while anaesthetized with either ether or a similar general anesthetic agent.

Mice are killed by the use of $CO_2$, which is consistent with the recommendations of the Panel on Euthanasia of the American Veterinary Medical Association. This method was chosen because it is safe and humane.

EXAMPLE 17

Figure 19:
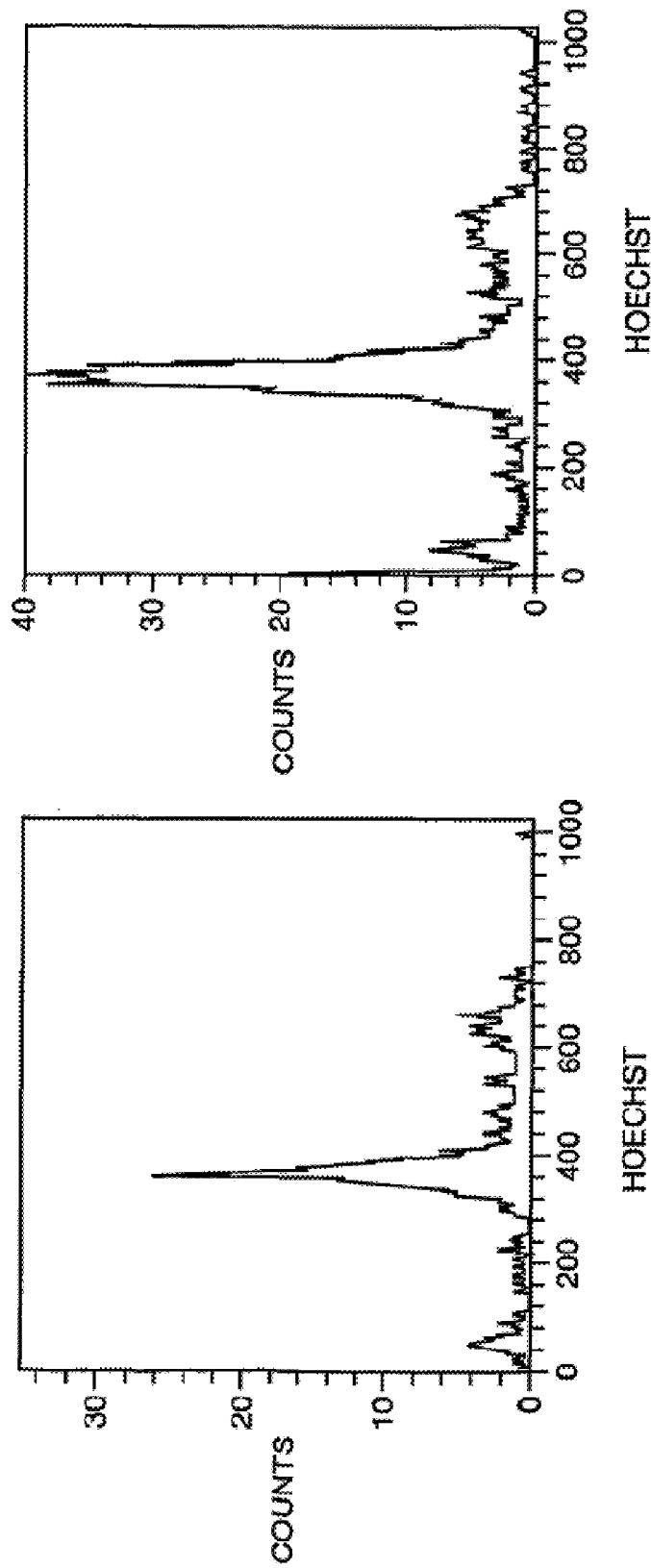
FIG. 19 is an analysis of different populations of cells in a breast cancer. ESA$^+$CD44$^+$CD24$^{-/lo}$LINEAGE$^-$ cells breast cancer stem cells (FIG. 19A) and ESA$^+$CD44$^+$CD24$^+$LINEAGE$^-$ non-tumorigenic cells (FIG. 19B) were obtained as described in FIG. 8. The cells were stained with Hoechst 33342 as described by Eaves and colleagues (Glimm H et al., Blood. 96(13): 4185-93 (2000)). The histogram for the breast cancer stem cells is shaded. Note that the breast cancer stem cells and the non-tumorigenic cells are distributed in all phases of the cells cycle.

Cell Cycle Analysis of Breast Cancer Stem Cells and Non-Tumorigenic Breast Cancer Cells We tested cells from a mouse xenograft tumor. The cell cycle status of the breast cancer stem cell (FIG. 19A) and non-tumorigenic populations of cells (FIG. 19B) in the tumor was determined by flow cytometry. There was a similar distribution of cells in the G1, S, and G2/M phases of the cell cycle in both populations. Thus, both the tumorigenic and non-tumorigenic populations exhibited similar cell-cycle distributions.

This EXAMPLE rules out the possibility that all cells that expressed the solid tumor stem cell markers were at a particular stage of the cell cycle in the tumor that was analyzed. By selecting cells at a particular stage of the cell-cycle by flow-cytometric sorting of Hoechst stained tumor stem cells it may be possible to further enrich tumorigenic activity, just as it has been possible to enrich hematopoietic stem cell activity by selecting cells with low levels of Hoechst staining

EXAMPLE 18

Rhodamine 123 Staining of Breast Cancer Stem Cells And Non-Tumorigenic Breast Cancer Cells The purpose of this EXAMPLE is to examine the activity of the multi-drug resistance pump in breast cancer stem cells and the non-tumorigenic cancer cells. We have stained the $ESA^+$ $CD44^+CD24^{-/lo}LINEAGE^-$ cells (breast cancer stem cells) and the non-tumorigenic cells obtained from one of the xenograft tumors with Rhodamine 123.

Figure 20:
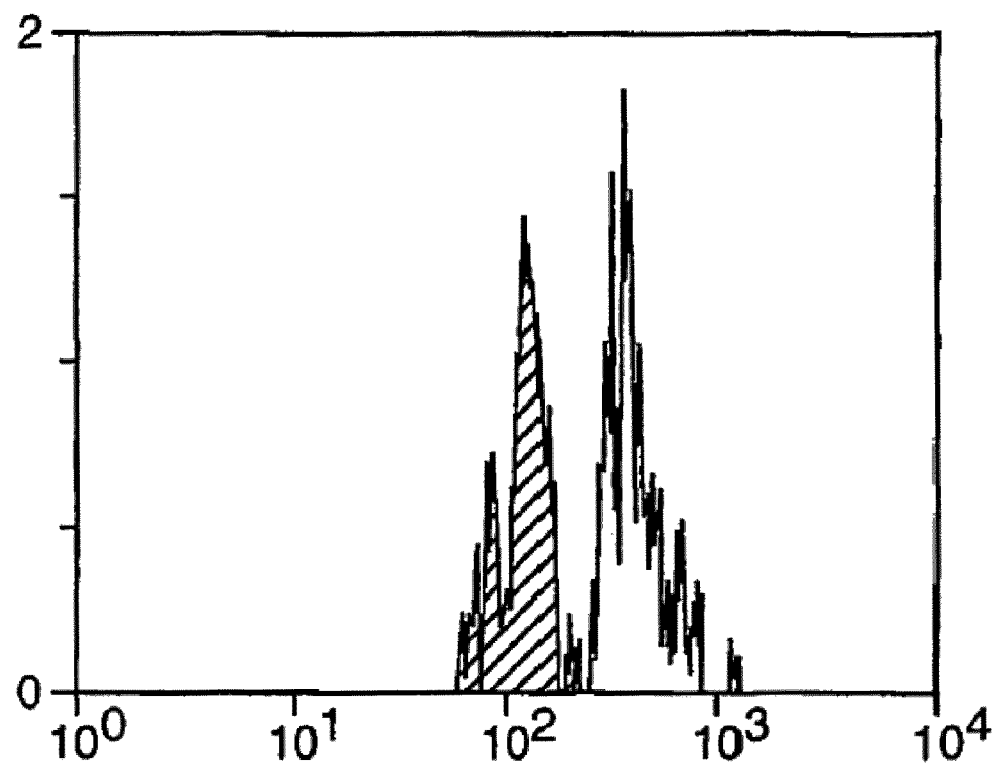
FIG. 20 is a further analysis of different populations of cells in a breast cancer. CD44$^+$CD24$^{-/lo}$ LINEAGE$^-$ cells breast cancer stem cells and non-tumorigenic CD44$^+$CD24$^+$ LINEAGE$^-$ non-tumorigenic cells were obtained as described in FIG. 7. The cells were stained with Rhodamine 123 as described by Spangrude et al., Blood 85(4):1006-16, 1995. The histogram for the breast cancer stem cells is shaded. Note that the breast cancer stem cells tend to stain less intensely with Rhodamine 123.

One of the major factors that determines the intensity of Rhodamine 123 staining in a cell is the MDR pump activity that eliminates this dye from the cells. Yumoto R. et al., Drug Metabolism & Disposition 29(2): 145-51 (2001); Daoud R. et al., Biochemistry 39(50): 15344-52 (2000). We found that some of the solid tumor stem cells from this tumor stained less intensely with Rhodamine 123 than did the non-tumorigenic cancer cells (FIG. 20).

This EXAMPLE shows tumor cell heterogeneity and indicates that MDR pump activity may be higher in a solid tumor cells.

EXAMPLE 19

A $B38.1^+CD44^+CD24^{-/lo}LINEAGE^-$ Population of Cells Exists in Ovarian Cancer Tumors We analyzed cancer cells obtained from both a tumor and ascites fluid obtained from a cyto-reduction surgery for a patient with ovarian cancer. Notably, B38.1 is known to be expressed by ovarian cancer cells. Surprisingly, the flow cytometry analysis revealed multiple cell populations, and there was a distinct $B38.1^+CD44^+CD24^{-/lo}LINEAGE^-$ population of cells (FIG. 21).

This distinct cell population phenotypically resembles the breast cancer stem cell and may represent an ovarian cancer stem cell.

EXAMPLE 20

A B38.1$^+$CD44$^+$CD24$^{-/lo}$LINEAGE$^-$ Population of Cells Exists in Sarcoma Tumors/Comparison to Breast Cancer Stem Cell Data The B38.1 antigen had previously been described to be expressed only in breast cancer and ovarian cancer. We established two sarcomas by placing sarcoma cells in the flanks of NOD/SCID mice that had been treated with VP16. One of the tumors was excised and examined by flow cytometry. Surprisingly, the sarcoma cells expressed the B38.1 antigen. Furthermore, there were three distinct cell populations with respect to CD44$^+$ high, low and negative (FIG. 22).

Thus sarcoma cells include a CD44$^+$ population that phenotypically resembles breast cancer stem cells and that may represent sarcoma stem cells.

TABLE 7

Tumorigenicity of Different Populations of Tumor T1 and T2 Cells

| Cells/ | # tumors/# of injections | | |
|---|---|---|---|
| injection | $8 \times 10^5$ | $5 \times 10^5$ | $2 \times 10^5$ |
| T1 cells | | | |
| CD44$^-$ | 0/2 | 0/2 | – |
| CD44$^+$ | 2/2 | 2/2 | – |
| B38.1$^-$ | 0/2 | 0/2 | – |
| B38.1$^+$ | 2/2 | 2/2 | – |
| CD24$^+$ | – | – | 1/6 |
| CD24$^-$ | – | – | 6/6 |
| T2 cells | | | |
| CD44$^-$ | 0/2 | 0/2 | – |
| CD44$^+$ | 2/2 | 2/2 | – |
| B38.1$^-$ | 0/2 | 0/2 | – |
| B38.1$^+$ | 2/2 | 2/2 | – |
| CD24$^+$ | – | – | 1/6 |
| CD24$^-$ | – | – | 6/6 |

Cells were isolated by flow cytometry as described in FIG. 2 based upon expression of the indicated marker and assayed for the ability to form tumors after injection of 2-8 × 10$^5$ cells into the mammary fat pad of NOD/SCID mice. The number of tumors that formed/the number of injections that were performed is indicated for each population of cells.

EXAMPLE 21

Preparation of Polynucleotide Probes

Single round RT labeling from total RNA source. The polynucleotides isolated from isolated solid tumor stem cells or enriched populations of solid tumor stem cells can be RNA extracted from the cells or complementary DNA (cDNA) made from the extracted RNA.

For some embodiments of the methods of the invention (such as those involving hybridization), labeled cDNA is useful. In one embodiment, we use the methods of single round RT labeling from total RNA source.

The quality of the RNA coming into a labeling reaction will have a marked effect on the quality of the hybridization. RNA preparations that look good by the standard molecular biology criteria can give poor results. Typical problems include disperse, fine-grain noise over the entire hybridized surface and non-specific binding of fluor to the zones of DNA immobilization on the slide. These problems seem likely to have some roots in contaminating carbohydrate, and as would be expected with carbohydrate, the problems are exacerbated by ethanol precipitations before and after labeling. Very impure preparations frequently produce visible aggregates if precipitated after labeling and ethanol precipitation, which are essentially resistant to solubilization. It is well known that nucleic acids form strong aggregates with carbohydrate when either dried together or when co-precipitated. This interaction is the basis for nucleic acid immobilization onto chromatography supports such as cellulose. To minimize this sort of problem, we recommend preparative procedures which use few or preferably no ethanol precipitations during RNA preparation and labeling. We use at least the volumes of extractant and washing solutions suggested for the number of cells being processed. Appropriate or slightly excessive extraction/wash volumes tend to minimize noise in a hybridization assay.

Methods that give satisfactory results are Triazol extraction (BRL) and Rneasy (Quiagen).

Total RNA is prepared from tissue (from solid tumor or xenograft tumor), tissue culture or enriched populations of solid tumor stem cells obtained by flow cytometry. We resuspend the prepared RNA in a volume that produces an RNA concentration of >6 mg/ml in DEPC water. If the RNA is recovered from a matrix as the final preparative step, and is still too dilute, we concentrate as needed for labeling, using a MicroCon 30 (Amicon) determine the concentration of the RNA. We test by reading a small sample (A260) in 50 mM NaOH.

For the nucleotide mix, we use 10× low T dNTPs (using 100 mM dNTPs from Pharmacia (St Louis, Mo., USA) [27-2035-02])

TABLE 8

NUCLEOTIDE MIX

| Nucleotide | μl | mM final (1/10) concentration |
|---|---|---|
| dGTP | 25 | 0.5 |
| dATP | 25 | 0.5 |
| dCTP | 25 | 0.5 |
| dTTP | 10 | 0.2 |
| water | 415 | |
| total volume | 500 | |

Fluorescent Nucleotides are from Amersham Life Sciences or Perkin Elmer Applied Biosystems Division. We use FluoroLink Cy3-dUTP (#401-896) or FluoroLink Cy5-dUTP. The Cy3 and Cy5 nucleotides come at concentration of 1 mM.

The R110 nucleotide comes at concentration of 0.1 mM, and must be dried and resuspended at 0.1× the initial volume to bring it to 1 mM. Currently, the factors of labeling efficiency, fluorescent yield, spectral separation, and tendency toward non-specific binding make the Cy3/Cy5 pair the most useful for the detection system.

For the labeling reaction, the primer can be Pharmacia oligo (dT) 12-18 (27-7858-01). Unlabeled nucleotide mixes are prepared from Pharmacia 100 mM stocks. The reverse transcriptase is BRL SuperScript II (18064-014). The 5× buffer is the buffer supplied with the polymerase.

For use in microarrays, normalization in a two fluor labeling is achieved by reference to housekeeping genes distributed through the microarray.

A cocktail of synthetic cDNAs produced using phage RNA polymerases on cloned E. coli genes in the pSP64 poly(A) vector as a mass standard and RNA quality standard. If possible, we also prepare a total RNA solution containing 100 μg of RNA in 17 μl of DEPC water. Otherwise, we ethanol precipitate 100 mg of total RNA to concentrate sample for labeling reaction. We take care to remove all residual 70% ethanol wash either by air drying or vacuum, as residual ethanol may impede the efficiency of labeling.

We resuspend the pellet in DEPC water to give a final volume of 17 ml. Any residual precipitate is removed by centrifugation. The RNA is added to the reaction last.

Fluor nucleotide (NTP) RT labeling: We add the following:

TABLE 9

REVERSE TRANSCRIPTASE LABELING

| Component | μl |
|---|---|
| 5X first strand buffer | 8 |
| Oligo (dT)12-18 (500 μg/ml) | 2 |
| 10X low dT NTP mix | 4 |
| Fluor dUTP (1 mM) | 4 |
| 0.1M DTT | 4 |
| RNAsin | 1 |
| syn mRNA std (0.06 μg) | 0.5 |
| 100 mg total RNA | 17.0 |
| total | 40 |

We vortex the sample after adding RNAsin. We minimize bubbles and foaming during the vortex or quick spin.

Next, we hold at 65° C. for 5 minutes, bring to 42° C. (program R1). Then, add 2 μl of SSII enzyme. Make sure enzyme is well mixed into the reaction. Next, incubate 42° C. for 25 minutes. Add 2 μl of SSII enzyme. Make sure enzyme is well mixed into the reaction. Then, incubate 42° C. for 35 minutes. Add 5 μl of 500 mM EDTA. Be sure to stop the reaction with EDTA before adding NaOH.

Add 10 ml of 1M NaOH. Incubate at 650 C for 60 minutes to hydrolyze residual RNA. Cool to room temperature and add 25 μl of 1 M Tris-HCl (pH 7.5).

For probe cleanup and analysis, we transfer to a Microcon 30, concentrate to about 20 μl (approx 3.5 min at 14,000 rpm in Eppendorf 5415C). We wash by adding 200 μl of TE (pH 7.5) and concentrating to about 20 μl (4-4.5 min @14,000 rpm). We recover the product by inverting the concentrator over a clean collection tube and spinning for 3 min @ 3000 rpm.

In some cases, the Cy5 probe may produce a gelatinous blue precipitate which is recovered in the concentrated volume. The presence of this material signals the presence of contaminants. The more extreme the contamination, the greater the fraction of probe which will be captured in this gel. Even if heat solubilized, this material tends to produce uniform, non-specific binding to the DNA targets.

When concentrating by centrifugal filtration, the times required to achieve the desired final volume are variable. Overly long spins can remove nearly all the water from the solution being filtered. Then, when fluor tagged nucleic acids are concentrated onto the filter in this fashion, they are very hard to remove. Thus, we approach the desired volume by conservative approximations of the required spin times.

We take a 2 μl aliquot of Cy5 probe for analysis, leaving 17-18 μl for hybridization, then run this probe on a 2% agarose gel in TAB (gel size is 6 cm wide×8.5 cm long, 2 mm wide teeth). For maximal sensitivity when running samples on a gel for fluor analysis, we use loading buffer with minimal dye and do add ethidium bromide to the gel or running buffer.

We scan the gel on a Molecular Dynamics Storm fluorescence scanner (Settings—red fluorescence, 200 micron resolution, 1000 volts on PMT). A successful labeling produces a dense smear of probe from 400 bp to >1000 bp, with little pile-up of low molecular weight transcripts. Weak labeling and significant levels of low molecular weight material indicate a poor labeling.

Hybridization. The blocking species is poly(dA) from Pharmacia (27-7988-01) (resuspended at 8 mg/ml); yeast tRNA from Sigma (R8759) (resuspended at 4 mg/ml); and CoT1 DNA from Life Technologies Inc. (concentrated 10 fold to 10 mg/ml).

The volume required for the hybridization is dependent on the size of array used. For hybridizations that require small volumes (20-25 μl), the probe volumes after microcon concentration can be too large. If so, then we add the blockers to the Cy3 probe and precipitate the Cy3 probe.

We add 8 mg poly (dA); 4 mg tRNA; and 10 mg CoT1 DNA per 10 ml hybridization.

TABLE 10

HYBRIDIZATION PROBE MIX

| Cy3 labeled probe | ~20 μl |
|---|---|
| poly dA (8 mg/ml) | 1 μl |
| yeast tRNA (4 mg/ml) | 1 μl |
| CoT1 DNA (10 mg/ml) | 1 μl |

We add 2 μl of 3 M sodium acetate (pH 5.5), then add 60 μl of ethanol, centrifuge, dry lightly, and resuspend in the ~17 μl of Cy5 probe. If the array requires approximately 40 μl of probe, then the Cy3 and Cy5 concentrates are pooled and the blockers are added directly, so no precipitation is required.

Then, we add 3 μl of 20×SSC per 20 μl of hybridization mix volume. At this point, we optionally add 1 μl of 50×Denhardt's blocking solution per 20 μl of hybridization mix. With very clean probe, the Denhardt's does not make any visible difference.

Then, we heat at 98° C. for 2 minutes, cool to 45° C. and add 0.2 μl of 10% SDS per 20 of hybridization mix volume, then apply to the array, and hybridize (16-24) hours at 65° e in a sealed, humidified chamber.

Washing. Residual unbound probe is removed from the slides by washing 2-5 minutes each at room temperature. The first wash is 0.5×SSC, 0.01% SDS. The second wash is 0.06× SSC. Air drying of the slides after this step can leave a fluorescent haze on the slide surface, so buffer is removed from the slides by a brief spin at low G. We place the slides in a slide holder and spin in a centrifuge equipped with a swinging carrier (horizontal) which can hold the slide holder. Most centrifuges that are adaptable to centrifuging microtiter plates can be used for this purpose The foregoing description has been presented only for the purposes of illustration and is not intended to limit the invention to the precise form disclosed, but by the claims appended hereto.

We claim:

1. A method for detecting gene expression in a single isolated solid tumor cell having a surface marker phenotype selected from the group consisting of:
   (a) B38.1$^+$ CD24$^+$;
   (b) B38.1$^+$ LINEAGE$^-$;
   (c) B38.1$^+$ CD24$^+$ LINEAGE$^-$;
   (d) CD44$^+$ CD24$^+$;
   (e) CD44$^+$ CD24$^+$ LINEAGE$^-$;
   (f) B38.1$^+$ CD24$^-$;
   (g) B38.1$^+$ CD24$^-$ LINEAGE$^-$;
   (h) HER2$^+$ B38.1$^+$ CD24$^-$ LINEAGE$^-$;
   (i) EGFR$^-$ B38.1$^+$ CD24$^-$ LINEAGE$^-$;
   (j) CD44$^+$ CD24$^{-/lo}$; and
   (k) CD44$^+$ CD24$^{-/lo}$ LINEAGE$^-$.
   said method comprising:
   (a) isolating the single solid tumor cell from a solid tumor of epithelial origin;
   (b) amplifying a transcript produced by said cell; and
   (c) detecting the presence of said amplified transcript 2. The method of claim 1, wherein the transcript is amplified using RT-PCR.

3. The method of claim 1, wherein more than one transcript is amplified.

4. The method of claim 1, wherein the single isolated solid tumor cell is a breast solid tumor cell.

5. The method of claim 1, wherein the single isolated solid tumor cell is a solid tumor stem cell.

6. The method of claim 5, wherein the single isolated solid tumor stem cell has been exposed to a biological agent.

7. The method of claim 5, which further comprises the step of:
   (a) comparing a gene expression pattern of the single isolated solid tumor stem cell with a control; or
   (b) comparing the presence of an amplified transcript of said isolated solid tumor stem cell with amplification of the transcript in a single isolated tumor cell from the solid tumor.

8. A method for detecting gene expression in a single isolated solid tumor stem cell having a surface marker phenotype selected from the group consisting of:
   (a) B38.1$^+$CD24$^+$;
   (b) B38.1$^+$CD24$^-$;
   (c) CD44$^+$CD24$^{-/lo}$;
   (d) CD44$^+$CD24$^{-/lo}$ LINEAGE;
   (e) B38.1$^+$LINEAGE$^-$; and
   (f) B38.1$^+$CD24$^-$ LINEAGE$^-$;
   said method comprising:
   (a) isolating the single solid tumor stem cell from a solid tumor of epithelial origin;
   (b) amplifying a transcript produced by said cell; and
   (c) detecting the presence of said amplified transcript.

9. The method of claim 5, wherein the solid tumor stem cell is a breast solid tumor stem cell.

10. The method of claim 8, wherein the transcript is amplified using RT-PCR.

11. The method of claim 8, wherein more than one transcript is amplified.

12. The method of claim 8, wherein the single isolated solid tumor stem cell is a breast solid tumor stem cell.

13. The method of claim 8, wherein the single isolated solid tumor stem cell has been exposed to a biological agent.

14. The method of claim 8, which further comprises the step of:
   (a) comparing a gene expression pattern of the single isolated solid tumor stem cell with a control; or
   (b) comparing the presence of an amplified transcript of said isolated solid tumor stem cell with amplification of the transcript in a single isolated tumor cell from the solid tumor.

15. The method of claim 1, wherein the single isolated solid tumor cell has been exposed to a biological agent.

16. The method of claim 1, wherein the surface marker phenotype is CD44$^+$CD24$^+$.

17. The method of claim 4, wherein the surface marker phenotype is CD44$^+$CD24$^+$.

18. The method of claim 8, wherein the surface marker phenotype is CD44$^+$CD24$^{-/lo}$.

19. The method of claim 8, wherein the surface marker phenotype is CD44$^+$CD24$^{-/lo}$LINEAGE$^-$.

20. The method of claim 9, wherein the surface marker phenotype is CD44$^+$CD24$^{-/lo}$.

21. The method of claim 9, wherein the surface marker phenotype is CD44$^+$CD24$^{-/lo}$LINEAGE$^-$.

\* \* \* \* \*